US012643948B2

(12) United States Patent
Li et al.

(10) Patent No.: US 12,643,948 B2
(45) Date of Patent: Jun. 2, 2026

(54) ANTI-PD-L1/ANTI-LAG-3 MULTIPLE ANTIGEN BINDING PROTEINS AND METHODS OF USE THEREOF

(71) Applicant: Nanjing GenScript Biotech Co., Ltd., Nanjing (CN)

(72) Inventors: Zhongdao Li, Nanjing (CN); Liusong Yin, Nanjing (CN); Tielin Zhou, Singapore (SG); Zhuo Fang, Nanjing (CN)

(73) Assignee: Nanjing GenScript Biotech Co., Ltd., Nanjing (CN)

( * ) Notice: Subject to any disclaimer, the term of this patent is extended or adjusted under 35 U.S.C. 154(b) by 1033 days.

(21) Appl. No.: 17/609,540

(22) PCT Filed: Jun. 12, 2020

(86) PCT No.: PCT/CN2020/095779
§ 371 (c)(1),
(2) Date: Nov. 8, 2021

(87) PCT Pub. No.: WO2020/249071
PCT Pub. Date: Dec. 17, 2020

(65) Prior Publication Data
US 2022/0220204 A1     Jul. 14, 2022

(30) Foreign Application Priority Data
Jun. 12, 2019    (WO) ................ PCT/CN2019/090904

(51) Int. Cl.
*C07K 16/28*            (2006.01)
(52) U.S. Cl.
CPC ...... *C07K 16/2827* (2013.01); *C07K 16/2803* (2013.01); *C07K 2317/31* (2013.01); *C07K 2317/53* (2013.01); *C07K 2317/565* (2013.01); *C07K 2317/569* (2013.01); *C07K 2317/76* (2013.01)

(58) Field of Classification Search
None
See application file for complete search history.

(56) References Cited

U.S. PATENT DOCUMENTS

| | | | | |
|---|---|---|---|---|
| 11,958,903 B2 * | 4/2024 | Zhang | ................ | C07K 16/2803 |
| 12,168,688 B2 * | 12/2024 | Yang | ................. | A61P 35/00 |
| 2020/0369770 A1 * | 11/2020 | Zhang | ................. | A61P 35/00 |

FOREIGN PATENT DOCUMENTS

| | | | |
|---|---|---|---|
| WO | WO 2018/014855 A1 | 1/2018 | |
| WO | WO-2019129211 A1 * | 7/2019 | .............. A61P 35/00 |

OTHER PUBLICATIONS

Extended European Search Report dated Jun. 6, 2023 in EPC 20823048.2 (9 pages).
International Search Report and Written Opinion mailed on Sep. 23, 2020 for International Application No. PCT/CN2020/095779 (14 pages).

* cited by examiner

*Primary Examiner* — Maher M Haddad
(74) *Attorney, Agent, or Firm* — Yong Chen; Lin Sun-Hoffman; Liu Chen & Hoffman LLP

(57) ABSTRACT

The present application provides multiple antigen binding proteins containing a first antigen binding portion that specifically binds an epitope on PD-L1, preferably human PD-L1, and a second antigen binding portion that specifically binds an epitope on LAG-3. Also provided are nucleic acids encoding the multiple antigen binding proteins, vectors comprising the nucleic acids, host cells comprising the vectors, and pharmaceutical compositions comprising the multiple antigen binding proteins, as well as methods for treating cancer using the multiple antigen binding proteins and pharmaceutical compositions.

11 Claims, 7 Drawing Sheets

Specification includes a Sequence Listing.

| | mPDL1HCv1-E-sLAG3 | mPDL1HCv5-E-sLAG3 | sLAG3-E-mPDL1HCv1 | sLAG3-E-mPDL1HCv5 |
|---|---|---|---|---|
| EC50 | 0.3592 | 0.1928 | 0.5041 | 0.5316 |

| | mPDL1LCv1-E-sLAG3-HCv1 | mPDL1LCv1-E-LAG3 -HCv5 | sLAG3-E-mPDL1LCv1-HCv1 |
|---|---|---|---|
| EC50 | 0.1138 | 0.2406 | 0.6971 |

| | sLAG3-E-mPDL1LCv1 -HCv5 | PDL1HCv1 | PDL1HCv5 | sdab-LAG3-IgG4PE | human IgG |
|---|---|---|---|---|---|
| EC50 | 0.5406 | 0.6510 | 0.3113 | ~0.001710 | ~0.008883 |

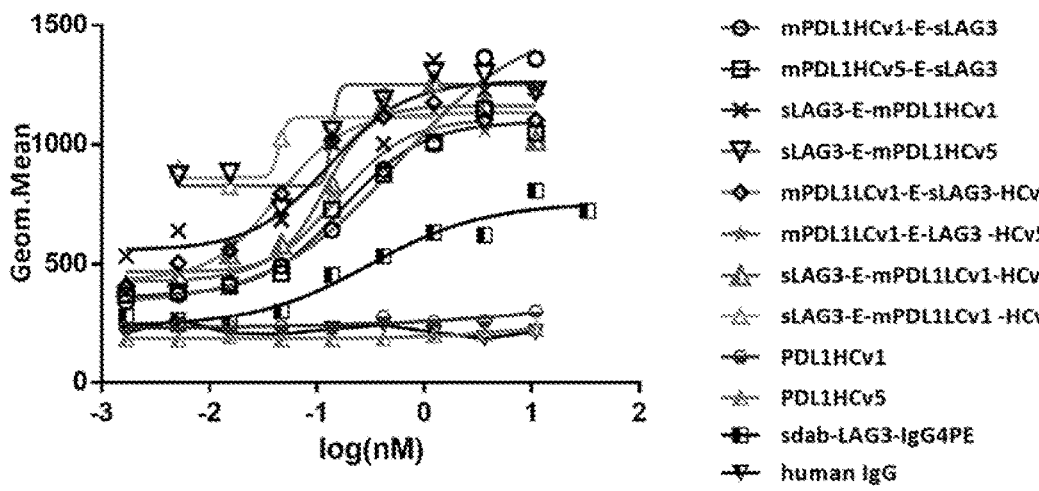

LAG3 FACS Binding Test

Legend:
- mPDL1HCv1-E-sLAG3
- mPDL1HCv5-E-sLAG3
- sLAG3-E-mPDL1HCv1
- sLAG3-E-mPDL1HCv5
- mPDL1LCv1-E-sLAG3-HCv1
- mPDL1LCv1-E-LAG3 -HCv5
- sLAG3-E-mPDL1LCv1-HCv1
- sLAG3-E-mPDL1LCv1 -HCv5
- PDL1HCv1
- PDL1HCv5
- sdab-LAG3-IgG4PE
- human IgG

| | mPDL1HCv1-E-sLAG3 | mPDL1HCv5-E-sLAG3 | sLAG3-E-mPDL1HCv1 | sLAG3-E-mPDL1HCv5 |
|---|---|---|---|---|
| EC50 | 0.5697 | 0.1715 | 0.1295 | ~0.1367 |

| | mPDL1LCv1-E-sLAG3-HCv1 | mPDL1LCv1-E-LAG3 -HCv5 | sLAG3-E-mPDL1LCv1-HCv1 |
|---|---|---|---|
| EC50 | 0.04369 | 0.1506 | 0.1194 |

| | sLAG3-E-mPDL1LCv1 -HCv5 | PDL1HCv1 | PDL1HCv5 | sdab-LAG3-IgG4PE | human IgG |
|---|---|---|---|---|---|
| EC50 | ~0.04462 | ~2.197e+008 | 8.417 | 0.3022 | |

FIG. 6

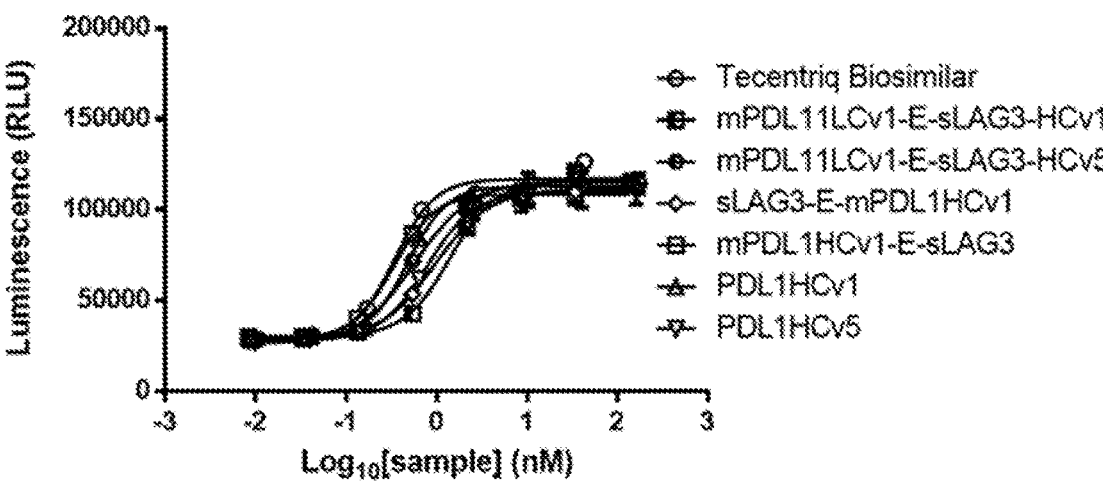

PD-1/PD-L1 Blockade Assay

Legend:
- Tecentriq Biosimilar
- mPDL11LCv1-E-sLAG3-HCv1
- mPDL11LCv1-E-sLAG3-HCv5
- sLAG3-E-mPDL1HCv1
- mPDL1HCv1-E-sLAG3
- PDL1HCv1
- PDL1HCv5

FIG. 7

| | mPDL1HCv1-G15-sLAG3 | mPDL1HCv1-G9-sLAG3 | mPDL1HCv1-Ea-sLAG3 |
|---|---|---|---|
| EC50 | 0.1874 | 0.2015 | 0.1967 |

| | mPDL1HCv1-E4-sLAG3 | mPDL1LCv1-E-sLAG3-HCv1 | mPDL1LCv1-E4-sLAG3-HCv1 |
|---|---|---|---|
| EC50 | 0.1890 | 0.2394 | 0.2237 |

| | sLAG3-E-mPDL1LCv1-HCv1 | sLAG3-G12-mPDL1HCv1 | PDL1HCv1 |
|---|---|---|---|
| EC50 | 0.5348 | 0.4397 | 0.2046 |

| | mPDL1HCv1-G15-sLAG3 | mPDL1HCv1-G9-sLAG3 | mPDL1HCv1-Ea-sLAG3 |
|---|---|---|---|
| EC50 | 0.3823 | 0.4002 | 0.5379 |

| | mPDL1HCv1-E4-sLAG3 | mPDL1LCv1-E-sLAG3-HCv1 | mPDL1LCv1-E4-sLAG3-HCv1 |
|---|---|---|---|
| EC50 | 0.3994 | 0.5614 | 0.5579 |

| | sLAG3-E-mPDL1LCv1-HCv1 | sLAG3-G12-mPDL1HCv1 | PDL1HCv1 | sdab-LAG3-IgG4PE |
|---|---|---|---|---|
| EC50 | 0.2387 | 0.3531 | 0.03763 | 0.2522 |

| | Tecentriq Biosimilar | mPDL1HCv1-G15-sLAG3 | mPDL1HCv1-G9-sLAG3 | mPDL1HCv1-Ea-sLAG3 |
|---|---|---|---|---|
| EC50 | 0.7380 | 0.3492 | 0.3886 | 0.5098 |

| | mPDL1LCv1-E-sLAG3-HCv1 | mPDL1HCv1-E4-sLAG3 | mPDL1LCv1-E4-sLAG3-HCv1 |
|---|---|---|---|
| EC50 | 0.3251 | 0.3673 | 0.4290 |

| | sLAG3-E-mPDL1LCv1-HCv1 | sLAG3-G12-mPDL1HCv1 | PDL1HCv1 |
|---|---|---|---|
| EC50 | 0.6154 | 0.5984 | 0.3146 |

| | 25F7 | mPDL1HCv1-G15-sLAG3 | PDL1HCv1-G9-LAG3 |
|---|---|---|---|
| EC50 | 0.8583 | 0.9236 | 1.098 |
| Span | 5466 | 11447 | 12232 |

| | mPDL1HCv1-Ea-sLAG3 | mPDL1LCv1-E-sLAG3-HCv1 | mPDL1HCv1-E4-sLAG3 |
|---|---|---|---|
| EC50 | 1.753 | 6.602 | 0.2511 |
| Span | 7758 | 3025 | 8234 |

| | 25F7 | mPDL1LCv1-E4-sLAG3-HCv1 | sLAG3-E-mPDL1LCv1-HCv1 |
|---|---|---|---|
| EC50 | 1.252 | 1.828 | 0.6795 |
| Span | 5544 | 6898 | 7326 |

| | sLAG3-G12-mPDL1HCv1 | sdab-LAG3-IgG4PE |
|---|---|---|
| EC50 | 1.636 | 3.327 |
| Span | 5784 | 5259 |

ANTI-PD-L1/ANTI-LAG-3 MULTIPLE ANTIGEN BINDING PROTEINS AND METHODS OF USE THEREOF

CROSS REFERENCE TO RELATED APPLICATION

This is the U.S. National Stage of International Application No. PCT/CN2020/095779, filed Jun. 12, 2020, which was published in English under PCT Article 21(2), which in turn claims priority to PCT/CN2019/090904, filed on Jun. 12, 2019, both of the disclosures of which are incorporated herein by reference in their entireties.

SUBMISSION OF SEQUENCE LISTING ON ASCII TEXT FILE

This application contains a sequence listing, which is submitted electronically via EFS-Web as an ASCII formatted sequence listing with a file name "Sequence Listing" and a creation date of Nov. 3, 2021 and having a size of 107 kb. The sequence listing is submitted via EFS-Web is part of the specification and is herein incorporated by reference in its entirety.

FIELD OF THE INVENTION

The present invention relates to multiple antigen binding proteins, especially bispecific antibodies, comprising a first antigen binding moiety that specifically binds an epitope on programmed death-ligand 1 (PD-L1) and a second antigen binding moiety that specifically binds an epitope on lymphocyte-activation gene 3 (LAG-3), pharmaceutical compositions containing such multiple antigen binding proteins, and methods of making and using thereof.

BACKGROUND OF THE INVENTION

The mammalian immune system is a host defense system to fight off pathogens and to protect against disease (Chen et al., Frontiers Immunol. 9: 320 (2018)). This pervasive and complex system is comprised of numerous immune cells, tissues and organs coordinated in a spatiotemporal manner. When it functions properly, the abnormal cells are identified and distinguished from the body's own healthy cells followed by elimination. So, the intact human immune system is essential for our survival. On the contrary, disorder of this system will lead to autoimmune diseases, inflammatory diseases and cancer (Ribas et al., Cancer Discovery 5: 915-9 (2015); Yao and Chen, Eur. J. Immunol. 43: 576-9 (2013)). The immune system can be broadly sorted into humoral immunity and cell-mediated immunity. The humoral immunity is mediated by macromolecules like antibodies. The cell-mediated immunity, by contrast, involves the activation of macrophages, natural killer cells (NK), and antigen-specific cytotoxic T-lymphocytes.

The activation and inhibition of immune response is largely mediated by two independent signaling pathways (Gorentla and Zhong, J. Clin. Cell. Immunol. (2012); Huse, J. Cell Sci. 122: 1269-73 (2009); Mizota et al., J. Anesthesia 27: 80-7 (2013)). The first signal is antigen-specific provided by the binding of specific T cell receptor (TCR) to antigenic peptide complexed with major histocompatibility complex (MHC) on the membrane of antigen presenting cells (APC). The second signal is antigen nonspecific through engagement of co-stimulatory molecules expressed on the membrane of APC and the T cells. Activation of T cells without co-stimulation results in T cell unresponsiveness or energy.

The lymphocyte response to antigen-receptor engagement is modulated by a series of co-stimulatory and co-inhibitory receptors involved in the second signaling pathway balancing the positive and negative signals to maximize immune responses against invaders while maintaining self-tolerance (Chen and Flies, Nat. Rev. Immunol. 13: 227-42 (2013); Ewing et al., Int. J. Cardiol. 168: 1965-74 (2013); Liu et al., Immunol. Invest. 45: 813-31 (2016); Shen et al., Frontiers in Biosci. 24: 96-132 (2019); Zhang and Vignali, Immunity 44: 1034-51 (2016)).

CD28, a member of the CD28 family, is a major T cell co-stimulatory receptor constitutively expressed on naive $CD4^+$ and $CD8^+$ T cells. Cytotoxic T lymphocyte-associated antigen 4 (CTLA-4), also a member of the CD28 receptor family, is a co-inhibitory receptor constitutively expressed on regulatory T cells (Treg) or induced following T-cell activation via CD28. Either CD28 or CTLA-4 can bind to the B7.1 (CD80) or B7.2 (CD86) ligands, which transmits activation or inhibition signal in T cells, respectively.

Ligands for the CD28 receptor include CD80, CD86, the programmed death-1 ligand (PD-L1), the programmed death-2 ligand (PD-L2) and others. In particular, PD-L1 is a transmembrane protein that binds to inhibitory checkpoint molecule of PD-1 leading to suppression of adaptive immune response by transmitting an inhibitory "don't find me" signal. The PD-1/PD-L1 signaling pathway plays an essential role in the development of immune tolerance by preventing over-reactivity of the immune system, and thus to avoid the development of autoimmune diseases (Dosset et al., Oncoimmunol. 7: e1433981 (2018); Feng et al., Canc. Lett. 407: 57-65 (2017); Salmaninejad et al., J. Cell. Physiol. (2019)). However, this is often deregulated during cancer progression, allowing tumor cells to bypass safeguarding mechanisms by masquerading as healthy tissues. Tumor cells that highly express PD-L1 can evade T-cell-mediated death and dampen anti-tumor adaptive immune response through activation of the PD-1/PD-L1 signaling pathway (Black et al., Immunotherapy 11: 585-90 (2019); Bocanegra et al., Int. J. Mol. Sci. 20 (2019); Carlsson et al., Appl. Immunohistochem. Mol. Morph. (2019); Davidsson et al., Eur. Urol. Oncol. 2: 214-21 (2019)). PD-1 overexpression in human tumor-associated macrophages (TAMs) has also been proven to inhibit phagocytosis and tumor immunity. Currently, anti-PD-1 or anti-PD-L1 monoclonal antibodies (mAbs) that interrupt the PD-1/PD-L1 interaction have shown exciting improvement in cancer treatment (Lee et al., Immuno-Oncol. (2019)). Despite the FDA approval of Keytruda, Opdivo and Tecentriq for the treatment of advanced cancers, more effective approaches are needed for immunotherapy improvement because these antitumor agents generate only a partial response.

Lymphocyte-activation gene 3 (LAG-3), is a transmembrane protein expressed on activated T cells, natural killer cells, B cells and plasmacytoid dendritic cells (Sierro et al., Exp. Opin. Therap. Targ. 15: 91-101 (2011)). LAG-3, like PD-1, is one of immune checkpoint receptors that binds to MHC II on APC and negatively regulates T cell receptor signaling (Andreae et al., Blood 102: 2130-7 (2003); Buisson and Triebel, Vaccine 21: 862-8 (2003)). Recently, Fibrinogen-like protein1 FGL1, a liver-secreted protein, is identified as another LAG3 functional ligand. As LAG-3 is also expressed on Treg cells (Huang et al., Immunity 21: 503-13 (2004)), blockade of LAG-3 could inhibit the activity of Tregs and enhance the antitumor immunity. LAG-3 blockade has been demonstrated with superior T cell activation compared to inhibition of other pathways, including PD-1/PD-L1 pathway (Goldberg and Drake, Curr. Top. Microbiol. Immunol. 344: 269-78 (2011); Long et al., Genes & Canc. 9: 176-89 (2018); Lui and Davis, Nat. Immunol. 19: 1278-9 (2018); Sierro et al., Exp. Opin. Therap. Targ. 15: 91-101 (2011)). More importantly, preclinical experiments have shown synergistic anti-tumor immunity by dual block-ade of PD-1/PD-L1 and LAG-3 signaling pathways (Butler et al., Nat. Immunol. 13: 188-95 (2011); Okazaki et al., J. Exper. Med. 208: 395-407 (2011); Woo et al., Canc. Res. 72: 917-27 (2012)).

The disclosures of all publications, patents, patent applications and published patent applications referred to herein are hereby incorporated herein by reference in their entirety.

BRIEF SUMMARY OF THE INVENTION

The present invention relates to constructs comprising a multiple antigen binding protein comprising a first antigen binding moiety that specifically binds an epitope on pro-grammed death-ligand 1 (PD-L1) and a second antigen binding moiety that specifically binds an epitope on lym-phocyte-activation gene 3 (LAG-3) and methods of making and using thereof.

Provided herein are isolated anti-PD-L1/anti-LAG-3 mul-tiple antigen binding proteins or antigen binding fragments thereof. The isolated anti-PD-L1/anti-LAG-3 multiple anti-gen binding protein or antigen binding fragment thereof comprises (a) a first antigen binding portion comprising a heavy chain variable domain ($V_H$) and a light chain variable domain ($V_L$), wherein the $V_H$ and $V_L$ together form an antigen-binding site that specifically binds PD-L1, and wherein the $V_H$ comprises a heavy chain complementarity determining region 1 (HCDR1), HCDR2, and HCDR3 com-prising the amino acid sequences of (i) SEQ ID NO:3, SEQ ID NO:4, and SEQ ID NO:5, respectively, or (ii) SEQ ID NO:9, SEQ ID NO:10, and SEQ ID NO:11, respectively; and the $V_L$ comprises a light chain complementarity deter-mining region 1 (LCDR1), LCDR2, and LCDR3 comprising the amino acid sequences of SEQ ID NO:6, SEQ ID NO:7, and SEQ ID NO:8, respectively; and (b) a second antigen binding portion comprising a single-domain antibody that specifically binds LAG-3; wherein the first antigen binding portion and the second antigen binding portion are fused to each other.

In certain embodiments, the second antigen binding por-tion comprises a single-domain antibody that comprises a complementarity determining region 1 (CDR1), CDR2, and CDR3 comprising the amino acid sequences of SEQ ID NO:33, SEQ ID NO:34, and SEQ ID NO:35, respectively.

In certain embodiments, the isolated anti-PD-L1/anti-LAG-3 multiple antigen binding protein or antigen binding fragment thereof comprises (a) a first antigen binding por-tion comprising a heavy chain variable domain ($V_H$) and a light chain variable domain ($V_L$), wherein the $V_H$ and $V_L$ together form an antigen-binding site that specifically binds PD-L1, and wherein the $V_H$ comprises a heavy chain complementarity determining region 1 (HCDR1), HCDR2, and HCDR3 comprising the amino acid sequences of (i) SEQ ID NO:3, SEQ ID NO:4, and SEQ ID NO:5, respec-tively, or (ii) SEQ ID NO:9, SEQ ID NO:10, and SEQ ID NO:11, respectively; and the $V_L$ comprises a light chain complementarity determining region 1 (LCDR1), LCDR2, and LCDR3 comprising the amino acid sequences of SEQ ID NO:6, SEQ ID NO:7, and SEQ ID NO:8, respectively; and (b) a second antigen binding portion comprising a single-domain antibody that specifically binds LAG-3, wherein the single-domain antibody comprises a comple-mentarity determining region 1 (CDR1), CDR2, and CDR3 comprising the amino acid sequences of SEQ ID NO:33, SEQ ID NO:34, and SEQ ID NO:35, respectively; wherein the first antigen binding portion and the second antigen binding portion are fused to each other.

In certain embodiments, the first antigen binding portion is a full-length antibody comprising two heavy chains and two light chains. The first antigen binding portion can, for example, be an antibody fragment comprising a heavy chain comprising the $V_H$ and a light chain comprising the $V_L$.

In certain embodiments, the second antigen binding por-tion comprises a single polypeptide chain. In certain embodiments, the first antigen binding portion and the second antigen binding portion are fused. The carboxy (C)-terminus of the second antigen binding portion can, for example, be fused to the amino (N)-terminus of at least one heavy chain of the first antigen binding portion or the amino (N)-terminus of at least one light chain of the first antigen binding portion. The amino (N)-terminus of the second antigen binding portion can, for example, be fused to the carboxy (C)-terminus of at least one heavy chain of the first antigen binding portion or the carboxy (C)-terminus of at least one light chain of the first antigen binding portion. In certain embodiments, the first antigen binding portion and the second antigen binding portion are fused to each other via a peptide bond or a peptide linker. In certain embodi-ments, the peptide linker is GS linker or a mutated human IgG1 hinge. The peptide linker can, for example, comprise an amino acid sequence selected from SEQ ID NO:12, SEQ ID NO:38 or SEQ ID NO:40-43.

In certain embodiments, the heavy chain of the first antigen binding portion comprises an amino acid sequence at least 95% identical to SEQ ID NO:14 or SEQ ID NO:18, and the light chain of the first antigen binding portion comprises an amino acid sequence at least 95% identical to SEQ ID NO:16. The heavy chain of the first antigen binding portion can comprise the amino acid sequence of SEQ ID NO:14 or SEQ ID NO:18, and the light chain of the first antigen portion can comprise the amino acid sequence of SEQ ID NO:16.

In certain embodiments, the second antigen binding por-tion comprises an amino acid sequence at least 95% iden-tical to an amino acid sequence of SEQ ID NO:37. The second antigen binding portion can comprise the amino acid sequence of SEQ ID NO:37.

In certain embodiments, the first antigen binding portion comprises a human, humanized or chimeric antibody or antigen binding fragment thereof. In certain embodiments, the second antigen binding portion comprising a single-domain antibody that specifically binds LAG-3 is camelid, chimeric, human, partially humanized, or fully humanized.

In certain embodiments, the isolated anti-PD-L1/anti-LAG-3 multiple antigen binding protein or antigen binding fragment thereof comprises an anti-PD-L1 full-length anti-body and an anti-LAG-3 single-domain antibody, wherein:

(a) the N-terminus of the anti-LAG-3 sdAb is fused to the C-terminus of both heavy chains of the anti-PD-L1 full-length antibody, and wherein the heavy chain fusion polypeptide comprises the amino acid sequence of SEQ ID NOs: 24, 28, 45, 47 or 49 and the light chain polypeptide comprises the amino acid sequence of SEQ ID NO:16;

(b) wherein the C-terminus of the anti-LAG-3 sdAb is fused to the N-terminus of both heavy chains of the anti-PD-L1 full-length antibody, and wherein the heavy chain fusion polypeptide comprises the amino acid sequence of SEQ ID NOs: 22, 26 or 51 and the light chain polypeptide comprises the amino acid sequence of SEQ ID NO:16;

(c) wherein the N-terminus of the anti-LAG-3 sdAb is fused to the C-terminus of both light chains of the anti-PD-L1 full-length antibody, and wherein the light chain fusion polypeptide comprises the amino acid sequence of SEQ ID NO:20 or 53 and the heavy chain polypeptide comprises the amino acid sequence of SEQ ID NO:14 or 18; or (d) wherein the C-terminus of the anti-LAG-3 sdAb is fused to the N-terminus of both light chains of the anti-PD-L1 full-length antibody, and wherein the light chain fusion polypeptide comprises the amino acid sequence of SEQ ID NO:30 and the heavy chain polypeptide comprises the amino acid sequence of SEQ ID NO:14 or 18.

Also provided is an isolated nucleic acid encoding an isolated anti-PD-L1/anti-LAG-3 multiple antigen binding protein or antigen binding fragment thereof as described herein.

Also provided is a vector comprising an isolated nucleic acid encoding an isolated anti-PD-L1/anti-LAG-3 multiple antigen binding protein or antigen binding fragment thereof as described herein.

Also provided is a host cell comprising an isolated nucleic acid or an isolated vector as described herein.

Further provided is a pharmaceutical composition comprising an isolated anti-PD-L1/anti-LAG-3 multiple antigen binding protein or antigen binding fragment as described herein, and a pharmaceutical acceptable carrier.

Another aspect of the present application provides a method of treating a subject having or at risk of having a PD-L1 and/or LAG-3-related disease, comprising administering to the individual an effective amount of any one of the pharmaceutical compositions as described herein. In some embodiments, the PD-L1 and/or LAG-3 related disease is cancer. In some embodiments, the cancer is a solid tumor, such as a colon cancer.

In some embodiments, the method further comprises administering to the individual an additional cancer therapy, such as surgery, radiation, chemotherapy, immunotherapy, hormone therapy, or a combination thereof.

In some embodiments, the PD-L1 related disease is a pathogenic infection.

In some embodiments, the pharmaceutical composition is administered systemically, such as intravenously (i.v.). In some embodiments, the pharmaceutical composition is administered locally, such as intratumorally. In some embodiments, the individual is a human.

Another aspect of the present application provides a method of producing any one of isolated anti-PD-L1/anti-LAG-3 multiple antigen binding proteins or antigen binding fragments described herein, comprising culturing a host cell comprising any one of the isolated nucleic acids or vectors described herein, or culturing any one of the isolated host cells described above, under conditions effective to express the encoded anti-PD-L1/anti-LAG-3 multiple antigen binding protein or antigen binding fragment thereof; and obtaining the expressed anti-PD-L1/anti-LAG-3 multiple antigen binding protein or antigen binding fragment thereof from said host cell. In some embodiments, the method further comprises producing a host cell comprising any one of the isolated nucleic acids or vectors described herein.

BRIEF DESCRIPTION OF THE DRAWINGS

The foregoing summary, as well as the following detailed description of the invention, will be better understood when read in conjunction with the appended drawings. For the purpose of illustrating the invention there are shown in the drawings embodiments which are presently preferred. It should be understood, however, that the invention is not limited to the precise arrangements and instrumentalities shown. In the drawings:

FIG. 6 depicts the results of a FACS binding assay using CHO-K1 cells expressing LAG-3.

FIG. 7 depicts the results of a PD-1/PD-L1 blockade bioassay.

DETAILED DESCRIPTION OF THE INVENTION

Figure 1:
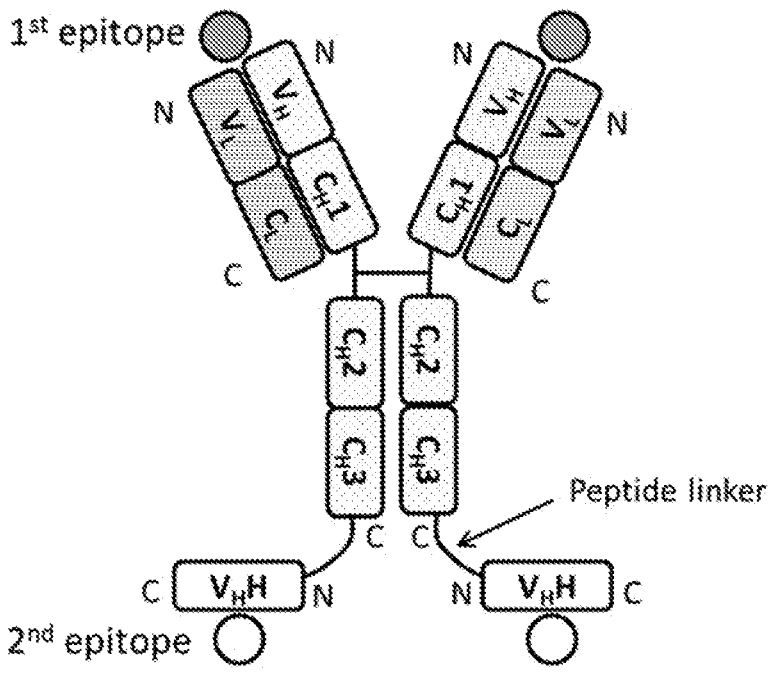
FIG. 1 depicts a schematic structure of an exemplary multiple antigen binding protein comprising a monospecific full-length antibody having two identical heavy chains and two identical light chains, and two identical single-domain antibodies (sdAbs), wherein the amino (N)-terminus of each sdAb is fused to the carboxy (C)-terminus of one heavy chain via an optional peptide linker (e.g., mPDL1HCv1-E-sLAG3 and mPDL1HCv5-E-sLAG3). The full-length antibody has two antigen binding sites that specifically bind a first epitope. The two sdAbs specifically bind the second epitope. For example, the multiple antigen binding protein can consist of four polypeptide chains with structures from the N-terminus to the C-terminus as follows: (1) $V_L$-$C_L$; (2) $V_H$-$C_H1$-$C_H2$-$C_H3$-$V_H$H; (3) $V_H$-$C_H1$-$C_H2$-$C_H3$-$V_H$H; and (4) $V_L$-$C_L$, wherein $V_H$ and $V_L$ of polypeptide chains (1) and (2) forms an antigen binding site that specifically binds a first copy of the first epitope, $V_H$ and $V_L$ of polypeptide chains (3) and (4) forms an antigen binding site that specifically binds a second copy of the first epitope, and each $V_H$H specifically binds a copy of the second epitope. In alternative formats, each sdAb may be replaced with two copies of the sdAb fused to each other.
Figure 2:
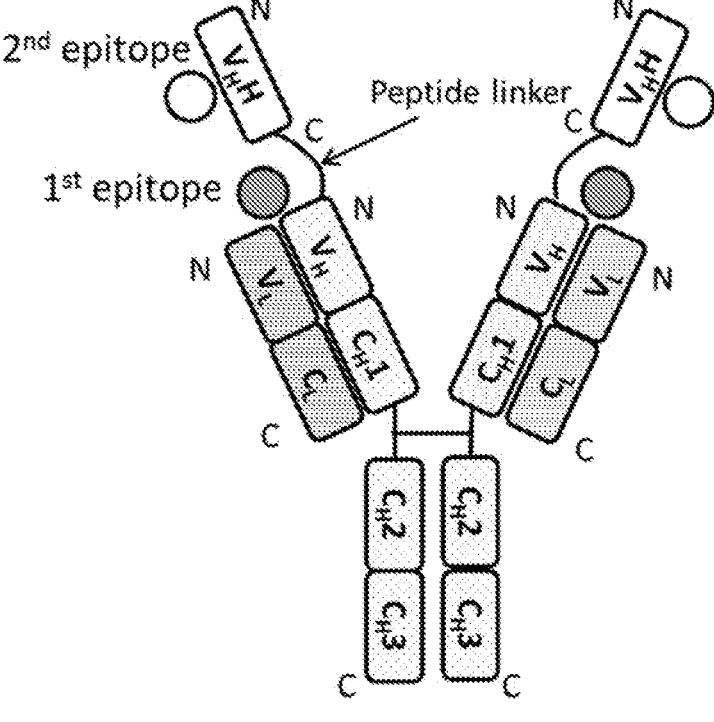
FIG. 2 depicts a schematic structure of an exemplary multiple antigen binding protein comprising a monospecific full-length antibody having two identical heavy chains and two identical light chains, and two identical sdAbs, wherein the C-terminus of each sdAb is fused to the N-terminus of one heavy chain (e.g., sLAG3-E-mPDL1HCv1 and sLAG3-E-mPDL1HCv5). The full-length antibody has two antigen binding sites that specifically bind a first epitope. The two sdAbs specifically bind the second epitope. For example, the multiple antigen binding protein can consist of four polypeptide chains with structures from the N-terminus to the C-terminus as follows: (1) $V_L$-$C_L$; (2) $V_H$H-$V_H$-$C_H1$-$C_H2$-$C_H3$; (3) $V_H$H-$V_H$-$C_H1$-$C_H2$-$C_H3$; and (4) $V_L$-$C_L$, wherein $V_H$ and $V_L$ of polypeptide chains (1) and (2) forms an antigen binding site that specifically binds a first copy of the first epitope, $V_H$ and $V_L$ of polypeptide chains (3) and (4) forms an antigen binding site that specifically binds a second copy of the first epitope, and each $V_H$H specifically binds a copy of the second epitope. In alternative formats, each sdAb may be omitted, or replaced with two identical or different sdAbs fused to each other. The monospecific full-length antibody may be replaced with a bispecific full-length antibody to further expand binding specificity.
Figure 3:
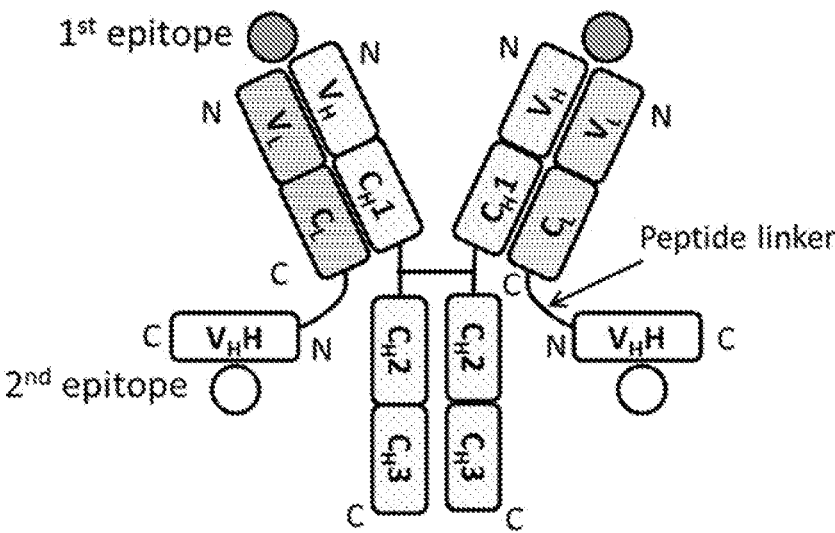
FIG. 3 depicts a schematic structure of an exemplary multiple antigen binding protein comprising a monospecific full-length antibody having two identical heavy chains and two identical light chains, and two identical sdAbs, wherein the N-terminus of each sdAb is fused to the C-terminus of one light chain via an optional peptide linker (e.g., mPDL1LCv1-E-sLAG3-HCv1 and mPDL1LCv1-E-sLAG3-HCv5). The full-length antibody has two antigen binding sites that specifically bind a first epitope. The two sdAbs specifically bind the second epitope. For example, the multiple antigen binding protein can consist of four polypeptide chains with structures from the N-terminus to the C-terminus as follows: (1) $V_L$-$C_L$-$V_H$H; (2) $V_H$-$C_H1$-$C_H2$-$C_H3$; (3) $V_H$-$C_H1$-$C_H2$-$C_H3$; and (4) $V_L$-$C_L$-$V_H$H, wherein $V_H$ and $V_L$ of polypeptide chains (1) and (2) forms an antigen binding site that specifically binds a first copy of the first epitope, $V_H$ and $V_L$ of polypeptide chains (3) and (4) forms an antigen binding site that specifically binds a second copy of the first epitope, and each $V_H$H specifically binds a copy of the second epitope. In alternative formats, each sdAb may be omitted, or replaced with two identical or different sdAbs fused to each other. The monospecific full-length antibody may be replaced with a bispecific full-length antibody to further expand binding specificity.
Figure 4:
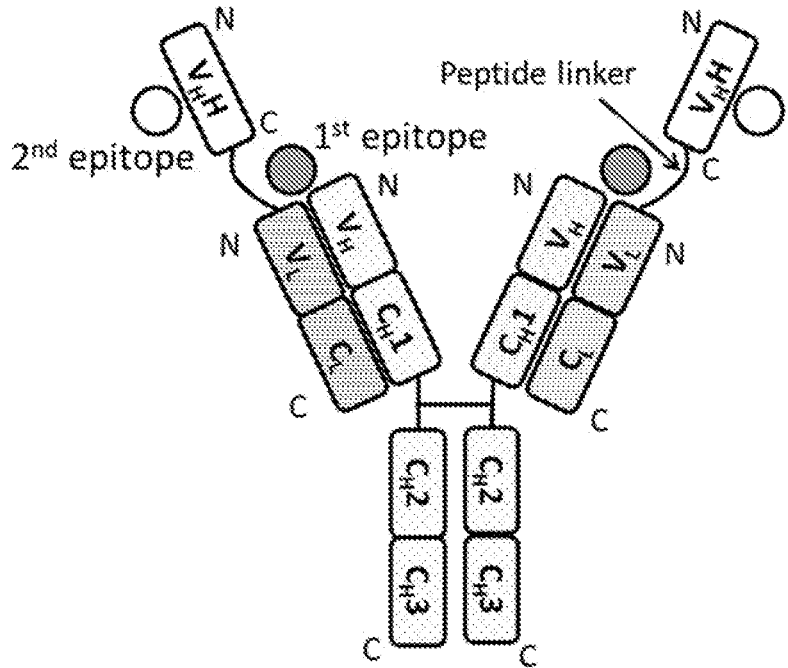
FIG. 4 depicts a schematic structure of an exemplary multiple antigen binding protein comprising a monospecific full-length antibody having two identical heavy chains and two identical light chains, and two identical sdAbs, wherein the C-terminus of each sdAb is fused to the N-terminus of one light chain via an optional peptide linker (e.g., sLAG3-E-mPDL1LCv1-HCv1 and sLAG3-mPDL1Cv1-HCv5). The full-length antibody has two antigen binding sites that specifically bind a first epitope. The two sdAbs specifically bind the second epitope. For example, the multiple antigen binding protein can consist of four polypeptide chains with structures from the N-terminus to the C-terminus as follows: (1) $V_H$H-$V_L$-$C_L$; (2) $V_H$-$C_H$1-$C_H$2-$C_H$3; (3) $V_H$-$C_H$1-$C_H$2-$C_H$3; and (4) $V_H$H-$V_L$-$C_L$, wherein $V_H$ and $V_L$ of polypeptide chains (1) and (2) forms an antigen binding site that specifically binds a first copy of the first epitope, $V_H$ and $V_L$ of polypeptide chains (3) and (4) forms an antigen binding site that specifically binds a second copy of the first epitope, and each $V_H$H specifically binds a copy of the second epitope. In alternative formats, each sdAb may be omitted, or replaced with two identical or different sdAbs fused to each other. The monospecific full-length antibody may be replaced with a bispecific full-length antibody to further expand binding specificity.

The present invention provides an isolated anti-PD-L1/anti-LAG-3 multiple antigen binding protein or antigen-binding fragment thereof. The isolated anti-PD-L1/anti-LAG-3 multiple antigen binding protein or antigen-binding fragment thereof comprises a first antigen binding portion comprising a heavy chain variable domain ($V_H$) and a light chain variable domain ($V_L$), wherein the $V_H$ and $V_L$ together form an antigen-binding site that specifically binds PD-L1, and a second antigen binding portion comprising a single-domain antibody (sdAb) that specifically binds LAG-3, and its antibody variants. As a building block in an anti-PD-L1/anti-LAG-3 multiple antigen binding protein or antigen binding fragment thereof, the anti-LAG-3 sdAb has sever advantages over other antigen binding fragments, such as Fab and scFv used in currently known multispecific formats. The advantages can include, but are not limited to, small size, high solubility and stability, and weak immunogenicity in human. Thus, the anti-PD-L1/anti-LAG-3 multiple antigen binding protein can have similar molecule weight and pharmacokinetic properties as compared to those of the full-length antibody or antigen binding fragment component.

Also provided are compositions (such as pharmaceutical compositions), kits and articles of manufacture comprising the anti-PD-L1/anti-LAG-3 multiple antigen binding proteins or antigen-binding fragments thereof, methods of making the anti-PD-L1/anti-LAG-3 multiple antigen binding proteins or antigen-binding fragments thereof, and methods of treating PD-L1 and/or LAG-3 related diseases (such as cancer) using the anti-PD-L1/anti-LAG-3 multiple antigen binding proteins or antigen binding fragments thereof.

I. Definitions

The practice of the present disclosure will employ, unless indicated specifically to the contrary, conventional methods of virology, immunology, microbiology, molecular biology and recombinant DNA techniques within the skill in the art, many of which are described below for the purpose of illustration. Such techniques are explained fully in the literature, see, e.g., Current Protocols in Molecular Biology or Current Protocols in Immunology, John Wiley & Sons, New York, N.Y. (2009); Ausubel et al., Short Protocols in Molecule Biology, 3rd Ed., Wiley & Sons, 1995; Sambrook and Russell, Molecule Cloning: A Laboratory Manual (3rd Edition, 2001); Maniatis et al., Molecule Cloning: A Laboratory Manual (1982); DNA Cloning: A Practical Approach, Vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984) and other like references.

The terms "Programmed cell death 1 ligand 1," "PD-L1," "B7 homolog 1 (B7-H1)," "PD-L1 antigen", "PDCD1 ligand 1" and "CD274" (see, e.g., Chemnitz (2004) J. Immunol. 173:945-954) are used interchangeably, and include variants, isoforms, species homologs of human PD-L1, and analogs having at least one common epitope with PD-L1 (see, e.g., Butte (2008) Mol Immunol. 45:3567-3572). Accordingly, the anti-PD-L1/anti-LAG-3 multiple antigen binding protein or antigen binding fragment thereof of the invention can, in certain cases, cross-react with PD-L1 from species other than human, or other proteins which are structurally related to human PD-L1 (e.g., human PD-L1 homologs). In other cases, the anti-PD-L1/anti-LAG-3 multiple antigen binding protein or antigen binding fragment thereof can be completely specific for human PD-L1 and not exhibit species or other types of cross-reactivity.

The term "human PD-L1" refers to human sequence PD-L1, such as the complete amino acid sequence of human PD-L1 having Genbank Accession Number Q9NZQ7. The human PD-L1 sequence can differ from human PD-L1 of Genbank Accession Number Q9NZQ7 by having, for example, conserved mutations or mutations in non-conserved regions and the PD-L1 has substantially the same biological function as the human PD-L1 of Genbank Accession Number Q9NZQ7. For example, a biological function of human PD-L1 is having an epitope in the extracellular domain of PD-L1 that is specifically bound by an anti-PD-L1/anti-LAG-3 multiple antigen binding protein or antigen

9 binding fragment thereof of the instant disclosure or a biological function of human PD-L1 is modulation of T cell activity.

The term "Programmed cell death 1 (PD-1)" as used herein is intended to refer to a cell surface receptor that belongs to the immunoglobulin superfamily and is expressed on T cells and pro-B cells. The amino acid sequences of human B7-1 (CD80) are disclosed at Genbank Accession Numbers NP_005009.

The term "LAG-3" refers to the lymphocyte-activation protein 3 (LAG-3), comprised of 503 amino acids, which belongs to the Ig superfamily and contains 4 extracellular Ig-like domains, designated D1 to D4. LAG-3 is closely related to CD4. LAG-3 is a cell surface protein expressed on activated T cells, NK cells, B cells, and plasmacytoid dendritic cells, and plays a role in the function of these lymphocyte subsets that is important but not completely understood. The LAG-3 protein negatively regulates cellular proliferation, activation, and homeostasis of T cells. LAG-3 also helps maintain CD8+ T cells in a tolerogenic state. The interaction between LAG-3 and its major ligand, Class II MHC, is thought to play a role in modulating dendritic cell functions. Recent preclinical studies have documented a role for LAG-3 in CD8 T cell exhaustion, and blockade of the LAG-3/Class II MHC interaction using LAG-3 blocking antibodies or LAG-3-Ig fusion proteins is being evaluated in a number of clinical trials in cancer patients.

The term "LAG-3" includes variants, isoforms, species homologs of human LAG-3, and analogs having at least one common epitope with LAG-3. Accordingly, the anti-PD-L1/ anti-LAG-3 multiple antigen binding protein or antigen binding fragment thereof of the invention can, in certain cases, cross-react with LAG-3 from species other than human, or other proteins which are structurally related to human LAG-3 (e.g., human LAG-3 homologs). In other cases, the anti-PD-L1/anti-LAG-3 multiple antigen binding protein or antigen binding fragment thereof can be completely specific for human LAG-3 and not exhibit species or other types of cross-reactivity.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing the quality of life, and/or prolonging survival. Also encompassed by "treatment" is a reduction of pathological consequence of cancer. The methods of the invention contemplate any one or more of these aspects of treatment.

The term "effective amount" used herein refers to an amount of an agent or a combination of agents, sufficient to treat a specified disorder, condition or disease such as ameliorate, palliate, lessen, and/or delay one or more of its symptoms. In reference to cancer, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay recurrence. An effective amount can be administered in one or more administrations. The effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

As used herein, an "individual" or a "subject" refers to a mammal, including, but not limited to, human, bovine, horse, feline, canine, rodent, or primate. In certain embodiments, the subject is a human.

The term "antibody" or "antibody moiety" is used in the broadest sense and encompasses various antibody structures, including but not limited to monoclonal antibodies, polyclonal antibodies, multispecific antibodies (e.g., bispecific antibodies), full-length antibodies and antigen-binding fragments thereof, so long as they exhibit the desired antigen-binding activity.

The basic 4-chain antibody unit is a heterotetrameric glycoprotein composed of two identical light (L) chains and two identical heavy (H) chains. An IgM antibody consists of 5 of the basic heterotetramer units along with an additional polypeptide called a J chain, and contains 10 antigen-binding sites, while IgA antibodies comprise from 2-5 of the basic 4-chain units which can polymerize to form polyvalent assemblages in combination with the J chain. In the case of IgGs, the 4-chain unit is generally about 150,000 Daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see e.g., *Basic and Clinical Immunology*, 8th Edition, Daniel P. Sties, Abba I. Terr and Tristram G. Parsolw (eds), Appleton & Lange, Norwalk, Conn., 1994, page 71 and Chapter 6. The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG and IgM, having heavy chains designated α, δ, ε, γ and μ, respectively. The γ and α classes are further divided into subclasses on the basis of relatively minor differences in the $C_H$ sequence and function, e.g., humans express the following subclasses: IgG1, IgG2A, IgG2B, IgG3, IgG4, IgA1 and IgA2.

An "isolated" antibody (or construct) is one that has been identified, separated and/or recovered from a component of its production environment (e.g., natural or recombinant). Preferably, the isolated polypeptide is free of association with all other components from its production environment. Contaminant components of its production environment, such as that resulting from recombinant transfected cells, are materials that would typically interfere with research, diagnostic or therapeutic uses for the antibody, and may include enzymes, hormones, and other proteinaceous or non-proteinaceous solutes. In preferred embodiments, the polypeptide will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator; or (3) to homogeneity by SDS-PAGE under non-reducing or reducing conditions using Coomassie Blue or, preferably, silver stain. An isolated antibody includes the antibody in situ within recombinant cells since at least one component of the antibody's natural environment will not be present. Ordinarily, however, an isolated polypeptide, antibody, or construct will be prepared by at least one purification step.

The "variable region" or "variable domain" of an antibody refers to the amino-terminal domains of the heavy or light chain of the antibody. The variable domains of the heavy chain and light chain may be referred to as "$V_H$" and "$V_L$", respectively. These domains are generally the most variable parts of the antibody (relative to other antibodies of the same class) and contain the antigen binding sites. Heavy-chain only antibodies from the Camelid species have a single heavy chain variable region, which is referred to as "$V_HH$". $V_HH$ is thus a special type of $V_H$.

The term "variable" refers to the fact that certain segments of the variable domains differ extensively in sequence among antibodies. The V domain mediates antigen binding and defines the specificity of a particular antibody for its particular antigen. However, the variability is not evenly distributed across the entire span of the variable domains. Instead, it is concentrated in three segments called complementary determining regions (CDRs) or hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies (see Kabat et al., *Sequences of Immunological Interest*, Fifth Edition, National Institute of Health, Bethesda, Md. (1991)). The constant domains are not involved directly in the binding of antibody to an antigen, but exhibit various effector functions, such as participation of the antibody in antibody-dependent cellular toxicity.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies and is not to be construed as requiring production of the antibody by any particular method. For example, the monoclonal antibodies to be used in accordance with the present invention may be made by a variety of techniques, including, for example, the hybridoma method (e.g., Kohler and Milstein., *Nature*, 256: 495-97 (1975); Hongo et al., *Hybridoma*, 14 (3): 253-260 (1995), Harlow et al., *Antibodies: A Laboratory Manual*, (Cold Spring Harbor Laboratory Press, $2^d$ ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature*, 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7: 33 (1993); U.S. Pat. Nos. 5,545,807; 5,545,806; 5,569,825; 5,625,126; 5,633,425; and 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995).

The terms "full-length antibody," "intact antibody," or "whole antibody" are used interchangeably to refer to an antibody in its substantially intact form, as opposed to an antibody fragment. Specifically, full-length 4-chain antibodies include those with heavy and light chains including an Fc region. Full-length heavy-chain only antibodies include the heavy chain (such as $V_HH$) and an Fc region. The constant domains may be native sequence constant domains (e.g., human native sequence constant domains) or amino acid sequence variants thereof. In some cases, the intact antibody may have one or more effector functions.

The term "constant domain" refers to the portion of an immunoglobulin molecule having a more conserved amino acid sequence relative to the other portion of the immunoglobulin, the variable domain, which contains the antigen-binding site. The constant domain contains the $C_H1$, $C_H2$ and $C_H3$ domains (collectively, CH) of the heavy chain and the CHL (or CL) domain of the light chain.

The "light chains" of antibodies (immunoglobulins) from any mammalian species can be assigned to one of two clearly distinct types, called kappa ("κ") and lambda ("λ"), based on the amino acid sequences of their constant domains.

An "antibody fragment" comprises a portion of an intact antibody, preferably the antigen binding and/or the variable region of the intact antibody. Examples of antibody fragments include, but are not limited to Fab, Fab', F(ab')$_2$ and Fv fragments; diabodies; linear antibodies (see U.S. Pat. No. 5,641,870, Example 2; Zapata et al., *Protein Eng.* 8(10): 1057-1062 [1995]); single-chain antibody molecules; single-domain antibodies (such as V$_H$H), and multispecific antibodies formed from antibody fragments. Papain digestion of antibodies produced two identical antigen-binding fragments, called "Fab" fragments, and a residual "Fc" fragment, a designation reflecting the ability to crystallize readily. The Fab fragment consists of an entire L chain along with the variable region domain of the H chain (V$_H$), and the first constant domain of one heavy chain (C$_H$1). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy-terminus of the C$_H$1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the V$_H$ and V$_L$ antibody domains connected into a single polypeptide chain. Preferably, the sFv polypeptide further comprises a polypeptide linker between the V$_H$ and V$_L$ domains which enables the sFv to form the desired structure for antigen binding. For a review of the sFv, see Pluckthun in *The Pharmacology of Monoclonal Antibodies*, vol. 113, Rosenburg and Moore eds., Springer-Verlag, New York, pp. 269-315 (1994).

"Functional fragments" of the antibodies described herein comprise a portion of an intact antibody, generally including the antigen binding or variable region of the intact antibody or the Fc region of an antibody which retains or has modified FcR binding capability. Examples of antibody fragments include linear antibody, single-chain antibody molecules and multispecific antibodies formed from antibody fragments.

The term "heavy chain-only antibody" or "HCAb" refers to a functional antibody, which comprises heavy chains, but lacks the light chains usually found in 4-chain antibodies. Camelid animals (such as camels, llamas, or alpacas) are known to produce HCAbs.

The term "single-domain antibody" or "sdAb" refers to a single antigen-binding polypeptide having three complementary determining regions (CDRs). The sdAb alone is capable of binding to the antigen without pairing with a corresponding CDR-containing polypeptide. In some cases, single-domain antibodies are engineered from camelid HCAbs, and their heavy chain variable domains are referred herein as "V$_H$Hs" (Variable domain of the heavy chain of the Heavy chain antibody). Some V$_H$Hs can also be known as nanobodies. Camelid sdAb is one of the smallest known antigen-binding antibody fragments (see, e.g., Hamers-Casterman et al., Nature 363: 446-8 (1993); Greenberg et al., Nature 374: 168-73 (1995); Hassanzadeh-Ghassabeh et al., Nanomedicine (Lond), 8: 1013-26 (2013)). A basic V$_H$H has the following structure from the N-terminus to the C-terminus: FR1-CDR1-FR2-CDR2-FR3-CDR3-FR4, in which FR1 to FR4 refer to framework regions 1 to 4, respectively, and in which CDR1 to CDR3 refer to the complementarity determining regions 1 to 3.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA,* 81: 6851-6855 (1984)). "Humanized antibody" is used as a subset of "chimeric antibodies".

"Humanized" forms of non-human (e.g., llama, camelid, and/or murine) antibodies are antibodies that contain minimal sequence derived from non-human immunoglobulin. In some embodiments, a humanized antibody is a human immunoglobulin (recipient antibody) in which residues from a CDR (hereinafter defined) of the recipient are replaced by residues from a CDR of a non-human species (donor antibody) such as mouse, rat, rabbit, camel, llama, alpaca, or non-human primate having the desired specificity, affinity, and/or capacity. In some instances, framework ("FR") residues of the human immunoglobulin are replaced by corresponding non-human residues. Furthermore, humanized antibodies can comprise residues that are not found in the recipient antibody or in the donor antibody. These modifications can be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, etc. The number of these amino acid substitutions in the FR is typically no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al., Nature 321: 522-525 (1986); Riechmann et al., Nature 332: 323-329 (1988); and Presta, *Curr. Op. Struct. Biol.* 2: 593-596 (1992). See also, for example, Vaswani and Hamilton, *Ann. Allergy, Asthma & Immunol.* 1: 105-115 (1998); Harris, *Biochem. Soc. Trans-actions* 23: 1035-1038 (1995); Hurle and Gross, *Curr. Op. Biotech.* 5: 428-433 (1994); and U.S. Pat. Nos. 6,982,321 and 7,087,409.

A "human antibody" is an antibody that possesses an amino-acid sequence corresponding to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.,* 227: 381 (1991); Marks et al., *J. Mol. Biol.,* 222: 581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.,* 147(1): 86-95 (1991). See also van Dijk and van de Winkel, *Curr. Opin. Pharmacol.,* 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Natl. Acad. Sci. USA,* 103: 3557-3562 (2006) regarding human antibodies generated via a human B-cell hybridoma technology.

The term "hypervariable region," "HVR," or "HV," when used herein refers to the regions of an antibody variable domain which are hypervariable in sequence and/or form structurally defined loops. Generally, 4-chain antibodies comprise six HVRs; three in the $V_H$ (H1, H2, H3), and three in the $V_L$ (L1, L2, L3). Single-domain antibodies comprise three HVRs (or CDRs): HVR1 (or CDR1), HVR2 (or CDR2), and HVR3 (or CDR3). In native 4-chain antibodies, H3 and L3 display the most diversity of the six HVRs, and in single-domain antibodies, HVR3 (or CDR3), display the most diversity of the three HVRs. H3, L3, and HVR3 are believed to play a unique role in conferring fine specificity to antibodies. See, e.g., Hamers-Casterman et al., *Nature* 363: 446-448 (1993); Sheriff et al., *Nature Struct. Biol.* 3: 733-736 (1996); Xu et al., *Immunity* 13: 37-45 (2000); Johnson and Wu, *Methods in Molecular Biology* 248: 1-25 (Lo, ed., Human Press, Totowa, NJ, 2003).

The term "Complementarity Determining Region" or "CDR" are used to refer to hypervariable regions as defined by the Kabat system. See Kabat et al., *Sequences of Proteins of Immunological Interest,* 5th Ed. Public Health Service, National Institutes of Health, Bethesda, Md. (1991).

A number of HVR delineations are in use and are encompassed herein. The Kabat Complementarity Determining Regions (CDRs) are based on sequence variability and are the most commonly used (Kabat et al., *Sequences of Proteins of Immunological Interest,* 5th Ed. Public Health Service, National Institutes of Health, Bethesda, Md. (1991)). Chothia refers instead to the location of the structural loops (Chothia and Lesk, *J. Mol. Biol.* 196: 901-917 (1987)). The AbM HVRs represent a compromise between the Kabat HVRs and Chothia structural loops and are used by Oxford Molecular's AbM antibody modeling software. The "contact" HVRs are based on an analysis of the available complex crystal structures. The residues from each of these HVRs are noted below in Table 1.

TABLE 1

| | | HVR delineations. | | |
|---|---|---|---|---|
| Loop | Kabat | AbM | Chothia | Contact |
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B |
| | | (Kabat Numbering) | | |
| H1 | H31-H35 | H26-H35 | H26-H32 | H30-H35 |
| | | (Chothia Numbering) | | |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the $V_L$ and 26-35 (H1), 50-65 or 49-65 (H2) and 93-102, 94-102, or 95-102 (H3) in the $V_H$. The variable domain residues are numbered according to Kabat et al., supra, for each of these definitions.

The amino acid residues of a single-domain antibody (such as $V_H H$) are numbered according to the general numbering for VH domains given by Kabat et al. ("Sequence of proteins of immunological interest", US Public Health Services, NIH Bethesda, Md., Publication No. 91), as applied to $V_H H$ domains from Camelids in the article of Riechmann and Muyldermans, J. Immunol. Methods 2000 Jun. 23; 240 (1-2): 185-195. According to this numbering, FR1 of a $V_H H$ comprises the amino acid residues at positions 1-30, CDR1 of a $V_H H$ comprises the amino acid residues at positions 31-35, FR2 of a $V_H H$ comprises the amino acids at positions 36-49, CDR2 of a $V_H H$ comprises the amino acid residues at positions 50-65, FR3 of a $V_H H$ comprises the amino acid residues at positions 66-94, CDR3 of a $V_H H$ comprises the amino acid residues at positions 95-102, and FR4 of a $V_H H$ comprises the amino acid residues at positions 103-113. In this respect, it should be noted that—as is well known in the art for $V_H$ domains and for $V_H H$ domains—the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering).

The expression "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g. residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

Unless indicated otherwise herein, the numbering of the residues in an immunoglobulin heavy chain is that of the EU index as in Kabat et al., supra. The "EU index as in Kabat" refers to the residue numbering of the human IgG1 EU antibody.

"Framework" or "FR" residues are those variable-domain residues other than the HVR residues as herein defined.

A "human consensus framework" or "acceptor human framework" is a framework that represents the most commonly occurring amino acid residues in a selection of human immunoglobulin $V_L$ or $V_H$ framework sequences. Generally, the selection of human immunoglobulin $V_L$ or $V_H$ sequences is from a subgroup of variable domain sequences. Generally, the subgroup of sequences is a subgroup as in Kabat et al., *Sequences of Proteins of Immunological Interest*, 5$^{th}$ Ed. Public Health Service, National Institutes of Health, Bethesda, Md. (1991). Examples include for the $V_L$, the subgroup may be subgroup kappa I, kappa II, kappa III or kappa IV as in Kabat et al., supra. Additionally, for the $V_H$, the subgroup may be subgroup I, subgroup II, or subgroup III as in Kabat et al. Alternatively, a human consensus framework can be derived from the above in which particular residues, such as when a human framework residue is selected based on its homology to the donor framework by aligning the donor framework sequence with a collection of various human framework sequences. An acceptor human framework "derived from" a human immunoglobulin framework or a human consensus framework may comprise the same amino acid sequence thereof, or it may contain preexisting amino acid sequence changes. In some embodiments, the number of pre-existing amino acid changes are 10 or less, 9 or less, 8 or less, 7 or less, 6 or less, 5 or less, 4 or less, 3 or less, or 2 or less.

An "affinity-matured" antibody is one with one or more alterations in one or more CDRs thereof that result in an improvement in the affinity of the antibody for antigen, compared to a parent antibody that does not possess those alteration(s). In some embodiments, an affinity-matured antibody has nanomolar or even picomolar affinities for the target antigen. Affinity-matured antibodies are produced by procedures known in the art. For example, Marks et al., *Bio/Technology* 10: 779-783 (1992) describes affinity maturation by $V_H$- and $V_L$-domain shuffling. Random mutagenesis of CDR and/or framework residues is described by, for example: Barbas et al. *Proc Nat. Acad. Sci. USA* 91: 3809-3813 (1994); Schier et al. *Gene* 169: 147-155 (1995); Yelton et al. *J. Immunol.* 155: 1994-2004 (1995); Jackson et al., *J. Immunol.* 154(7): 3310-9 (1995); and Hawkins et al, *J. Mol. Biol.* 226: 889-896 (1992).

As use herein, the term "specifically binds," "specifically recognizes," or is "specific for" refers to measurable and reproducible interactions such as binding between a target and an antibody, which is determinative of the presence of the target in the presence of a heterogeneous population of molecules including biological molecules. For example, an antibody that specifically binds a target (which can be an epitope) is an antibody that binds this target with greater affinity, avidity, more readily, and/or with greater duration than it binds other targets. In some embodiments, the extent of binding of an antibody to an unrelated target is less than about 10% of the binding of the antibody to the target as measured, e.g., by a radioimmunoassay (RIA). In some embodiments, an antibody that specifically binds a target has a dissociation constant ($K_d$) of $\leq 10^{-5}$ M, $\leq 10^{-6}$ M, $\leq 10^{-7}$ M, $\leq 10^{-8}$ M, $\leq 10^{-9}$ M, $\leq 10^{-10}$ M, $\leq 10^{-11}$ M, or $\leq 10^{-12}$ M. In some embodiments, an antibody specifically binds an epitope on a protein that is conserved among the protein from different species. In some embodiments, specific binding can include, but does not require exclusive binding.

The term "specificity" refers to selective recognition of an antigen binding protein or antibody for a particular epitope of an antigen. Natural antibodies, for example, are monospecific. The term "multispecific" as used herein denotes that an antigen binding protein or antibody has polyepitopic specificity (i.e., is capable of specifically binding to two, three, or more, different epitopes on one biological molecule or is capable of specifically binding to epitopes on two, three, or more, different biological molecules). "Bispecific" as used herein denotes that an antigen binding protein or antibody has two different antigen-binding specificities. Unless otherwise indicated, the order in which the antigens bound by a multiple antigen binding protein listed is arbitrary. That is, for example, the terms "anti-PD-L1/anti-LAG-3," "anti-PD-L1/anti-LAG-3," "LAG-3×PD-L1," "PD-L1×LAG-3," "LAG-3-PD-L1," and "PD-L1-LAG-3" may be used interchangeably to refer to multiple antigen binding proteins that specifically bind to both PD-L1 and LAG-3. The term "monospecific" as used herein denotes an antibody that has one or more binding sites each of which bind the same epitope of the same antigen.

The term "valent" as used herein denotes the presence of a specified number of binding sites in an antigen binding protein or antibody. A natural antibody for example or a full length antibody has two binding sites and is bivalent. As such, the terms "trivalent," "tetravalent," "pentavalent," and "hexavalent" denote the presence of three binding sites, four binding sites, five binding sites, and six binding sites, respectively, in an antigen binding protein or antibody. The bispecific antibodies of the present application are at least "bivalent."

A "blocking" antibody or an "antagonist" antibody is one that inhibits or reduces a biological activity of the antigen it binds. In certain embodiments, blocking antibodies or antagonist antibodies substantially or completely inhibit the biological activity of the antigen.

An "agonist" or activating antibody is one that enhances or initiates signaling by the antigen to which it binds. In certain embodiments, agonist antibodies cause or activate signaling without the presence of the natural ligand.

"Antibody effector functions" refer to those biological activities attributable to the Fc region (a native sequence Fc region or amino acid sequence variant Fc region) of an antibody and vary with the antibody isotype. Examples of antibody effector functions include: Clq binding and complement dependent cytotoxicity; Fc receptor binding; antibody-dependent cell-mediated cytotoxicity (ADCC); phagocytosis; down regulation of cell surface receptors (e.g., B cell receptors); and B cell activation. "Reduced or minimized" antibody effector function means that which is reduced by at least 50% (alternatively 60%, 65%, 70%, 75%, 80%, 85%, 90%, 95%, 96%, 97%, 98%, 99%) from the wild type or unmodified antibody. The determination of antibody effector function is readily determinable and measurable by one of ordinary skill in the art. In a preferred embodiment, the antibody effector functions of complement binding, complement dependent cytotoxicity and antibody dependent cytotoxicity are affected. In some embodiments, effector function is eliminated through a mutation in the constant region that eliminated glycosylation, e.g., "effectorless mutation." In one aspect, the effector-less mutation is an N297A or DANA mutation (D265A+N297A) in the $C_H2$ region. Shields et al., *J. Biol. Chem.* 276 (9): 6591-6604 (2001). Alternatively, additional mutations resulting in reduced or eliminated effector function include: K322A and L234A/L235A (LALA). Alternatively, effector function can be reduced or eliminated through production techniques, such as expression in host cells that do not glycosylate (e.g., *E. coli.*) or in which result in an altered glycosylation pattern that is ineffective or less effective at promoting effector function (e.g., Shinkawa et al., *J. Biol. Chem.* 278(5): 3466-3473 (2003).

"Antibody-dependent cell-mediated cytotoxicity" or ADCC refers to a form of cytotoxicity in which secreted Ig bound onto Fc receptors (FcRs) present on certain cytotoxic cells (e.g., natural killer (NK) cells, neutrophils and macrophages) enable these cytotoxic effector cells to bind specifically to an antigen-bearing target cell and subsequently kill the target cell with cytotoxins. The antibodies "arm" the cytotoxic cells and are required for killing of the target cell by this mechanism. The primary cells for mediating ADCC, NK cells, express FcγRIII only, whereas monocytes express FcγRI, FcγRII and FcγRIII. Fc expression on hematopoietic cells is summarized in Table 3 on page 464 of Ravetch and Kinet, *Annu. Rev. Immunol.* 9: 457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and natural killer (NK) cells. Alternatively, or additionally, ADCC activity of the molecule of interest may be assessed in vivo, e.g., in an animal model such as that disclosed in Clynes et al., *PNAS USA* 95: 652-656 (1998).

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies described herein include human IgG1, IgG2 (IgG2A, IgG2B), IgG3 and IgG4.

"Fc receptor" or "FcR" describes a receptor that binds the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see M. Daëron, *Annu. Rev. Immunol.* 15: 203-234 (1997). FcRs are reviewed in Ravetch and Kinet, *Annu. Rev. Immunol.* 9: 457-92 (1991); Capel et al., *Immunomethods* 4: 25-34 (1994); and de Haas et al., *J. Lab. Clin. Med.* 126: 330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus. Guyer et al., *J. Immunol.* 117: 587 (1976) and Kim et al., *J. Immunol.* 24: 249 (1994). Methods of measuring binding to FcRn are known (see, e.g., Ghetie and Ward, *Immunol. Today* 18: (12): 592-8 (1997); Ghetie et al., *Nature Biotechnology* 15 (7): 637-40 (1997); Hinton et al., *J. Biol. Chem.* 279 (8): 6213-6 (2004); WO 2004/92219 (Hinton et al.). Binding to FcRn in vivo and serum half-life of human FcRn high-affinity binding polypeptides can be assayed, e.g., in transgenic mice or transfected human cell lines expressing human FcRn, or in primates to which the polypeptides having a variant Fc region are administered. WO 2004/42072 (Presta) describes antibody variants which improved or diminished binding to FcRs. See also, e.g., Shields et al., *J. Biol. Chem.* 9(2): 6591-6604 (2001).

"Effector cells" are leukocytes which express one or more FcRs and perform effector functions. In one aspect, the effector cells express at least FcgRIII and perform ADCC effector function. Examples of human leukocytes which mediate ADCC include peripheral blood mononuclear cells (PBMC), natural killer (NK) cells, monocytes, cytotoxic T cells and neutrophils. The effector cells may be isolated from a native source, e.g., blood. Effector cells generally are lymphocytes associated with the effector phase, and function to produce cytokines (helper T cells), killing cells infected with pathogens (cytotoxic T cells) or secreting antibodies (differentiated B cells).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., *J. Immunol. Methods* 202: 163 (1996), may be performed. Antibody variants with altered Fc region amino acid sequences and increased or decreased C1q binding capability are described in U.S. Pat. No. 6,194,551B1 and WO99/51642. The contents of those patent publications are specifically incorporated herein by reference. See, also, Idusogie et al. *J. Immunol.* 164: 4178-4184 (2000).

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity that reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, wherein high-affinity antibodies generally bind antigen faster and tend to remain bound longer. A variety of methods of measuring binding affinity are known in the art, any of which can be used for purposes of the present application. Specific illustrative and exemplary embodiments for measuring binding affinity are described in the following.

"Binding specificity of the antibody or antigen-binding domain" can be determined experimentally by methods known in the art. Such methods comprise, but are not limited to Western blots, ELISA-, RIA-, ECL-, IRMA-, EIA-, BIAcore-tests and peptide scans.

"Half maximal inhibitory concentration (IC$_{50}$)" is a measure of the effectiveness of a substance (such as an antibody) in inhibiting a specific biological or biochemical function. It indicates how much of a particular drug or other substance (inhibitor, such as an antibody) is needed to inhibit a given biological process (e.g., the binding between PD-L1 and B7-1, the binding between LAG-3 and Class II MHC, or component of a process, i.e. an enzyme, cell, cell receptor or microorganism) by half. The values are typically expressed as molar concentration. IC$_{50}$ is comparable to an EC$_{50}$ for agonist drug or other substance (such as an antibody). EC$_{50}$ also represents the plasma concentration required for obtaining 50% of a maximum effect in vivo. As used herein, an "IC$_{50}$" is used to indicate the effective concentration of an antibody (such as an anti-PD-L1/anti-LAG-3 multiple antigen binding protein) needed to neutralize 50% of the antigen bioactivity (such as PD-L1 and/or LAG-3 bioactivity) in vitro. IC$_{50}$ or EC$_{50}$ can be measured by bioassays such as inhibition of ligand binding by FACS analysis (competition binding assay), cell based cytokine release assay, or amplified luminescent proximity homogeneous assay (AlphaLISA).

"Percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

An "isolated" nucleic acid molecule encoding an antibody or antigen-binding fragment thereof described herein is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies described herein is in a form other than in the form or setting in which it is found in nature. Isolated nucleic acid molecules therefore are distinguished from nucleic acid encoding the polypeptides and antibodies described herein existing naturally in cells. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell but may contain mutations. Mutant progeny that have the same function or biological activity as screened or selected for in the originally transformed cell are included herein.

"Adjuvant setting" refers to a clinical setting in which an individual has had a history of cancer, and generally (but not necessarily) been responsive to therapy, which includes, but is not limited to, surgery (e.g., surgery resection), radiotherapy, and chemotherapy. However, because of their history of cancer, these individuals are considered at risk of development of the disease. Treatment or administration in the "adjuvant setting" refers to a subsequent mode of treatment. The degree of risk (e.g., when an individual in the adjuvant setting is considered as "high risk" or "low risk") depends upon several factors, most usually the extent of disease when first treated.

"Neoadjuvant setting" refers to a clinical setting in which the method is carried out before the primary/definitive therapy.

The term "pharmaceutical formulation" of "pharmaceutical composition" refers to a preparation that is in such form as to permit the biological activity of the active ingredient to be effective, and that contains no additional components that are unacceptably toxic to a subject to which the formulation would be administered. Such formulations are sterile. A "sterile" formulation is aseptic or free from all living microorganisms and their spores.

It is understood that embodiments of the invention described herein include "consisting" and/or "consisting essentially of" embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter. For example, the method is not used to treat cancer of type X means the method is used to treat cancer of types other than X.

The term "about X-Y" used herein has the same meaning as "about X to about Y."

As used herein and in the appended claims, the singular forms "a," "or," and "the" include plural referents unless the context clearly dictates otherwise.

II. Anti-PD-L1/Anti-LAG-3 Multiple Antigen Binding Protein or Antigen-Binding Fragment Thereof One aspect of the present application provides a multi-specific antigen binding protein (MABP), e.g., an isolated anti-PD-L1/anti-LAG-3 multiple antigen binding protein or antigen-binding fragment thereof. The isolated anti-PD-L1/anti-LAG-3 multiple antigen binding proteins or antigen binding fragments thereof can, for example, comprise (a) a first antigen binding portion comprising a heavy chain variable domain ($V_H$) and a light chain variable domain ($V_L$), wherein the $V_H$ and $V_L$ together form an antigen-binding site that specifically binds PD-L1, and wherein the $V_H$ comprises a heavy chain complementarity determining region 1 (HCDR1), HCDR2, and HCDR3 comprising the amino acid sequences of (i) SEQ ID NO:3, SEQ ID NO:4, and SEQ ID NO:5, respectively, or (ii) SEQ ID NO:9, SEQ ID NO:10, and SEQ ID NO:11, respectively; and the $V_L$ comprises a light chain complementarity determining region 1 (LCDR1), LCDR2, and LCDR3 comprising the amino acid sequences of SEQ ID NO:6, SEQ ID NO:7, and SEQ ID NO:8, respectively; and (b) a second antigen binding portion comprising a single-domain antibody that specifically binds LAG-3; wherein the first antigen binding portion and the second antigen binding portion are fused to each other.

The isolated anti-PD-L1/anti-LAG-3 multiple antigen binding proteins or antigen binding fragments thereof can, for example, comprise (a) a first antigen binding portion comprising a heavy chain variable domain ($V_H$) and a light chain variable domain ($V_L$), wherein the $V_H$ and $V_L$ together form an antigen-binding site that specifically binds PD-L1, and wherein the $V_H$ comprises a heavy chain complementarity determining region 1 (HCDR1), HCDR2, and HCDR3 comprising the amino acid sequences of (i) SEQ ID NO:3, SEQ ID NO:4, and SEQ ID NO:5, respectively, or (ii) SEQ ID NO:9, SEQ ID NO:10, and SEQ ID NO:11, respectively; and the $V_L$ comprises a light chain complementarity determining region 1 (LCDR1), LCDR2, and LCDR3 comprising the amino acid sequences of SEQ ID NO:6, SEQ ID NO:7, and SEQ ID NO:8, respectively; and (b) a second antigen binding portion comprising a single-domain antibody that specifically binds LAG-3, wherein the single-domain antibody comprises a complementarity determining region 1 (CDR1), CDR2, and CDR3 comprising the amino acid sequences of SEQ ID NO:33, SEQ ID NO:34, and SEQ ID NO:35, respectively; wherein the first antigen binding portion and the second antigen binding portion are fused to each other.

In certain aspects of the present application, the first antigen binding portion is a full-length antibody comprising two heavy chains and two light chains. The first antigen binding portion can, for example, be an antibody fragment comprising a heavy chain comprising the $V_H$ and a light chain comprising the $V_L$. In certain aspects of the present application, the second antigen binding portion comprises a single polypeptide chain.

In certain aspects of the present application, the first antigen binding portion of the anti-PD-L1/anti-LAG-3 multiple antigen binding protein or antigen binding portion thereof comprises a heavy chain variable domain ($V_H$) with a heavy chain CDR1 comprising the amino acid sequence of SEQ ID NO:3 or a variant thereof comprising up to about 3 (such as about any of 1, 2, or 3) amino acid substitutions; a heavy chain CDR2 comprising the amino acid sequence of SEQ ID NO:4 or a variant thereof comprising up to about 3 (such as about any of 1, 2, or 3) amino acid substitutions; and a heavy chain CDR3 comprising the amino acid sequence of SEQ ID NO:5 or a variant thereof comprising up to about 3 (such as about any of 1, 2, or 3) amino acid substitutions; and a light chain variable domain ($V_L$) with a light chain CDR1 comprising the amino acid sequence of SEQ ID NO:6 or a variant thereof comprising up to about 3 (such as about any of 1, 2, or 3) amino acid substitutions; a light chain CDR2 comprising the amino acid sequence of SEQ ID NO:7 or a variant thereof comprising up to about 3 (such as about any of 1, 2, or 3) amino acid substitutions; and a light chain CDR3 comprising the amino acid sequence of SEQ ID NO:8 or a variant thereof comprising up to about 3 (such as about any of 1, 2, or 3) amino acid substitutions. In certain embodiments, the first antigen binding portion of the anti-PD-L1/anti-LAG-3 multiple antigen binding protein or antigen binding portion thereof comprises a heavy chain variable domain ($V_H$) with a heavy chain CDR1 comprising the amino acid sequence of SEQ ID NO:3; a heavy chain CDR2 comprising the amino acid sequence of SEQ ID NO:4; and a heavy chain CDR3 comprising the amino acid sequence of SEQ ID NO:5; and a light chain variable domain ($V_L$) with a light chain CDR1 comprising the amino acid sequence of SEQ ID NO:6; a light chain CDR2 comprising the amino acid sequence of SEQ ID NO:7; and a light chain CDR3 comprising the amino acid sequence of SEQ ID NO:8.

In certain aspects of the present application, the first antigen binding portion of the anti-PD-L1/anti-LAG-3 multiple antigen binding protein or antigen binding portion thereof comprises a heavy chain variable domain ($V_H$) with a heavy chain CDR1 comprising the amino acid sequence of SEQ ID NO:9 or a variant thereof comprising up to about 3 (such as about any of 1, 2, or 3) amino acid substitutions; a heavy chain CDR2 comprising the amino acid sequence of SEQ ID NO:10 or a variant thereof comprising up to about 3 (such as about any of 1, 2, or 3) amino acid substitutions; and a heavy chain CDR3 comprising the amino acid sequence of SEQ ID NO:11 or a variant thereof comprising up to about 3 (such as about any of 1, 2, or 3) amino acid substitutions; and a light chain variable domain ($V_L$) with a light chain CDR1 comprising the amino acid sequence of SEQ ID NO:6 or a variant thereof comprising up to about 3 (such as about any of 1, 2, or 3) amino acid substitutions; a light chain CDR2 comprising the amino acid sequence of SEQ ID NO:7 or a variant thereof comprising up to about 3 (such as about any of 1, 2, or 3) amino acid substitutions; and a light chain CDR3 comprising the amino acid sequence of SEQ ID NO:8 or a variant thereof comprising up to about 3 (such as about any of 1, 2, or 3) amino acid substitutions. In certain embodiments the first antigen binding portion of the anti-PD-L1/anti-LAG-3 multiple antigen binding protein or antigen binding portion thereof comprises a heavy chain variable domain ($V_H$) with a heavy chain CDR1 comprising the amino acid sequence of SEQ ID NO:9; a heavy chain CDR2 comprising the amino acid sequence of SEQ ID NO:10; and a heavy chain CDR3 comprising the amino acid sequence of SEQ ID NO:11; and a light chain variable domain ($V_L$) with a light chain CDR1 comprising the amino acid sequence of SEQ ID NO:6; a light chain CDR2 comprising the amino acid sequence of SEQ ID NO:7; and a light chain CDR3 comprising the amino acid sequence of SEQ ID NO:8.

In certain aspects of the present application, the first antigen binding portion of the anti-PD-L1/anti-LAG-3 multiple antigen binding protein or antigen binding fragment thereof comprises a heavy chain comprising the amino acid sequence of SEQ ID NO:14 or SEQ ID NO:18, and a light chain comprising an amino acid sequence of SEQ ID NO:16. In certain embodiments, the anti-PD-L1/anti-LAG-3 multiple antigen binding protein or antigen binding fragment thereof comprises a heavy chain that is at least 90%, 91%, 92%, 93%, 94%, 95%, 96%, 97%, 98%, 99% or more identical to the sequence set forth in SEQ ID NO:14 or SEQ ID NO:18, and a light chain that is at least 90%, 91%, 92%, 93%, 94%, 95%, 96%, 97%, 98%, 99% or more identical to the sequence set forth in SEQ ID NO:16.

In certain aspects of the present application, the second antigen binding portion of the anti-PD-L1/anti-LAG-3 multiple antigen binding protein or antigen binding portion thereof is an anti-LAG-3 sdAb moiety comprising a CDR1 comprising the amino acid sequence of SEQ ID NO:33, or a variant thereof comprising up to about 3 (such as about any of 1, 2, or 3) amino acid substitutions; a CDR2 comprising the amino acid sequence of SEQ ID NO:34, or a variant thereof comprising up to about 3 (such as about any of 1, 2, or 3) amino acid substitutions; and a CDR3 comprising the amino acid sequence of SEQ ID NO:35, or a variant thereof comprising up to about 3 (such as about any of 1, 2, or 3) amino acid substitutions.

In certain aspects of the present application, the second antigen binding portion of the anti-PD-L1/anti-LAG-3 multiple antigen binding protein or antigen binding portion thereof is an anti-LAG-3 sdAb moiety comprising a CDR1 comprising the amino acid sequence of SEQ ID NO:33; a CDR2 comprising the amino acid sequence of SEQ ID NO:34; and a CDR3 comprising the amino acid sequence of SEQ ID NO:35.

In certain aspects of the present application, the second antigen binding portion of the anti-PD-L1/anti-LAG-3 multiple antigen binding protein or antigen binding portion thereof is an anti-LAG-3 sdAb moiety comprising a $V_HH$ domain comprising the amino acid sequence of SEQ ID NO:37, or a variant thereof having at least about 80% (such as at least about any of 80%, 85%, 90%, 91%, 92%, 93%, 94%, 95%, 96%, 97%, 98%, or 99%) sequence identify to SEQ ID NO:37. In some embodiments, the anti-LAG-3 sdAb moiety comprising a $V_HH$ domain comprising the amino acid sequence of SEQ ID NO:37, or a variant thereof comprising up to about 3 (such as about any of 1, 2, or 3) amino acid substitutions in the WA domain. In some embodiments, the anti-LAG-3 sdAb moiety comprising the $V_HH$ domain comprising the amino acid sequence of SEQ ID NO:37 or a variant thereof comprises amino acid substitutions in CDRs, such as the CDR1, and/or the CDR2, and/or the CDR3. In some embodiments, the anti-LAG-3 sdAb moiety comprising the $V_HH$ domain comprising the amino acid sequence of SEQ ID NO:37 or a variant thereof comprises CDR1, CDR2, and CDR3 of SEQ ID NO:37, and the amino acid substitutions are in FRs, such as the FR1, and/or the FR2, and/or the FR3, and/or the FR4.

In certain aspects of the present application, the first antigen binding portion and the second antigen binding portion are fused. The carboxy (C)-terminus of the second antigen binding portion can, for example, be fused to the amino (N)-terminus of at least one heavy chain of the first antigen binding portion or the amino (N)-terminus of at least one light chain of the first antigen binding portion. The amino (N)-terminus of the second antigen binding portion can, for example, be fused to the carboxy (C)-terminus of at least one heavy chain of the first antigen binding portion or the carboxy (C)-terminus of at least one light chain of the first antigen binding portion. In certain embodiments, the first antigen binding portion and the second antigen binding portion are fused to each other via a peptide bond or a peptide linker. The peptide linker can, for example, comprise an amino acid sequence selected from SEQ ID NO:12, SEQ ID NO:38 or SEQ ID NO:40-43.

In certain aspects of the present application, the first antigen binding portion comprises a human, humanized or chimeric antibody or antigen binding fragment thereof. In certain embodiments, the second antigen binding portion comprising a single-domain antibody that specifically binds LAG-3 is camelid, chimeric, human, partially humanized, or fully humanized.

In certain aspects of the present application, the first antigen binding portion comprises an Fc region. In certain embodiments, the second antigen binding portion is fused to the N-terminus of the Fc region. The Fc region can, for example, be an IgG1 Fc. The Fc region can, for example, be an IgG4 Fc having an S228P mutation and/or an L235E mutation.

In some embodiments, there is provided an isolated anti-PD-L1/anti-LAG-3 multiple antigen binding protein or antigen binding fragment thereof comprising an anti-PD-L1 full-length antibody and an anti-LAG-3 single-domain antibody, wherein the N-terminus of the anti-LAG-3 sdAb is fused to the C-terminus of both heavy chains of the anti-PD-L1 full-length antibody, and wherein the heavy chain fusion polypeptide comprises the amino acid sequence of SEQ ID NOs:24, 28, 45, 47 or 49 and the light chain polypeptide comprises the amino acid sequence of SEQ ID NO:16.

In some embodiments, there is provided an isolated anti-PD-L1/anti-LAG-3 multiple antigen binding protein or antigen binding fragment thereof comprising an anti-PD-L1 full-length antibody and an anti-LAG-3 single-domain antibody, wherein the C-terminus of the anti-LAG-3 sdAb is fused to the N-terminus of both heavy chains of the anti-PD-L1 full-length antibody, and wherein the heavy chain fusion polypeptide comprises the amino acid sequence of SEQ ID NOs:22, 26 or 51 and the light chain polypeptide comprises the amino acid sequence of SEQ ID NO:16.

In some embodiments, there is provided an isolated anti-PD-L1/anti-LAG-3 multiple antigen binding protein or antigen binding fragment thereof comprising an anti-PD-L1 full-length antibody and an anti-LAG-3 single-domain antibody, wherein the N-terminus of the anti-LAG-3 sdAb is fused to the C-terminus of both light chains of the anti-PD-L1 full-length antibody, and wherein the light chain fusion polypeptide comprises the amino acid sequence of SEQ ID NO:20 or 53 and the heavy chain polypeptide comprises the amino acid sequence of SEQ ID NO:14 or 18. In some embodiments, there is provided an isolated anti-PD-L1/anti-LAG-3 multiple antigen binding protein or antigen binding fragment thereof comprising an anti-PD-L1 full-length antibody and an anti-LAG-3 single-domain antibody, wherein the N-terminus of the anti-LAG-3 sdAb is fused to the C-terminus of both light chains of the anti-PD-L1 full-length antibody, and wherein the light chain fusion polypeptide comprises the amino acid sequence of SEQ ID NO:20 and the heavy chain polypeptide comprises the amino acid sequence of SEQ ID NO:14 or 18. In some embodiments, there is provided an isolated anti-PD-L1/anti-LAG-3 multiple antigen binding protein or antigen binding fragment thereof comprising an anti-PD-L1 full-length antibody and an anti-LAG-3 single-domain antibody, wherein the N-terminus of the anti-LAG-3 sdAb is fused to the C-terminus of both light chains of the anti-PD-L1 full-length antibody, and wherein the light chain fusion polypeptide comprises the amino acid sequence of SEQ ID NO: 53 and the heavy chain polypeptide comprises the amino acid sequence of SEQ ID NO:14 or 18.

In some embodiments, there is provided an isolated anti-PD-L1/anti-LAG-3 multiple antigen binding protein or antigen binding fragment thereof comprising an anti-PD-L1 full-length antibody and an anti-LAG-3 single-domain antibody, wherein the C-terminus of the anti-LAG-3 sdAb is fused to the N-terminus of both light chains of the anti-PD-L1 full-length antibody, and wherein the light chain fusion polypeptide comprises the amino acid sequence of SEQ ID NO:30 and the heavy chain polypeptide comprises the amino acid sequence of SEQ ID NO:14 or 18.

In another general aspect, the present application relates to an isolated nucleic acid encoding an anti-PD-L1/anti-LAG-3 multiple antigen binding protein or antigen-binding fragment thereof described herein. It will be appreciated by those skilled in the art that the coding sequence of a protein can be changed (e.g., replaced, deleted, inserted, etc.) without changing the amino acid sequence of the protein. Accordingly, it will be understood by those skilled in the art that nucleic acid sequences encoding antibodies or antigen-binding fragments thereof of the invention can be altered without changing the amino acid sequences of the proteins.

In another general aspect, the present application relates to a vector comprising an isolated nucleic acid encoding an anti-PD-L1/anti-LAG-3 multiple antigen binding protein or antigen-binding fragment thereof described herein. Any vector known to those skilled in the art in view of the present disclosure can be used, such as a plasmid, a cosmid, a phage vector or a viral vector. In some embodiments, the vector is a recombinant expression vector such as a plasmid. The vector can include any element to establish a conventional function of an expression vector, for example, a promoter, ribosome binding element, terminator, enhancer, selection marker, and origin of replication. The promoter can be a constitutive, inducible or repressible promoter. A number of expression vectors capable of delivering nucleic acids to a cell are known in the art and can be used herein for production of an antibody or antigen-binding fragment thereof in the cell. Conventional cloning techniques or artificial gene synthesis can be used to generate a recombinant expression vector according to embodiments of the invention. Such techniques are well known to those skilled in the art in view of the present disclosure.

In another general aspect, the present application relates to a host cell comprising an isolated nucleic acid encoding an anti-PD-L1/anti-LAG-3 multiple antigen binding protein or antigen-binding fragment thereof described herein. Any host cell known to those skilled in the art in view of the present disclosure can be used for recombinant expression of multiple antigen binding protein or antigen-binding fragments thereof of the invention. In some embodiments, the host cells are *E. coli* TG1 or BL21 cells (for expression of, e.g., a scFv or Fab antibody), CHO-DG44 or CHO-K1 cells or HEK293 cells (for expression of, e.g., a full-length IgG antibody). According to particular embodiments, the recombinant expression vector is transformed into host cells by conventional methods such as chemical transfection, heat shock, or electroporation, where it is stably integrated into the host cell genome such that the recombinant nucleic acid is effectively expressed.

In another general aspect, the present application relates to a method of producing an anti-PD-L1/anti-LAG-3 multiple antigen binding protein or antigen-binding fragment thereof described herein, comprising culturing a cell comprising a nucleic acid encoding the multiple antigen binding protein or antigen-binding fragment thereof under conditions to produce the multiple antigen binding protein or antigen-binding fragment thereof of the invention, and recovering the multiple antigen binding protein or antigen-binding fragment thereof from the cell or cell culture (e.g., from the supernatant). Expressed multiple antigen binding proteins or antigen-binding fragments thereof can be harvested from the cells and purified according to conventional techniques known in the art and as described herein.

Anti-PD-L1 Monoclonal Antibody Moiety

The isolated anti-PD-L1/anti-LAG-3 multiple antigen binding protein or antigen-binding fragment thereof described herein comprises a first antigen-binding portion comprising a heavy chain variable domain ($V_H$) and a light chain variable domain ($V_L$), wherein the $V_H$ and $V_L$ together form an antigen-binding site that specifically binds PD-L1. The $V_H$ and $V_L$, can, for example be from an anti-PD-L1 monoclonal antibody. Anti-PD-L1 monoclonal antibodies or antigen-binding fragments there are described in PCT/CN2018/124925, filed on Dec. 28, 2019 and published as International Publication No. WO2019/129211 on Jul. 4, 2019, which is incorporated by reference herein in its entirety.

Anti-PD-L1 antibodies can, for example, include monoclonal antibodies, human antibodies, chimeric antibodies, humanized antibodies, primatized antibodies, bi-specific antibody (e.g., an anti-PD-L1/anti-LAG-3 multiple antigen binding protein), conjugated antibodies, a Small Modular ImmunoPharmaceuticals, single chain antibodies, camelid antibodies, CDR-grafted antibodies, and functional variants of an anti-PD-L1 antibody (such as, for example, a fusion protein), and fragments and derivatives thereof. These antibodies recognize and bind to PD-L1 protein, particularly human PD-L1. These antibodies can modulate, e.g., inhibit, block, antagonize, neutralize or otherwise interfere with PD-L1 expression, activity and/or signaling. These antibodies can modulate, e.g., inhibit, block, antagonize, neutralize or otherwise interfere with the interaction between PD-L1 and PD-1 (for example, human PD-L1 and human PD-1). These antibodies, including fragments, functional variants, and derivatives thereof, may be referred to collectively as "anti-PD-L1 antibodies of this disclosure," "disclosed anti-PD-L1 antibodies," "disclosed antibodies," "PD-L1 antibodies of this disclosure," and the like.

In certain embodiments, there is provided an anti-PD-L1 monoclonal antibody moiety comprising a heavy chain variable domain ($V_H$) with a heavy chain CDR1 comprising the amino acid sequence of SEQ ID NO:3 or a variant thereof comprising up to about 3 (such as about any of 1, 2, or 3) amino acid substitutions; a heavy chain CDR2 comprising the amino acid sequence of SEQ ID NO:4 or a variant thereof comprising up to about 3 (such as about any of 1, 2, or 3) amino acid substitutions; and a heavy chain CDR3 comprising the amino acid sequence of SEQ ID NO:5 or a variant thereof comprising up to about 3 (such as about any of 1, 2, or 3) amino acid substitutions; and a light chain variable domain ($V_L$) with a light chain CDR1 comprising the amino acid sequence of SEQ ID NO:6 or a variant thereof comprising up to about 3 (such as about any of 1, 2, or 3) amino acid substitutions; a light chain CDR2 comprising the amino acid sequence of SEQ ID NO:7 or a variant thereof comprising up to about 3 (such as about any of 1, 2, or 3) amino acid substitutions; and a light chain CDR3 comprising the amino acid sequence of SEQ ID NO:8 or a variant thereof comprising up to about 3 (such as about any of 1, 2, or 3) amino acid substitutions. In certain embodiments, there is provided an anti-PD-L1 monoclonal antibody moiety comprising a heavy chain variable domain ($V_H$) with a heavy chain CDR1 comprising the amino acid sequence of SEQ ID NO:3; a heavy chain CDR2 comprising the amino acid sequence of SEQ ID NO:4; and a heavy chain CDR3 comprising the amino acid sequence of SEQ ID NO:5; and a light chain variable domain ($V_L$) with a light chain CDR1 comprising the amino acid sequence of SEQ ID NO:6; a light chain CDR2 comprising the amino acid sequence of SEQ ID NO:7; and a light chain CDR3 comprising the amino acid sequence of SEQ ID NO:8.

In certain embodiments, there is provided an anti-PD-L1 monoclonal antibody moiety comprising a heavy chain variable domain ($V_H$) with a heavy chain CDR1 comprising the amino acid sequence of SEQ ID NO:9 or a variant thereof comprising up to about 3 (such as about any of 1, 2, or 3) amino acid substitutions; a heavy chain CDR2 comprising the amino acid sequence of SEQ ID NO:10 or a variant thereof comprising up to about 3 (such as about any of 1, 2, or 3) amino acid substitutions; and a heavy chain CDR3 comprising the amino acid sequence of SEQ ID NO:11 or a variant thereof comprising up to about 3 (such as about any of 1, 2, or 3) amino acid substitutions; and a light chain variable domain ($V_L$) with a light chain CDR1 comprising the amino acid sequence of SEQ ID NO:6 or a variant thereof comprising up to about 3 (such as about any of 1, 2, or 3) amino acid substitutions; a light chain CDR2 comprising the amino acid sequence of SEQ ID NO:7 or a variant thereof comprising up to about 3 (such as about any of 1, 2, or 3) amino acid substitutions; and a light chain CDR3 comprising the amino acid sequence of SEQ ID NO:8 or a variant thereof comprising up to about 3 (such as about any of 1, 2, or 3) amino acid substitutions. In certain embodiments, there is provided an anti-PD-L1 monoclonal antibody moiety comprising a heavy chain variable domain ($V_H$) with a heavy chain CDR1 comprising the amino acid sequence of SEQ ID NO:9; a heavy chain CDR2 comprising the amino acid sequence of SEQ ID NO:10; and a heavy chain CDR3 comprising the amino acid sequence of SEQ ID NO:11; and a light chain variable domain ($V_L$) with a light chain CDR1 comprising the amino acid sequence of SEQ ID NO:6; a light chain CDR2 comprising the amino acid sequence of SEQ ID NO:7; and a light chain CDR3 comprising the amino acid sequence of SEQ ID NO:8.

In certain embodiments, this disclosure provides an anti-PD-L1 monoclonal antibody moiety comprising a heavy chain comprising the amino acid sequence of SEQ ID NO:14 or SEQ ID NO:18, and a light chain comprising an amino acid sequence of SEQ ID NO:16. In certain embodiments, the anti-PD-L1 monoclonal antibody moiety comprises a heavy chain that is at least 90%, 91%, 92%, 93%, 94%, 95%, 96%, 97%, 98%, 99% or more identical to the sequence set forth in SEQ ID NO:14 or SEQ ID NO:18, and a light chain that is at least 90%, 91%, 92%, 93%, 94%, 95%, 96%, 97%, 98%, 99% or more identical to the sequence set forth in SEQ ID NO:16.

The anti-PD-L1 monoclonal antibody moiety provided herein exhibits inhibitory activity, for example, by inhibiting PD-L1 expression (e.g., inhibiting cell surface expression of PD-L1), activity, and/or signaling, or by interfering with the interaction between PD-L1 and PD-1. The anti-PD-L1 monoclonal antibody moiety provided herein completely or partially reduces or otherwise modulates PD-L1 expression or activity upon binding to, or otherwise interacting with, PD-L1, e.g., a human PD-L1. The reduction or modulation of a biological function of PD-L1 is complete, significant, or partial upon interaction between the anti-PD-L1 monoclonal antibody moiety and the human PD-L1 polypeptide and/or peptide.

The anti-PD-L1 monoclonal antibody moiety is considered to completely inhibit PD-L1 expression or activity when the level of PD-L1 expression or activity in the presence of the antibody is decreased by at least 95%, e.g., by 96%, 97%, 98%, 99% or 100% as compared to the level of PD-L1 expression or activity in the absence of interaction, e.g., binding, with the antibody moiety described herein.

The anti-PD-L1 monoclonal antibody moiety is considered to significantly inhibit PD-L1 expression or activity when the level of PD-L1 expression or activity in the presence of the anti-PD-L1 monoclonal antibody moiety is decreased by at least 50%, e.g., 55%, 60%, 75%, 80%, 85% or 90% as compared to the level of PD-L1 expression or activity in the absence of binding with an anti-PD-L1 monoclonal antibody moiety described herein. The anti-PD-L1 monoclonal antibody moiety is considered to partially inhibit PD-L1 expression or activity when the level of PD-L1 expression or activity in the presence of the antibody moiety is decreased by less than 95%, e.g., 10%, 20%, 25%, 30%, 40%, 50%, 60%, 75%, 80%, 85% or 90% as compared to the level of PD-L1 expression or activity in the absence of interaction, e.g., binding, with an antibody moiety described herein.

Anti-LAG-3 Single-Domain Antibody Moiety

The isolated anti-PD-L1/anti-LAG-3 multiple antigen binding protein or antigen-binding fragment thereof described herein comprises a second antigen-binding portion comprising a single-domain antibody (sdAb) moiety that specifically recognizes LAG-3 (or "anti-LAG-3 sdAb"). Anti-LAG-3 single-domain antibodies are described in PCT/CN2019/080528, filed on Mar. 29, 2019 and published as International Publication No. WO2019/185040 on Oct. 3, 2019, which is incorporated by reference herein in its entirety.

Single-Domain Antibody (sdAb) Moiety

Exemplary sdAb moieties include, but are not limited to, heavy chain variable domains from heavy-chain only antibodies (e.g., $V_H$H (Variable domain of the heavy chain of the Heavy chain antibody) in *Camelidae* or $V_{NAR}$ (Variable domain of the shark New Antigen Receptor) in cartilaginous fish), binding molecules naturally devoid of light chains, single domains (such as $V_H$ or $V_L$) derived from conventional 4-chain antibodies, humanized heavy-chain only antibodies, human single-domain antibodies produced by transgenic mice or rats expressing human heavy chain segments, and engineered domains and single domain scaffolds other than those derived from antibodies. The sdAb moieties may be derived from any species including, but not limited to mouse, rat, human, camel, llama, lamprey, fish, shark, goat, rabbit, and bovine. The sdAb moieties contemplated herein also include naturally occurring single-domain antibody molecules from species other than *Camelidae* and sharks.

In some embodiments, the sdAb moiety is derived from a naturally occurring single-domain antigen binding molecule known as heavy chain antibody devoid of light chains (also referred herein as "heavy chain-only antibodies", or "HCAb"). Such single domain molecules are disclosed in WO 94/04678 and Hamers-Casterman, C. et al. (1993) *Nature* 363: 446-448, for example. For clarity reasons, the variable domain derived from a heavy chain molecule naturally devoid of light chain is known herein as a $V_HH$ to distinguish it from the conventional VH of four chain immunoglobulins. Such a $V_HH$ molecule can be derived from antibodies raised in *Camelidae* species, for example, camel, llama, vicuna, dromedary, alpaca and guanaco. Other species besides *Camelidae* may produce heavy chain molecules naturally devoid of light chain, and such $V_HHs$ are within the scope of the present application.

In some embodiments, the sdAb moiety is recombinant, CDR-grafted, humanized, camelized, de-immunized and/or in vitro generated (e.g., selected by phage display). In some embodiments, the amino acid sequence of the framework regions may be altered by "camelization" of specific amino acid residues in the framework regions. Camelization refers to the replacing or substitution of one or more amino acid residues in the amino acid sequence of a (naturally occurring) $V_H$ domain from a conventional 4-chain antibody by one or more of the amino acid residues that occur at the corresponding position(s) in a $V_HH$ domain of a heavy chain antibody. This can be performed in a manner known per se, which will be clear to the skilled person, for example on the basis of the further description herein. Such "camelizing" substitutions are preferably inserted at amino acid positions that form and/or are present at the VH-VL interface, and/or at the so-called *Camelidae* hallmark residues, as defined herein (see for example WO 94/04678, Davies and Riechmann FEBS Letters 339: 285-290, 1994; Davies and Riechmann Protein Engineering 9 (6): 531-537, 1996; Riechmann J. Mol. Biol. 259: 957-969, 1996; and Riechmann and Muyldermans J. Immunol. Meth. 231: 25-38, 1999).

In some embodiments, the sdAb moiety is a human sdAb moiety produced by transgenic mice or rats expressing human heavy chain segments. See, e.g., US20090307787A1, U.S. Pat. No. 8,754,287, US20150289489A1, US20100122358A1, and WO2004049794. In some embodiments, the sdAb moiety is affinity matured.

In some embodiments, naturally occurring $V_HH$ domains against a particular antigen or target, can be obtained from (naive or immune) libraries of Camelid $V_{HH}$ sequences. Such methods may or may not involve screening such a library using said antigen or target, or at least one part, fragment, antigenic determinant or epitope thereof using one or more screening techniques known per se. Such libraries and techniques are for example described in WO 99/37681, WO 01/90190, WO 03/025020 and WO 03/035694. Alternatively, improved synthetic or semi-synthetic libraries derived from (naive or immune) $V_HH$ libraries may be used, such as $V_HH$ libraries obtained from (naive or immune) $V_HH$ libraries by techniques such as random mutagenesis and/or CDR shuffling, as for example described in WO 00/43507.

In some embodiments, the sdAb moieties are generated from conventional four-chain antibodies. See, for example, EP 0 368 684, Ward et al. (Nature 1989 Oct. 12; 341 (6242): 544-6), Holt et al., Trends Biotechnol., 2003, 21(11): 484-490; WO 06/030220; and WO 06/003388.

In some embodiments, there is provided an anti-LAG-3 sdAb moiety comprising a CDR1 comprising the amino acid sequence of SEQ ID NO:33, or a variant thereof comprising up to about 3 (such as about any of 1, 2, or 3) amino acid substitutions; a CDR2 comprising the amino acid sequence of SEQ ID NO:34, or a variant thereof comprising up to about 3 (such as about any of 1, 2, or 3) amino acid substitutions; and a CDR3 comprising the amino acid sequence of SEQ ID NO:35, or a variant thereof comprising up to about 3 (such as about any of 1, 2, or 3) amino acid substitutions.

In some embodiments, there is provided an anti-LAG-3 sdAb moiety comprising a CDR1 comprising the amino acid sequence of SEQ ID NO:33; a CDR2 comprising the amino acid sequence of SEQ ID NO:34; and a CDR3 comprising the amino acid sequence of SEQ ID NO:35.

In some embodiments, there is provided an anti-LAG-3 sdAb moiety comprising a $V_HH$ domain comprising the amino acid sequence of SEQ ID NO:37, or a variant thereof having at least about 80% (such as at least about any of 80%, 85%, 90%, 91%, 92%, 93%, 94%, 95%, 96%, 97%, 98%, or 99%) sequence identity to SEQ ID NO:37. In some embodiments, there is provided an anti-LAG-3 sdAb moiety comprising a $V_HH$ domain comprising the amino acid sequence of SEQ ID NO:37, or a variant thereof comprising up to about 3 (such as about any of 1, 2, or 3) amino acid substitutions in the $V_HH$ domain. In some embodiments, the anti-LAG-3 sdAb moiety comprising the $V_HH$ domain comprising the amino acid sequence of SEQ ID NO:37 or a variant thereof comprises amino acid substitutions in CDRs, such as the CDR1, and/or the CDR2, and/or the CDR3. In some embodiments, the anti-LAG-3 sdAb moiety comprising the $V_HH$ domain comprising the amino acid sequence of SEQ ID NO:37 or a variant thereof comprises CDR1, CDR2, and CDR3 of SEQ ID NO:37, and the amino acid substitutions are in FRs, such as the FR1, and/or the FR2, and/or the FR3, and/or the FR4.

Biological Activities

The biological activity of anti-LAG-3 sdAb described herein can be determined by measuring its half maximal effective concentration ($EC_{50}$), which is a measure of the effectiveness of an antibody in binding to its target, or half maximal inhibitory concentration ($IC_{50}$), which is a measure of the effectiveness of an antibody in inhibiting a specific biological or biochemical function (such as inhibiting the binding between LAG-3 and MHC class II molecules). For example, here $EC_{50}$ can be used to indicate the effective concentration of an anti-LAG-3 sdAb needed to bind 50% LAG-3 on cell surface, $IC_{50}$ can be used to indicate the effective concentration of anti-LAG-3 sdAb needed to neutralize 50% of LAG-3 bioactivity in vitro. $EC_{50}$ also represents the plasma concentration required for obtaining 50% of a maximum effect in vivo. $EC_{50}$ or $IC_{50}$ can be measured by assays known in the art, for example, bioassays such as FACS binding analysis, inhibition of ligand binding by FACS analysis (competition binding assay), cell-based cytokine release assay, or amplified luminescent proximity homogeneous assay (AlphaLISA).

For example, the blockade of ligand binding can be studied using flow cytometry. CHO cells expressing human LAG-3 can be dissociated from adherent culture flasks and mixed with varying concentrations of anti-LAG-3 sdAb for test, and a constant concentration of labeled-MHC class II protein. An anti-LAG-3 antibody positive control can be employed, such as BMS-986016 (Bristol-Myers Squibb). The mixture is equilibrated for 30 minutes at room temperature, washed three times with FACS buffer (PBS containing 1% BSA). Then, an antibody specifically recognizing the labeled MHC class II of constant concentration is added and incubated for 15 minutes at room temperature. Cells are washed with FACS buffer and analyzed by flow cytometry.

Data can be analyzed with Prism (GraphPad Software, San Diego, Calif.) using non-linear regression to calculate IC50. The results from the competition assay can demonstrate the ability of anti-LAG-3 sdAbs in inhibiting the interaction between MHC class II and LAG-3.

The biological activity of anti-LAG-3 sdAb can be tested using a LAG-3-blockade assay via a luciferase reporter. LAG-3 blockade reporter assay was performed using Promega LAG-3 blockade reporter assay kit (Promega, Cat #CS194819), according to the vendor's protocol. Briefly, Thaw-and-Use MHC-II APC Cells (including TCR Activating Antigen) can be plated overnight and then incubated with a serial dilution of anti-LAG-3 antibodies or anti-LAG-3 sdAb-Fc fusion proteins, followed by addition of Thaw-and-Use LAG-3 Effector cells. After 6 hours of induction at 37° C. and 5% $CO_2$, BIO-GLO™ Luciferase Assay Reagent can be added, and luminescence can be determined. The results can demonstrate the ability of anti-LAG-3 sdAbs in inhibiting the interaction between MHC class II and LAG-3.

In some embodiments, the anti-LAG-3 sdAb blocks or antagonizes signals transduced by the LAG-3 receptor. In some embodiments, the anti-LAG-3 sdAb can bind to an epitope on LAG-3 so as to inhibit LAG-3 from interacting with MHC class II molecules. In some embodiments, the anti- LAG-3 sdAb can reduce the binding of LAG-3 to MHC class II molecules by at least about any one of 5%, 10%, 20%, 25%, 30%, 40%, 50%, 60%, 70%, 75%, 80%, 90%, 95%, 99% or 99.9%.

Peptide Linkers

In some embodiments, the first and second antigen binding portions within the anti-PD-L1/anti-LAG-3 multiple antigen binding protein or antigen-binding fragment thereof can be optionally connected by a peptide linker. The length, the degree of flexibility and/or other properties of the peptide linker(s) used in the anti-PD-L1/anti-LAG-3 multiple antigen binding protein or antigen binding fragment thereof may have some influence on properties, including but not limited to the affinity, specificity or avidity for one or more particular antigens or epitopes. For example, longer peptide linkers may be selected to ensure that two adjacent domains do not sterically interfere with one another. In some embodiment, a peptide linker comprises flexible residues (such as glycine and serine) so that the adjacent domains are free to move relative to each other. For example, a glycine-serine doublet can be a suitable peptide linker.

The peptide linker can be of any suitable length. In some embodiments, the peptide linker is at least about any of 1, 2, 3, 4, 5, 6, 7, 8, 9, 10, 11, 12, 13, 14, 15, 16, 17, 18, 19, 20, 25, 30, 35, 40, 50, 75, 100 or more amino acids long. In some embodiments, the peptide linker is no more than about any of 100, 75, 50, 40, 35, 30, 25, 20, 19, 18, 17, 16, 15, 14, 13, 12, 11, 10, 9, 8, 7, 6, 5 or fewer amino acids long. In some embodiments, the length of the peptide linker is any of about 1 amino acid to about 10 amino acids, about 1 amino acid to about 20 amino acids, about 1 amino acid to about 30 amino acids, about 5 amino acids to about 15 amino acids, about 10 amino acids to about 25 amino acids, about 5 amino acids to about 30 amino acids, about 10 amino acids to about 30 amino acids long, about 30 amino acids to about 50 amino acids, about 50 amino acids to about 100 amino acids, or about 1 amino acid to about 100 amino acids.

The peptide linker may have a naturally occurring sequence, or a non-naturally occurring sequence. For example, a sequence derived from the hinge region of heavy chain only antibodies may be used as the linker. See, for example, WO1996/34103. In some embodiments, the peptide linker is a mutated human IgG1 hinge. In some embodiments, the peptide linker is a flexible linker. Exemplary flexible linkers include glycine polymers (G), glycine-serine polymers (including, for example, (GS), $(GSGGS)_n$, $(GGGS)_n$, and $(GGGGS)_n$, where n is an integer of at least one), glycine-alanine polymers, alanine-serine polymers, and other flexible linkers known in the art. In some embodiments, the peptide linker comprises the amino acid sequence of SEQ ID NO:38 (GGGGSGGGGSGGGGS), SEQ ID NO:41 (GGGGSGGGS) or SEQ ID NO: 42 (GGGGSGGGGSGS). In some embodiments, the peptide linker comprises the amino acid sequence of SEQ ID NO:12 (EPKSSDKTHTSPPSP), SEQ ID NO: 40 (ESKY-GPPSPPSP) or SEQ ID NO: 43 (EPKSSDKGHGGPPGP).

Chimeric or Humanized Anti-PD-L1/Anti-LAG-3 Multiple Antigen Binding Protein or Antigen Binding Fragment Thereof In some embodiments, the anti-PD-L1/anti-LAG-3 multiple antigen binding protein or antigen binding fragment thereof provided herein is a chimeric antibody. Certain chimeric antibodies are described, e.g., in U.S. Pat. No. 4,816,567; and Morrison et al., *Proc. Natl. Acad. Sci. USA*, 81: 6851-6855 (1984)). In one example, a chimeric antibody comprises a non-human variable region (e.g., a variable region derived from a camelid species, such as llama) and a human constant region. In a further example, a chimeric antibody is a "class switched" antibody in which the class or subclass has been changed from that of the parent antibody. Chimeric antibodies include antigen-binding fragments thereof.

In some embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13: 1619-1633 (2008), and are further described, e.g., in Riechmann et al., *Nature* 332: 323-329 (1988); Queen et al., *Proc. Nat'l Acad. Sci. USA* 86: 10029-10033 (1989); U.S. Pat. Nos. 5,821,337, 7,527,791, 6,982,321, and 7,087,409; Kashmiri et al., *Methods* 36: 25-34 (2005) (describing SDR (a-CDR) grafting); Padlan, *Mol. Immunol.* 28: 489-498 (1991) (describing "resurfacing"); Dall'Acqua et al., *Methods* 36: 43-60 (2005) (describing "FR shuffling"); and Osbourn et al., *Methods* 36: 61-68 (2005) and Klimka et al., *Br. J. Cancer,* 83: 252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151: 2296 (1993)); framework regions derived from the consensus sequence of human antibodies of a particular subgroup of light or heavy chain variable regions (see, e.g., Carter et al. *Proc. Natl. Acad. Sci. USA*, 89: 4285 (1992); and Presta et al. *J. Immunol.*, 151: 2623 (1993)); human mature (somatically mutated) framework regions or human germline framework regions (see, e.g., Almagro and Fransson, *Front. Biosci.* 13: 1619-1633 (2008)); and framework regions derived from screening FR libraries (see, e.g., Baca et al., *J. Biol. Chem.* 272: 10678-10684 (1997) and Rosok et al., *J. Biol. Chem.* 271: 22611-22618 (1996)).

In some embodiments, the second antigen binding portion of the anti-PD-L1/anti-LAG-3 multiple antigen binding protein or antigen binding fragment thereof is modified, such as humanized, without diminishing the native affinity of the domain for antigen and while reducing its immunogenicity with respect to a heterologous species. For example, the amino acid residues of the antibody variable domain ($V_HH$) of an llama antibody can be determined, and one or more of the Camelid amino acids, for example, in the framework regions, are replaced by their human counterpart as found in the human consensus sequence, without that polypeptide losing its typical character, i.e. the humanization does not significantly affect the antigen binding capacity of the resulting polypeptide. Humanization of Camelid single-domain antibodies requires the introduction and mutagenesis of a limited amount of amino acids in a single polypeptide chain. This is in contrast to humanization of scFv, Fab', (Fab')$_2$ and IgG, which requires the introduction of amino acid changes in two chains, the light and the heavy chain and the preservation of the assembly of both chains.

Single-domain antibodies comprising a $V_HH$ domain can be humanized to have human-like sequences. In some embodiments, the FR regions of the $V_HH$ domain used herein comprise at least about any one of 50%, 60%, 70%, 80%, 90%, 95% or more of amino acid sequence homology to human $V_H$ framework regions. One exemplary class of humanized $V_HH$ domains is characterized in that the $V_HH$s carry an amino acid from the group consisting of glycine, alanine, valine, leucine, isoleucine, proline, phenylalanine, tyrosine, tryptophan, methionine, serine, threonine, asparagine, or glutamine at position 45, such as, for example, L45 and a tryptophan at position 103, according to the Kabat numbering. As such, polypeptides belonging to this class show a high amino acid sequence homology to human $V_H$ framework regions and said polypeptides might be administered to a human directly without expectation of an unwanted immune response therefrom, and without the burden of further humanization.

Another exemplary class of humanized Camelid single-domain antibodies has been described in WO 03/035694 and contains hydrophobic FR2 residues typically found in conventional antibodies of human origin or from other species, but compensating this loss in hydrophilicity by the charged arginine residue on position 103 that substitutes the conserved tryptophan residue present in $V_H$ from double-chain antibodies. As such, peptides belonging to these two classes show a high amino acid sequence homology to human $V_H$ framework regions and said peptides might be administered to a human directly without expectation of an unwanted immune response therefrom, and without the burden of further humanization.

Human Antibodies

In some embodiments, the anti-PD-L1/anti-LAG-3 multiple antigen binding protein or antigen binding fragment thereof provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20: 450-459 (2008). Transgenic mice or rats capable of producing fully human single-domain antibodies are known in the art. See, e.g., US20090307787A1, U.S. Pat. No. 8,754,287, US20150289489A1, US20100122358A1, and WO2004049794.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23: 1117-1125 (2005). See also, e.g., U.S. Pat. Nos. 6,075,181 and 6,150,584 describing XENO-MOUSE™ technology; U.S. Pat. No. 5,770,429 describing HuMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991).) Human antibodies generated via human B-cell hybridoma technology are also described in Li et al., *Proc. Natl. Acad. Sci. USA*, 103: 3557-3562 (2006). Additional methods include those described, for example, in U.S. Pat. No. 7,189,826 (describing production of monoclonal human IgM antibodies from hybridoma cell lines) and Ni, *Xiandai Mianyixue*, 26(4): 265-268 (2006) (describing human-human hybridomas). Human hybridoma technology (Trioma technology) is also described in Vollmers and Brandlein, *Histology and Histopathology*, 20(3): 927-937 (2005) and Vollmers and Brandlein, *Methods and Findings in Experimental and Clinical Pharmacology*, 27(3): 185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

One technique for obtaining $V_HH$ sequences directed against a particular antigen or target involves suitably immunizing a transgenic mammal that is capable of expressing heavy chain antibodies (i.e. so as to raise an immune response and/or heavy chain antibodies directed against said antigen or target), obtaining a suitable biological sample from said transgenic mammal that contains (nucleic acid sequences encoding) said $V_HH$ sequences (such as a blood sample, serum sample or sample of B-cells), and then generating $V_HH$ sequences directed against said antigen or target, starting from said sample, using any suitable technique known per se (such as any of the methods described herein or a hybridoma technique). For example, for this purpose, the heavy chain antibody-expressing mice and the further methods and techniques described in WO 02/085945, WO 04/049794 and WO 06/008548 and Janssens et al., Proc. Natl. Acad. Sci. USA. 2006 Oct. 10; 103(41): 15130-5 can be used. For example, such heavy chain antibody expressing mice can express heavy chain antibodies with any suitable (single) variable domain, such as (single) variable domains from natural sources (e.g. human (single) variable domains, Camelid (single) variable domains or shark (single) variable domains), as well as for example synthetic or semi-synthetic (single) variable domains.

Library-Derived Antibodies

Antibodies of the present application may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348: 552-554; Clackson et al., *Nature* 352: 624-628 (1991); Marks et al., *J. Mol. Biol.* 222: 581-597 (1992); Marks and Bradbury, in Methods in *Molecular Biology* 248: 161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004). Methods for constructing single-domain antibody libraries have been described, for example, see U.S. Pat. No. 7,371,849.

In certain phage display methods, repertoires of $V_H$ and $V_L$ genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al., *EMBO J,* 12: 725-734 (1993). Finally, naive libraries can also be made synthetically by cloning unrearranged V-gene segments from stem cells and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

Anti-PD-L1/Anti-LAG-3 Multiple Antigen Binding Protein or Antigen Binding Fragment Thereof Variants In some embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleic acid sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, Deletion and Variants

In some embodiments, antibody variants having one or more amino acid substitutions are provided. Sites of interest for substitutional mutagenesis include the HVRs and FRs. Conservative substitutions are shown in Table 2 under the heading of "Preferred substitutions." More substantial changes are provided in Table 2 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 2

| Amino acid substitutions | | |
|---|---|---|
| Original Residue | Exemplary Substitutions | Preferred Substitutions |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.
Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207: 179-196 (2008)), and/or SDRs (a-CDRs), with the resulting variant $V_H$ or $V_L$ being tested for binding affinity. Affinity maturation by constructing and reselecting from secondary libraries has been described, e.g., in Hoogenboom et al. in *Methods in Molecular Biology* 178: 1-37 (O'Brien et al., ed., Human Press, Totowa, N.J., (2001)). In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In some embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or CDRs. In some embodiments of the variant $V_HH$ sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244: 1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

b) Glycosylation Variants

In some embodiments, an anti-PD-L1/anti-LAG-3 multiple antigen binding protein or antigen binding fragment thereof provided herein is altered to increase or decrease the extent to which the construct is glycosylated. Addition or deletion of glycosylation sites to an antibody may be conveniently accomplished by altering the amino acid sequence such that one or more glycosylation sites is created or removed.

Where the anti-PD-L1/anti-LAG-3 multiple antigen binding protein or antigen binding fragment thereof comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15: 26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an anti-PD-L1/anti-LAG-3 multiple antigen binding protein or antigen binding fragment thereof of the present application may be made in order to create antibody variants with certain improved properties.

In some embodiments, anti-PD-L1/anti-LAG-3 multiple antigen binding protein variants variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g., complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336: 1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249: 533-545 (1986); US Patent Application No. US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.,* 94(4): 680-688 (2006); and WO2003/085107).

Anti-PD-L1/anti-LAG-3 multiple antigen binding protein variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In some embodiments, one or more amino acid modifications may be introduced into the Fc region of the anti-PD-L1/anti-LAG-3 multiple antigen binding protein or antigen binding fragment thereof provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In some embodiments, the present application contemplates an anti-PD-L1/anti-LAG-3 multiple antigen binding protein variant that possesses some but not all effector functions, which make it a desirable candidate for applications in which the half-life of the anti-PD-L1/anti-LAG-3 multiple antigen binding protein or antigen binding fragment thereof in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity) but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9: 457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83: 7059-7063 (1986)) and Hellstrom, I et al., *Proc. Nat'l Acad. Sci. USA* 82: 1499-1502 (1985); U.S. Pat. No. 5,821,337 (see Bruggemann, M. et al., *J. Exp. Med.* 166: 1351-1361 (1987)). Alternatively, non-radioactive assays methods may be employed (see, for example, ACTI™ non-radioactive cytotoxicity assay for flow cytometry (Cell Technology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95: 652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202: 163 (1996); Cragg, M. S. et al., *Blood* 101: 1045-1052 (2003); and Cragg, M. S. and M. J. Glennie, *Blood* 103: 2738-2743 (2004)). FcRn binding and in vivo clearance/half-life determinations can also be performed using methods known in the art (see, e.g., Petkova, S. B. et al., *Int'l. Immunol.* 18(12): 1759-1769 (2006)).

Anti-PD-L1/anti-LAG-3 multiple antigen binding protein or antigen binding fragment with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain anti-PD-L1/anti-LAG-3 multiple antigen binding protein variants with improved or diminished binding to FcRs are described. (See, e.g., U.S. Pat. No. 6,737,056; WO 2004/056312, and Shields et al., *J. Biol. Chem.* 9(2): 6591-6604 (2001)).

In some embodiments, an anti-PD-L1/anti-LAG-3 multiple antigen binding protein variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

In some embodiments, there is provided an anti-PD-L1/anti-LAG-3 multiple antigen binding protein (e.g., a HCAb) variant comprising a variant Fc region comprising one or more amino acid substitutions which increase half-life and/or improve binding to the neonatal Fc receptor (FcRn). Antibodies with increased half-lives and improved binding to the neonatal Fc receptor (FcRn), which is responsible for the transfer of maternal IgGs to the fetus (Guyer et al., *J. Immunol.* 117: 587 (1976) and Kim et al., *J. Immunol.* 24: 249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, Nature 322:738-40 (1988); U.S. Pat. Nos. 5,648,260; 5,624,821; and WO 94/29351 concerning other examples of Fc region variants.

d) Cysteine Engineered Antibody Variants

In some embodiments, it may be desirable to create cysteine engineered anti-PD-L1/anti-LAG-3 multiple antigen binding proteins or antigen binding fragments thereof, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In some embodiments, any one or more of the following residues may be substituted with cysteine: A118 (EU numbering) of the heavy chain; and S400 (EU numbering) of the heavy chain Fc region. Cysteine engineered anti-PD-L1 constructs may be generated as described, e.g., in U.S. Pat. No. 7,521,541.

e) Antibody Derivatives

In some embodiments, an anti-PD-L1/anti-LAG-3 multiple antigen binding protein or antigen binding fragment thereof provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In some embodiments, conjugates of an anti-PD-L1/anti-LAG-3 multiple antigen binding protein or antigen binding fragment thereof and nonproteinaceous moiety that may be selectively heated by exposure to radiation are provided. In some embodiments, the nonproteinaceous moiety is a carbon nanotube (Kam et al., Proc. Natl. Acad. Sci. USA 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

In some embodiments, an anti-PD-L1/anti-LAG-3 multiple antigen binding protein or antigen binding fragment thereof provided herein may be further modified to contain one or more biologically active protein, polypeptides or fragments thereof. "Bioactive" or "biologically active" as used herein means showing biological activity in the body to carry out a specific function. For example, it may mean the combination with a particular biomolecule such as protein, DNA, etc., and then promotion or inhibition of the activity of such biomolecule. In some embodiments, the bioactive protein or fragments thereof have immunostimulatory/immunoregulatory, membrane transport, or enzymatic activities.

In some embodiments, the bioactive protein or fragments thereof that can be fused with the anti-PD-L1/anti-LAG-3 multiple antigen binding protein or antigen binding fragment thereof described herein is a ligand, such as lymphokines and cellular factors which interact with specific cellular receptor. Lymphokines are low molecular weight proteins which are secreted by T cells when antigens or lectins stimulate T cell growth. Examples of lymphokines include, but are not limited to, interferon-$\alpha$, interferon-$\gamma$, interleukin-1 (IL-1), interleukin-2 (IL-2), interleukin-3 (IL-3), tumor necrosis factor (TNF), a colony stimulating factor (e.g. CSF-1, G-CSF or GM-CSF), chemotaxins, macrophage migration inhibitory factor (MIF), macrophage-activating factor (MAF), NK cell activating factor, T cell replacing factor, leukocyte-inhibitory factor (LIF), lymphotoxins, osteoclast-activating factor (OAF), soluble immune response suppressor (SIRS), growth-stimulating factor, monocyte growth factor, etc. Cellular factors which may be incorporated into the anti-PD-L1/anti-LAG-3 multiple antigen binding proteins or antigen binding fragments thereof include but are not limited to tumor necrosis factor $\alpha$ (TNF$\alpha$), interferons (IFNs), and nerve growth factor (NGF), etc.

III. Pharmaceutical Compositions

Further provided by the present application are pharmaceutical compositions comprising the anti-PD-L1/anti-LAG-3 multiple antigen binding proteins or antigen binding fragments thereof, and optionally a pharmaceutically acceptable carrier. Pharmaceutical compositions can be prepared by mixing an anti-PD-L1/anti-LAG-3 multiple antigen binding protein or antigen binding fragment thereof having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions.

The pharmaceutical composition is preferably to be stable, in which the anti-PD-L1/anti-LAG-3 multiple antigen binding protein or antigen binding fragment thereof described here essentially retains its physical and chemical stability and integrity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993). Stability can be measured at a selected temperature for a selected time period. For rapid screening, the formulation may be kept at 40° C. for 2 weeks to 1 month, at which time stability is measured. Where the formulation is to be stored at 2-8° C., generally the formulation should be stable at 30° C. or 40° C. for at least 1 month, and/or stable at 2-8° C. for at least 2 years. Where the formulation is to be stored at 30° C., generally the formulation should be stable for at least 2 years at 30° C., and/or stable at 40° C. for at least 6 months. For example, the extent of aggregation during storage can be used as an indicator of protein stability. In some embodiments, the stable formulation of an anti-PD-L1/anti-LAG-3 multiple antigen binding protein or antigen binding fragment thereof described herein may comprise less than about 10% (preferably less than about 5%) of the anti-PD-L1/anti-LAG-3 multiple antigen binding protein or antigen binding fragment thereof present as an aggregate in the formulation.

Acceptable carriers, excipients, or stabilizers are nontoxic to recipients at the dosages and concentrations employed, and include buffers, antioxidants including ascorbic acid, methionine, Vitamin E, sodium metabisulfite; preservatives, isotonicifiers (e.g. sodium chloride), stabilizers, metal complexes (e.g. Zn-protein complexes); chelating agents such as EDTA and/or non-ionic surfactants.

In order for the pharmaceutical compositions to be used for in vivo administration, they must be sterile. The pharmaceutical composition may be rendered sterile by filtration through sterile filtration membranes. The pharmaceutical compositions herein generally are placed into a container having a sterile access port, for example, an intravenous solution bag or vial having a stopper pierceable by a hypodermic injection needle.

The route of administration is in accordance with known and accepted methods, such as by single or multiple bolus or infusion over a long period of time in a suitable manner, e.g., injection or infusion by subcutaneous, intravenous, intraperitoneal, intramuscular, intra-arterial, intralesional or intraarticular routes, topical administration, inhalation or by sustained release or extended-release means. In some embodiments, the pharmaceutical composition is administered locally, such as intratumorally.

Sustained-release preparations may be prepared. Suitable examples of sustained-release preparations include semipermeable matrices of solid hydrophobic polymers containing the antagonist, which matrices are in the form of shaped articles, e.g. films, or microcapsules.

The pharmaceutical compositions herein may also contain more than one active compound as necessary for the particular indication being treated, preferably those with complementary activities that do not adversely affect each other. Alternatively, or in addition, the composition may comprise a cytotoxic agent, chemotherapeutic agent, cytokine, immunosuppressive agent, or growth inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 18th edition.

In some embodiments, the pharmaceutical composition is contained in a single-use vial, such as a single-use sealed vial. In some embodiments, the pharmaceutical composition is contained in a multi-use vial. In some embodiments, the pharmaceutical composition is contained in bulk in a container. In some embodiments, the pharmaceutical composition is cryopreserved.

IV. Methods of Use

The anti-PD-L1/anti-LAG-3 multiple antigen binding protein or antigen binding fragment thereof described herein, and the compositions (such as pharmaceutical compositions) thereof are useful for a variety of applications, such as in diagnosis, molecular assays, and therapy.

One aspect of the invention provides a method of treating a PD-L1 and/or a LAG-3 related disease or a condition in a subject in need thereof, comprising administering to the subject an effective amount of a pharmaceutical composition comprising the anti-PD-L1/anti-LAG-3 multiple antigen binding protein or antigen binding fragment thereof described herein. In some embodiments, the PD-L1 and/or LAG-3 related disease is cancer. In some embodiments, the PD-L1 related disease is pathogenic infection, such as viral infection.

The present invention contemplates, in part, protein constructs (such as an anti-PD-L1/anti-LAG-3 multiple antigen binding protein or antigen binding fragment thereof), nucleic acid molecules and/or vectors encoding thereof, host cells comprising nucleic acid molecules and/or vectors encoding thereof, that can be administered either alone or in any combination with another therapy, and in at least some aspects, together with a pharmaceutically acceptable carrier or excipient. In some embodiments, prior to administration of the anti-PD-L1/anti-LAG-3 multiple antigen binding protein or antigen binding fragment thereof, they may be combined with suitable pharmaceutical carriers and excipients that are well known in the art. The compositions prepared according to the disclosure can be used for the treatment or delaying of worsening of cancer.

In some embodiments, there is provided a method of treating cancer comprising administering to the subject an effective amount of a pharmaceutical composition comprising an isolated anti-PD-L1/anti-LAG-3 multiple antigen binding protein or antigen binding fragment thereof. In some embodiments, the cancer is a solid tumor (such as colon cancer).

In some embodiments, the pharmaceutical composition is administered systemically (such as intravenously). In some embodiments, the pharmaceutical composition is administered locally (such as intratumorally). In some embodiments, the method further comprises administering to the subject an additional cancer therapy (such as surgery, radiation, chemotherapy, immunotherapy, hormone therapy, or a combination thereof). In some embodiments, the subject is a human. In some embodiments, the method of treating cancer has one or more of the following biological activities: (1) killing cancer cells (including bystander killing); (2) inhibiting proliferation of cancer cells; (3) inducing immune response in a tumor; (4) reducing tumor size; (5) alleviating one or more symptoms in an individual having cancer; (6) inhibiting tumor metastasis; (7) prolonging survival; (8) prolonging time to cancer progression; and (9) preventing, inhibiting, or reducing the likelihood of the recurrence of a cancer. In some embodiments, the method of killing cancer cells mediated by the pharmaceutical composition described herein can achieve a tumor cell death rate of at least about any of 40%, 50%, 60%, 70%, 80%, 90%, 95%, or more. In some embodiments, the method of killing cancer cells mediated by the pharmaceutical composition described herein can achieve a bystander tumor cell (uninfected by the oncolytic VV) death rate of at least about any of 10%, 20%, 30%, 40%, 50%, 60%, 70%, 80%, 90%, 95%, or more. In some embodiments, the method of reducing tumor size mediated by the pharmaceutical composition described herein can reduce at least about 10% (including for example at least about any of 20%, 30%, 40%, 60%, 70%, 80%, 90%, or 100%) of the tumor size. In some embodiments, the method of inhibiting tumor metastasis mediated by the pharmaceutical composition described herein can inhibit at least about 10% (including for example at least about any of 20%, 30%, 40%, 60%, 70%, 80%, 90%, or 100%) of the metastasis. In some embodiments, the method of prolonging survival of an individual (such as a human) mediated by the pharmaceutical composition described herein can prolongs the survival of the individual by at least any of 1, 2, 3, 4, 5, 6, 7, 8, 9, 10, 11, 12, 18, or 24 months. In some embodiments, the method of prolonging time to cancer progression mediated by the pharmaceutical composition described herein can prolongs the time to cancer progression by at least any of 1, 2, 3, 4, 5, 6, 7, 8, 9, 10, 11, or 12 weeks.

The methods described herein are suitable for treating a variety of cancers, including both solid cancer and liquid cancer. The methods are applicable to cancers of all stages, including early stage cancer, non-metastatic cancer, primary cancer, advanced cancer, locally advanced cancer, metastatic cancer, or cancer in remission. The methods described herein may be used as a first therapy, second therapy, third therapy, or combination therapy with other types of cancer therapies known in the art, such as chemotherapy, surgery, hormone therapy, radiation, gene therapy, immunotherapy (such as T-cell therapy), bone marrow transplantation, stem cell transplantation, targeted therapy, cryotherapy, ultrasound therapy, photodynamic therapy, radio-frequency ablation or the like, in an adjuvant setting or a neoadjuvant setting (i.e., the method may be carried out before the primary/definitive therapy). In some embodiments, the method is used to treat a subject who has previously been treated. In some embodiments, the cancer has been refractory to prior therapy. In some embodiments, the method is used to treat a subject who has not previously been treated.

In some embodiments, the method is suitable for treating cancers with aberrant PD-L1 and/or LAG-3 expression, activity and/or signaling include, by way of non-limiting example, melanoma, prostate cancer, lung cancer, colon cancer, gastric cancer, ovarian cancer, breast cancer, glioblastoma, leukemia, lymphoma, and myeloma.

Thus, in some embodiments, there is provided a method of treating an immunotherapy-responsive solid tumor (such as carcinoma or adenocarcinoma, such as cancers with aberrant PD-L1 and/or LAG-3 expression, activity and/or signaling), comprising administering to the subject an effective amount of a pharmaceutical composition comprising an isolated anti-PD-L1/anti-LAG-3 multiple antigen binding protein or antigen binding fragment thereof. In some embodiments, the cancer is a solid tumor (such as colon cancer).

In some embodiments, the method is suitable for treating cancers with aberrant PD-1 or PD-L1/PD-L2 and/or LAG-3 expression, activity and/or signaling include, by way of non-limiting example, solid tumors. Some cancers whose growth may be inhibited using the antibodies of the invention include cancers typically responsive to immunotherapy. Non-limiting examples of other cancers for treatment include melanoma (e.g., metastatic malignant melanoma), renal cancer (e.g. clear cell carcinoma), prostate cancer (e.g. hormone refractory prostate adenocarcinoma), breast cancer, colon cancer and lung cancer (e.g. non-small cell lung cancer). Additionally, the invention includes refractory or recurrent malignancies whose growth may be inhibited using the antibodies of the invention. Examples of other cancers that may be treated using the antibodies of the invention include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The present invention is also useful for treatment of metastatic cancers, especially metastatic cancers that express PD-L1 (Iwai et al. (2005) *Int. Immunol.* 17: 133-144).

In certain embodiments, disclosed anti-PD-L1/anti-LAG-3 multiple antigen binding proteins may be used as therapeutic agents. Such agents may be employed to diagnose, prognose, monitor, treat, alleviate, and/or prevent a disease or pathology associated with aberrant PD-L1 and/or LAG-3 expression, activity and/or signaling in a subject. A therapeutic regimen is carried out by identifying a subject, e.g., a human patient suffering from (or at risk of developing) a disease or disorder associated with aberrant PD-L1 and/or LAG-3 expression, activity and/or signaling, e.g., a cancer or other neoplastic disorder, using standard methods. An antibody preparation, preferably one having high specificity and high affinity for its target antigen, is administered to the subject and will generally have an effect due to its binding with the target. Administration of the antibody may abrogate or inhibit or interfere with the expression, activity and/or signaling function of the target (e.g., PD-L1 and/or LAG-3). Administration of the anti-PD-L1/anti-LAG-3 multiple antigen binding proteins may abrogate or inhibit or interfere with the binding of the target (e.g., PD-L1 and/or LAG-3) with an endogenous ligand (e.g., PD-1 and/or Class II MHC) to which it naturally binds. For example, the antibody binds to the target and modulates, blocks, inhibits, reduces, antagonizes, neutralizes, or otherwise interferes with PD-L1 and/or LAG-3 expression, activity and/or signaling.

Dosages and desired drug concentrations of pharmaceutical compositions of the present application may vary depending on the particular use envisioned. The determination of the appropriate dosage or route of administration is well within the skill of an ordinary artisan. Animal experiments provide reliable guidance for the determination of effective doses for human therapy. Interspecies scaling of effective doses can be performed following the principles laid down by Mordenti, J. and Chappell, W. "The Use of Interspecies Scaling in Toxicokinetics," In *Toxicokinetics and New Drug Development*, Yacobi et al., Eds, Pergamon Press, New York 1989, pp. 42-46.

The pharmaceutical compositions of the present application, including but not limited to reconstituted and liquid formulations, are administered to a subject in need of treatment with the anti-PD-L1/anti-LAG-3 multiple antigen binding protein or antigen binding fragment thereof described herein, preferably a human, in accord with known methods, such as intravenous administration as a bolus or by continuous infusion over a period of time, by intramuscular, intraperitoneal, intracerobrospinal, subcutaneous, intravenous (i.v.), intra-articular, intrasynovial, intrathecal, oral, topical, or inhalation routes. A reconstituted formulation can be prepared by dissolving a lyophilized anti-PD-L1/anti-LAG3 multiple antigen binding protein or antigen binding fragment thereof described herein in a diluent such that the protein is dispersed throughout. Exemplary pharmaceutically acceptable (safe and non-toxic for administration to a human) diluents suitable for use in the present application include, but are not limited to, sterile water, bacteriostatic water for injection (BWFI), a pH buffered solution (e.g. phosphate-buffered saline), sterile saline solution, Ringer's solution or dextrose solution, or aqueous solutions of salts and/or buffers.

In some embodiments, the pharmaceutical compositions are administered to the subject by subcutaneous (i.e. beneath the skin) administration. For such purposes, the pharmaceutical compositions may be injected using a syringe. However, other devices for administration of the pharmaceutical compositions are available such as injection devices; injector pens; auto-injector devices, needleless devices; and subcutaneous patch delivery systems.

In some embodiments, the pharmaceutical compositions are administered to the subject intravenously. In some embodiments, the pharmaceutical composition is administered to a subject by infusion, such as intravenous infusion. Infusion techniques for immunotherapy are known in the art (see, e.g., Rosenberg et al., New Eng. J. of Med. 319: 1676 (1988)).

Methods for the screening for antibodies that possess the desired specificity include, but are not limited to, enzyme linked immunosorbent assay (ELISA) and other immunologically mediated techniques known within the art.

In other embodiments, antibodies directed against PD-L1 and/or LAG-3 may be used in methods known within the art relating to the localization and/or quantitation of PD-L1 and/or LAG-3 (e.g., for use in measuring levels of PD-L1 and/or LAG-3 within appropriate physiological samples, and/or measuring levels of PD-L1 and/or LAG-3 for use in diagnostic methods, for use in imaging the protein, and the like).

In other embodiments, an anti-PD-L1/anti-LAG-3 multiple antigen binding protein can be used to isolate a PD-L1 and/or LAG-3 polypeptide, by standard techniques, such as immunoaffinity, chromatography or immunoprecipitation. Antibodies directed against the PD-L1 protein (or a fragment thereof) and/or LAG-3 protein (or fragment thereof) can be used diagnostically to monitor protein levels in tissue as part of a clinical testing procedure, e.g., to, for example, determine the efficacy of a given treatment regimen.

Detection can be facilitated by coupling (i.e., physically linking) the anti-PD-L1/anti-LAG-3 multiple antigen binding proteins to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include 125I, 131I, 35S or 3H.

In some embodiments, the anti-PD-L1/anti-LAG-3 multiple antigen binding proteins (e.g. antibodies) contains a detectable label. Antibodies may be, for example, polyclonal, or monoclonal. An intact antibody, or a fragment thereof (e.g., Fab, scFv, or F(ab')$_2$) is used. The term "labeled", regarding the probe or antibody, is intended to encompass direct labeling of the probe or antibody by coupling (i.e., physically linking) a detectable substance to the probe or antibody, and indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin.

The term "biological sample" is intended to include tissues, cells and biological fluids isolated from a subject, as well as tissues, cells and fluids present within a subject. Included within the usage of the term "biological sample," therefore, is blood and a fraction or component of blood including blood serum, blood plasma, or lymph. That is, the detection method can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

V. Methods of Preparation

The anti-PD-L1/anti-LAG-3 multiple antigen binding protein or antigen binding fragment thereof described herein may be prepared using any methods known in the art or as described herein. Also see Example 1.

Methods for making multiple antigen binding proteins, e.g., bispecific antibodies, are known in the art.

Traditionally, the recombinant production of bispecific antibodies is based on the co-expression of two immunoglobulin heavy-chain/light-chain pairs, where the two heavy chains have different specificities (Milstein and Cuello, *Nature,* 305: 537-539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., *EMBO J.,* 10: 3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology*, 121: 210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full-length antibodies or antibody fragments (e.g. $F(ab')_2$ bispecific antibodies). Techniques for generating bispecific antibodies from antibody fragments have been described in the literature. For example, bispecific antibodies can be prepared using chemical linkage. Brennan et al., *Science* 229: 81 (1985) describe a procedure in which intact antibodies are proteolytically cleaved to generate $F(ab')_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Additionally, Fab' fragments can be directly recovered from *E. coli* and chemically coupled to form bispecific antibodies. Shalaby et al., *J. Exp. Med.* 175: 217-225 (1992) describe the production of a fully humanized bispecific antibody $F(ab')_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.* 148(5): 1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized to make antibody homodimers. The "diabody" technology described by Hollinger et al., *Proc. Natl. Acad. Sci. USA* 90: 6444-6448 (1993) has provided an alternative mechanism for making bispecific antibody fragments. The fragments comprise a heavy-chain variable domain connected to a light-chain variable domain by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments with single-chain Fv (sFv) dimers has also been reported. Gruber et al., *J. Immunol.* 152: 5368 (1994).

For recombinant production of the bispecific antibodies, the nucleic acids encoding the bispecific antibodies are isolated and inserted into a replicable vector for further cloning (amplification of the DNA) or for expression. DNA encoding the bispecific antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, preferred host cells are of either prokaryotic or eukaryotic (generally mammalian) origin.

VI. Kits and Articles of Manufacture

Further provided are kits, unit dosages, and articles of manufacture comprising any of the anti-PD-L1/anti-LAG-3 multiple antigen binding proteins described herein. In some embodiments, a kit is provided comprising any one of the pharmaceutical compositions described herein and preferably provides instructions for its use.

The kits of the present application are in suitable packaging. Suitable packaging includes, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The article of manufacture can comprise a container and a label or package insert on or associated with the container. Suitable containers include, for example, bottles, vials, syringes etc. The containers may be formed from a variety of materials such as glass or plastic. Generally, the container holds a composition which is effective for treating a disease or disorder described herein and may have a sterile access port (for example the container may be an intravenous solution bag or a vial having a stopper pierceable by a hypodermic injection needle). The label or package insert indicates that the composition is used for treating the particular condition in an individual. The label or package insert will further comprise instructions for administering the composition to the individual. The label may indicate directions for reconstitution and/or use. The container holding the pharmaceutical composition may be a multi-use vial, which allows for repeat administrations (e.g., from 2-6 administrations) of the reconstituted formulation. Package insert refers to instructions customarily included in commercial packages of therapeutic products that contain information about the indications, usage, dosage, administration, contraindications and/or warnings concerning the use of such therapeutic products. Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kits or article of manufacture may include multiple unit doses of the pharmaceutical composition and instructions for use, packages in quantities sufficient for storage and use in pharmacies, for example, hospital pharmacies and compounding pharmacies.

Embodiments

The invention provides also the following non-limiting embodiments.

Embodiment 1 is an isolated anti-PD-L1/anti-LAG-3 multiple antigen binding protein or antigen binding fragment thereof comprising:

(a) a first antigen binding portion comprising a heavy chain variable domain ($V_H$) and a light chain variable domain ($V_L$), wherein the $V_H$ and $V_L$ together form an antigen-binding site that specifically binds PD-L1, and wherein the $V_H$ comprises a heavy chain complementarity determining region 1 (HCDR1), HCDR2, and HCDR3 comprising the amino acid sequences of:
   (i) SEQ ID NO:3, SEQ ID NO:4, and SEQ ID NO:5, respectively, or
   (ii) SEQ ID NO:9, SEQ ID NO:10, and SEQ ID NO:11, respectively; and the $V_L$ comprises a light chain complementarity determining region 1 (LCDR1), LCDR2, and LCDR3 comprising the amino acid sequences of SEQ ID NO:6, SEQ ID NO:7, and SEQ ID NO:8, respectively; and (b) a second antigen binding portion comprising a single-domain antibody that specifically binds LAG-3, wherein the single-domain antibody comprises a complementarity determining region 1 (CDR1), CDR2, and CDR3 comprising the amino acid sequences of SEQ ID NO:33, SEQ ID NO:34, and SEQ ID NO:35, respectively;

wherein the first antigen binding portion and the second antigen binding portion are fused to each other.

Embodiment 2 is the isolated anti-PD-L1/anti-LAG-3 multiple antigen binding protein or antigen binding fragment thereof of embodiment 1, wherein the first antigen binding portion is a full-length antibody comprising two heavy chains and two light chains.

Embodiment 3 is the isolated anti-PD-L1/anti-LAG-3 multiple antigen binding protein or antigen binding fragment thereof of embodiment 1 or 2, wherein the first antigen binding portion is an antibody fragment comprising a heavy chain comprising the $V_H$ and a light chain comprising the $V_L$.

Embodiment 4 is the isolated anti-PD-L1/anti-LAG-3 multiple antigen binding protein or antigen binding fragment thereof of any one of embodiments 1-3, wherein the second antigen binding portion comprises a single polypeptide chain.

Embodiment 5 is the isolated anti-PD-L1/anti-LAG-3 multiple antigen binding protein or antigen binding fragment thereof of embodiment 4, wherein the carboxy (C)-terminus of the second antigen binding portion is fused to the amino (N)-terminus of at least one heavy chain of the first antigen binding portion.

Embodiment 6 is the isolated anti-PD-L1/anti-LAG-3 multiple antigen binding protein or antigen binding fragment thereof of embodiment 4, wherein the carboxy (C)-terminus of the second antigen binding portion is fused to the amino (N)-terminus of at least one light chain of the first antigen binding portion.

Embodiment 7 is the isolated anti-PD-L1/anti-LAG-3 multiple antigen binding protein or antigen binding fragment thereof of embodiment 4, wherein the amino (N)-terminus of the second antigen binding portion is fused to the carboxy (C)-terminus of at least one heavy chain of the first antigen binding portion.

Embodiment 8 is the isolated anti-PD-L1/anti-LAG-3 multiple antigen binding protein or antigen binding fragment thereof of embodiment 4, wherein the amino (N)-terminus of the second antigen binding portion is fused to the carboxy (C)-terminus of at least one light chain of the first antigen binding portion.

Embodiment 9 is the isolated anti-PD-L1/anti-LAG-3 multiple antigen binding protein or antigen binding fragment thereof of any one of embodiments 1-8, wherein the heavy chain of the first antigen binding portion comprises an amino acid sequence at least 95% identical to SEQ ID NO:14 or SEQ ID NO:18, and the light chain of the first antigen binding portion comprises an amino acid sequence at least 95% identical to SEQ ID NO:16.

Embodiment 10 is the isolated anti-PD-L1/anti-LAG-3 multiple antigen binding protein or antigen binding fragment thereof of embodiment 9, wherein the heavy chain of the first antigen binding portion comprises the amino acid sequence of SEQ ID NO:14 or SEQ ID NO:18, and the light chain of the first antigen portion comprises the amino acid sequence of SEQ ID NO:16.

Embodiment 11 is the isolated anti-PD-L1/anti-LAG-3 multiple antigen binding protein or antigen binding fragment thereof of any one of embodiments 1-10, wherein the second antigen binding portion comprises an amino acid sequence at least 95% identical to an amino acid sequence of SEQ ID NO:37.

Embodiment 12 is the isolated anti-PD-L1/anti-LAG-3 multiple antigen binding protein or antigen binding fragment thereof of embodiment 11, wherein the second antigen binding portion comprises the amino acid sequence of SEQ ID NO:37.

Embodiment 13 is the isolated anti-PD-L1/anti-LAG-3 multiple antigen binding protein or antigen binding fragment thereof of any one of embodiments 1-12, wherein the first antigen binding portion comprises a human, humanized or chimeric antibody or antigen binding fragment thereof.

Embodiment 14 is the isolated anti-PD-L1/anti-LAG-3 multiple antigen binding protein or antigen binding fragment thereof of any one of embodiments 1-13, wherein the second antigen binding portion comprising a single-domain antibody that specifically binds LAG-3 is camelid, chimeric, human, partially humanized, or fully humanized.

Embodiment 15 is the isolated anti-PD-L1/anti-LAG-3 multiple antigen binding protein or antigen binding fragment thereof of any one of embodiments 1-14, wherein the first antigen binding portion comprises an Fc region.

Embodiment 16 is the isolated anti-PD-L1/anti-LAG-3 multiple antigen binding protein or antigen binding fragment thereof of embodiment 15, wherein the second antigen binding portion is fused to the N-terminus of the Fc region.

Embodiment 17 is the isolated anti-PD-L1/anti-LAG-3 multiple antigen binding protein or antigen binding fragment thereof of embodiment 15 or 16, wherein the Fc region is an IgG1 Fc.

Embodiment 18 is the isolated anti-PD-L1/anti-LAG-3 multiple antigen binding protein or antigen binding fragment thereof of embodiment 15 or 16, wherein the Fc region is an IgG4 Fc having an S228P mutation and/or an L235E mutation.

Embodiment 19 is the isolated anti-PD-L1/anti-LAG-3 multiple antigen binding protein or antigen binding fragment thereof of any one of embodiments 1-18, wherein the first antigen binding portion and the second antigen binding portion are fused to each other via a peptide bond or a peptide linker.

Embodiment 20 is the isolated anti-PD-L1/anti-LAG-3 multiple antigen binding protein or antigen binding fragment thereof of embodiment 19, wherein the peptide linker comprises an amino acid sequence selected from SEQ ID NO:12, SEQ ID NO:38 or SEQ ID NOs:40-43.

Embodiment 21 is an isolated nucleic acid encoding the isolated anti-PD-L1/anti-LAG-3 multiple antigen binding protein or antigen binding fragment thereof of any one of embodiments 1-20.

Embodiment 22 is an isolated vector comprising the isolated nucleic acid of embodiment 21.

Embodiment 23 is a host cell comprising the isolated vector of embodiment 22.

Embodiment 24 is a pharmaceutical composition comprising the isolated anti-PD-L1/anti-LAG-3 multiple antigen binding protein or antigen binding fragment thereof of any one of embodiments 1-20, and a pharmaceutical acceptable carrier.

Embodiment 25 is a method of treating a subject having or at risk of having a PD-L1 and/or LAG-3-related disease, the method comprising administering to the subject an effective amount of the pharmaceutical composition of embodiment 24.

Embodiment 26 is the method of embodiment 25, wherein the PD-L1 and/or LAG-3-related disease is cancer.

Embodiment 27 is the method of embodiment 26, wherein the cancer is a solid tumor.

Embodiment 28 is the method of embodiment 26 or 27, wherein the cancer is a colon cancer.

Embodiment 29 is the method of any one of embodiments 25-28, further comprising administering to the individual an additional cancer therapy.

Embodiment 30 is the method of embodiment 29, wherein the additional cancer therapy is surgery, radiation, chemotherapy, immunotherapy, hormone therapy, or a combination thereof.

Embodiment 31 is the method of embodiment 25, wherein the PD-L1 related disease is a pathogenic infection.

Embodiment 32 is the method of any one of embodiments 25-31, wherein the pharmaceutical composition is administered systemically or locally.

Embodiment 33 is the method of embodiment 32, wherein the pharmaceutical composition is administered intravenously.

Embodiment 34 is the method of embodiment 32, wherein the pharmaceutical composition is administered intratumorally.

Embodiment 35 is the method of any one of embodiments 25-34, wherein the subject is a human.

EXAMPLES

The examples below are intended to be purely exemplary of the invention and should therefore not be considered to limit the invention in any way. The following examples and detailed description are offered by way of illustration and not by way of limitation.

Example 1: Construction and Expression of Anti-PD-L1/Anti-LAG-3 Single Domain Antibody Fused to Monoclonal Antibody (SMAB)

Based on the single domain antibody fused to monoclonal antibody (SMAB) structure described in WO2018014855A1, a series of anti-PD-L1/anti-LAG-3 bispecific antibodies were created using an anti-PD-L1 monoclonal antibody (mAb) and an anti-LAG-3 single domain antibody (sdAb). The anti-LAG-3 sdAb was fused to two different anti-PD-L1 mAbs including anti-PDL1HCv1 and anti-PDL1HCv5, respectively. The anti-LAG-3 sdAb was located at the amino (N)- or carboxy (C)-terminus of the heavy chain or light chain of the anti-PD-L1 mAb with a linker (E-linker: EPKSSDKTHTSPPSP (SEQ ID NO: 12), G-linker: (G45)3 (SEQ ID NO: 38), E4-linker: ESKYGPPSPPSP (SEQ ID NO: 40) G9-linker: GGGGSGGGS (SEQ ID NO: 41), G12-linker: GGGGSGGGGSGS (SEQ ID NO: 42) or Ea-linker: EPKSSDKGHGGPPGP (SEQ ID NO: 43)) for fusion. Each construct is composed of two identical fusion polypeptide chains and two identical native polypeptide chains, and the DNA sequence expressing each polypeptide chain was inserted into pTT5 vector between EcoRI and HindIII restriction sites. Each plasmid also includes a secretion signal sequence for proteins secreted into the growth medium. The anti-LAG-3 sdAb fused to the N-terminus of the IgG4 Fc portion, comprising the S228P and L235E mutations, was used as a control for an in vitro bioassay. The plasmids expressing the multiple antigen binding proteins are shown below in Table 3.

TABLE 3

| Plasmids expressing anti-PD-L1/anti-LAG3 SMAB proteins | | | |
|---|---|---|---|
| Protein | Component | Plasmid | SEQ ID NO: (amino acid) |
| PDL1HCv1 | H1 | pTT5-PDL1HCv1 | 14 |
| | L1 | pTT5-PDL1LCv1 | 16 |
| PDL1HCv5 | H2 | pTT5-PDL1HCv5 | 18 |
| | L1 | pTT5-PDL1LCv1 | 16 |
| mPDL1LCv1-E-sLAG3-HCv1 | L2 | pTT5-PDL1LCv1-E-LAG3 | 20 |
| | H1 | pTT5-PDL1HCv1 | 14 |
| mPDL1LCv1-E-sLAG3-HCv5 | L2 | pTT5-PDL1LCv1-E-LAG3 | 20 |
| | H2 | pTT5-PDL1HCv5 | 18 |
| sLAG3-E-mPDL1HCv1 | H3 | pTT5-LAG3-E-PDL1HCv1 | 22 |
| | L1 | pTT5-PDL1LCv1 | 16 |
| mPDL1HCv1-E-sLAG3 | H4 | pTT5-PDL1HCv1-E-LAG3 | 24 |
| | L1 | pTT5-PDL1LCv1 | 16 |

TABLE 3-continued

| Plasmids expressing anti-PD-L1/anti-LAG3 SMAB proteins | | | |
| --- | --- | --- | --- |
| Protein | Component | Plasmid | SEQ ID NO: (amino acid) |
| sLAG3-E-mPDL1HCv5 | H5 | pTT5-LAG3-E-PDL1HCv5 | 26 |
|  | L1 | pTT5-PDL1LCv1 | 16 |
| mPDL1HCv5-E-sLAG3 | H6 | pTT5-PDL1HCv5-E-LAG3 | 28 |
|  | L1 | pTT5-PDL1LCv1 | 16 |
| sLAG3-E-mPDL1LCv1-HCv1 | L3 | pTT5-LAG3-E-PDL1LCv1 | 30 |
|  | H1 | pTT5-PDL1HCv1 | 14 |
| sLAG3-E-mPDL1LCv1-HCv5 | L3 | pTT5-LAG3-E-PDL1LCv1 | 30 |
|  | H2 | pTT5-PDL1HCv5 | 18 |
| sdAb-LAG3-IgG4PE | H7 | pTT5-sdAb-LAG3-IgG4PE | 32 |
| mPDL1HCv1-G15-sLAG3 | H8 | pTT5-PDL1HCv1-G15-LAG3 | 45 |
|  | L1 | pTT5-PDL1LCv1 | 16 |
| mPDL1HCv1-G9-sLAG3 | H9 | pTT5-PDL1HCv1-G9-LAG3 | 47 |
|  | L1 | pTT5-PDL1LCv1 | 16 |
| mPDL1HCv1-Ea-sLAG3 | H10 | pTT5-PDL1HCv1-Ea-LAG3 | 49 |
|  | L1 | pTT5-PDL1LCv1 | 16 |
| sLAG3-G12-mPDL1HCv1 | H11 | pTT5-LAG3-G12-PDL1HCv1 | 51 |
|  | L1 | pTT5-PDL1LCv1 | 16 |
| mPDL1LCv1-E4-sLAG3-HCv1 | L4 | pTT5-PDL1LCv1-E4-LAG3 | 53 |
|  | H1 | pTT5-PDL1HCv1 | 14 |
| mPDL1HCv1-E4-sLAG3 | H12 | pTT5-PDL1HCv1-E4-LAG3 | 55 |
|  | L1 | pTT5-PDL1LCv1 | 16 |

CHO-3E7 cells transfected with expression plasmids were cultured at 37° C. and 100 rpm for 6 days. The supernatant fraction was collected by centrifugation and the SMAB protein was purified through Protein A column.

As mentioned above, two different PD-L1 mAbs including PDL1HCv1 and PDL1HCv5 were used for SMAB construction. PDL1HCv1 mAb consists of heavy chain called H1 and light chain called L1, and PDL1HCv5 mAb consists of heavy chain called H2 and the same light chain of L1.

Different SMABs were designed by fusing LAG-3 sdAb to PDL1HCv1 and PDL1HCv5, respectively with E-linker (EPKSSDKTHTSPPSP). LAG-3 sdAb was fused to the C-terminus of light chain of L1 generating new polypeptide called L2. LAG-3 sdAb was fused to the N-terminus of light chain of L1 generating a new polypeptide called L3. Similarly, LAG-3 sdAb was fused to the N-terminus of heavy chain of H1 leading to a new polypeptide called H3; LAG-3 sdAb was fused to the C-terminus of heavy chain of H1 leading to a new polypeptide called H4; LAG-3 sdAb was fused to the N-terminus of heavy chain of H2 leading to a new polypeptide called H5; and LAG-3 sdAb was fused to the C-terminus of heavy chain of H2 leading to a new polypeptide called H6. Meanwhile, other linkers were also used for SMAB construction. LAG-3 sdAb was fused to the C-terminus of heavy chain of H1 by three other linkers of G15-linker, G9-linker or Ea-linker, leading to new polypeptides called H8, H9 and H10, respectively. In addition, LAG-3 sdAb was fused to the N-terminus of heavy chain of H1 by G12-linker leading to a new polypeptide called H11, LAG-3 sdAb was fused to the C-terminus of heavy chain of H1 by E4-linker leading to a new polypeptide called H12 and LAG-3 sdAb was fused to the C-terminus of light chain of L1 by E4-linker generating new polypeptide called L4. Using these new fusion proteins, SMAB of mPDL1LCv1-E-sLAG3-HCv1 was generated by combining new light chain fusion protein of L2 and native heavy chain of H1; SMAB of mPDL1LCv1-E-sLAG3-HCv5 was generated by combining new light chain fusion protein of L2 and native heavy chain of H2; SMAB of sLAG3-E-mPDL1HCv1 was generated by combining new heavy chain fusion protein of H3 and native light chain of L1; SMAB of mPDL1HCv1-E-sLAG3 was generated by combining new heavy chain fusion protein of H4 and native light chain of L1; SMAB of sLAG3-E-mPDL1HCv5 was generated by combining new heavy chain fusion protein of H5 and native light chain of L1; SMAB of mPDL1HCv5-E-sLAG3 was generated by combining new heavy chain fusion protein of H6 and native light chain of L1; SMAB of sLAG3-E-mPDL1LCv1-HCv1 was generated by combining new light chain fusion protein of L3 and native heavy chain of H1; SMAB of sLAG3-E-mPDL1LCv1-HCv5 was generated by combining new light chain fusion protein of L3 and native heavy chain of H2; SMAB of mPDL1HCv1-G15-sLAG3 was generated by combining new heavy chain fusion protein of H8 and native light chain of L1; SMAB of mPDL1HCv1-G9-sLAG3 was generated by combining new heavy chain fusion protein of H9 and native light chain of L1; SMAB of mPDL1HCv1-Ea-sLAG3 was generated by combining new heavy chain fusion protein of H10 and native light chain of L1; SMAB of sLAG3-G12-mPDL1HCv1 was generated by combining new heavy chain fusion protein of H11 and native light chain of L1; SMAB of mPDL1HCv1-E4-sLAG3 was generated by combining new heavy chain fusion protein of H12 and native light chain of L1; and SMAB of mPDL1LCv1-E4-sLAG3-HCv1 was generated by combining new light chain fusion protein of L4 and native heavy chain of H1. The Fc fusion protein of sdAb-LAG3-IgG4PE was constructed by linking anti-LAG-3 sdAb to the N-terminus of human IgG4 Fc portion with sites mutation (S228P and L235E), which is named H7.

TABLE 4

Amino acid sequences of anti-PD-L1 monoclonal antibody moiety

| Anti-PD-L1 | Sequence | SEQ ID NO: |
|---|---|---|
| PDL1HCv1 heavy chain | EVQLVQSGAEVKKPGASVKVSCKASGYIFTGYGITWVRQAPGQGLEWMGEIFPRRVQT YYSEKFKGRVTMTTDTSTSTAYMELRSLRSDDTAVYYCARDYDPYFALDYWGQGTTV TVSSASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKKVEPKSCDKTHTCPPCPAPE LLGGPSVFLFPPKPKDTLMISRTPEVTCVVVDVSHEDPEVKFNWYVDGVEVHNAKTKPR EEQYASTYRVVSVLTVLHQDWLNGKEYKCKVSNKALPAPIEKTISKAKGQPREPQVYTL PPSREEMTKNQVSLTCLVKGFYPSDIAVEWESNGQPENNYKTTPPVLDSDGSFFLYSKLT VDKSRWQQGNVFSCSVMHEALHNHYTQKSLSLSPGK | 14 |
| PDL1HCv1 or PDL1HCv5 light chain | DIQMTQSPSSLSASVGDRVTITCRASQDVSTAVDWYQQKPGKAPKWYSASYRYTGVP DRFSGSGSGTDFTFTISSLQPEDIATYYCQQHYSIPFTFGQGTKLEIKRTVAAPSVFIFPPSD EQLKSGTASVVCLLNNFYPREAKVQWKVDNALQSGNSQESVTEQDSKDSTYSLSSTLTL SKADYEKHKVYACEVTHQGLSSPVTKSFNRGEC | 16 |
| PDL1HCv5 heavy chain | EVQLVQSGAEVKKPGASVKVSCKASGYIFTGYGITWVRQAPGQGLEWMGEIFPRRVQT YYSEKFKGRVTMTADTSTSTAYMELRSLRSDDTAVYYCARDYDPYFALDYWGQGTTV TVSSASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKKVEPKSCDKTHTCPPCPAPE LLGGPSVFLFPPKPKDTLMISRTPEVTCVVVDVSHEDPEVKFNWYVDGVEVHNAKTKPR EEQYASTYRVVSVLTVLHQDWLNGKEYKCKVSNKALPAPIEKTISKAKGQPREPQVYTL PPSREEMTKNQVSLTCLVKGFYPSDIAVEWESNGQPENNYKTTPPVLDSDGSFFLYSKLT VDKSRWQQGNVFSCSVMHEALHNHYTQKSLSLSPGK | 18 |

| | Sequence | SEQ ID NO: | Sequence | SEQ ID NO: | Sequence | SEQ ID NO: |
|---|---|---|---|---|---|---|
| PDL1HCv1 heavy chain CDR | GYIFTGYGIT | 3 | EIFPRRVQTYYSEKFKG | 4 | DYDPYFALDY | 5 |
| PDL1HCv1 or PDL1HCv5 light chain CDR | RASQDVSTAVD | 6 | SASYRYT | 7 | QQHYSIPFT | 8 |
| PDL1HCv5 heavy chain CDR | GYIFTGYGIT | 9 | EIFPRRVQTYYSEKFKG | 10 | DYDPYFALDY | 11 |

TABLE 5

DNA and amino acid (a.a.) sequences of anti-LAG-3 single-domain antibody moiety

| | Sequence | SEQ ID NO: |
|---|---|---|
| Anti-LAG3 sdAb DNA | GAGGTGCAGCTGGTGGAGTCCGGAGGAGGACTGGTGCAGCCAGGAGGCTCCCTGAGGCTG AGCTGCGCCGCTTCTGGCTACACCGTGTCCAGCTATTGTATGGGCTGGTTCAGGCAGGCTC CTGGCAAGGGAAGGGAGGGCGTGTCCGGTATCGACAGCGATGGCAGCGTGTCTTACGCCG ACAGCGTGAAGGGCAGATTCACCATCTCTAAGGATAACTCCAAGAATACACTGTACCTGC AGATGAACTCTCTGCGCGCCGAGGACACCGCCGTGTACTTTTGCGCTGCTGACCTGTGCTG GGTGGACCAGGATCAGGGCGAGTATAATACATGGGGCCAGGGCACCCTGGTGACAGTGTC TTCC | 36 |
| Anti-LAG3 sdAb a.a. | EVQLVESGGGLVQPGGSLRLSCAASGYTVSSYCMGWFRQAPGKGREGVSAIDSDGSVSYA DSVKGRFTISKDNSKNTLYLQMNSLRAEDTAVYFCAADLCWVDQDQGEYNTWGQGTLVT VSS | 37 |

| | Sequence | SEQ ID NO: | Sequence | SEQ ID NO: | Sequence | SEQ ID NO: |
|---|---|---|---|---|---|---|
| Anti-LAG3 sdAb CDR a.a. | GYTVSSYCMG | 33 | AIDSDGSVSYADSVKG | 34 | DLCWVDQDQGEYNT | 35 |

TABLE 6

| | Sequence | SEQ ID NO: |
|---|---|---|
| DNA and amino acid (a.a.) sequences of secretory signal sequence, linker sequences, and IgG4 Fc sequence | | |
| Secretory Signal Peptide DNA | ATGGGCTGGTCCTGCATCATCCTGTTCCTGGTGGCTACCGCCACCGGCGTGCACTCC | 1 |
| Secretory Signal Peptide a.a. | MGWSCIILFLVATATGVHS | 2 |
| E-Linker a.a. | EPKSSDKTHTSPPSP | 12 |
| G-Linker a.a. | GGGGSGGGGSGGGGS | 38 |
| E4-linker a.a | ESKYGPPSPPSP | 40 |
| G9-linker a.a | GGGGSGGGS | 41 |
| G12-linker a.a | GGGGSGGGGSGS | 42 |
| Ea-linker a.a | EPKSSDKGHGGPPGP | 43 |
| IgG4 Fc a.a. | ESKYGPPCPPCPAPEFEGGPSVFLFPPPKPKDTLMISRTPEVTCVVVDVSQEDPEVQFNWY VDGVEVHNAKTKPREEQFNSTYRVVSVLTVLHQDWLNGKEYKCKVSNKGLPSSIEKTI SKAKGQPREPQVYTLPPSQEEMTKNQVSLTCLVKGFYPSDIAVEWESNGQPENNYKTTP PVLDSDGSFFLYSRLTVDKSRWQEGNVFSCSVMHEALHNHYTQKSLSLSLGK | 39 |

Example 2: In Vitro Activity of Anti-PD-L1/Anti-LAG-3 Single Domain Antibody Fused to Monoclonal Antibody (Smab)

Facs Binding Assay

The binding pattern of bispecific antibodies on PD-L1 or LAG-3 expressed on CHO-K1 cells were plotted with antibody in 3× serial dilutions, starting concentration of 300 nM. Antibody-antigen binding curves were generated with geometric mean values. Raw data was plotted with Graph-Pad Prism v6.02 software with four parameters, best-fit values program to analyze the EC50.

Figure 5:
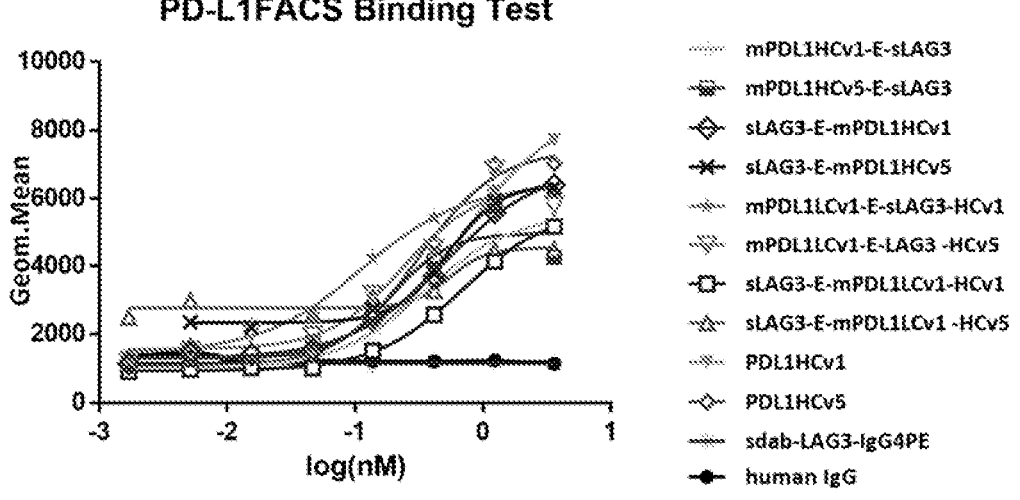
FIG. 5 depicts the results of a FACS binding assay using CHO-K1 cells expressing PD-L1.

For PD-L1 binding, when LAG-3 sdAb is fused to the C-terminus of light chain of PD-L1 mAb by E-linker, the final constructs including mPDL1LCv1-E-sLAG3-HCv1 and mPDL1LCv1-E-sLAG3-HCv5 have higher affinity to PD-L1 antigen compared to controls of PDL1HCv1 and PDL1HCv5 (FIG. 5). When LAG-3 sdAb is fused to the C-terminus of heavy chain of PD-L1 mAb by E-linker, the final constructs have similar affinity to PD-L1 antigen compared to controls of PDL1HCv1 and PDL1HCv5 (FIG. 5). However, when LAG-3 sdAb is fused to the N-terminus of heavy/light chain of PD-L1 mAb, the final constructs have a little lower affinity to PD-L1 antigen compared to controls (FIG. 5).

Figure 9:
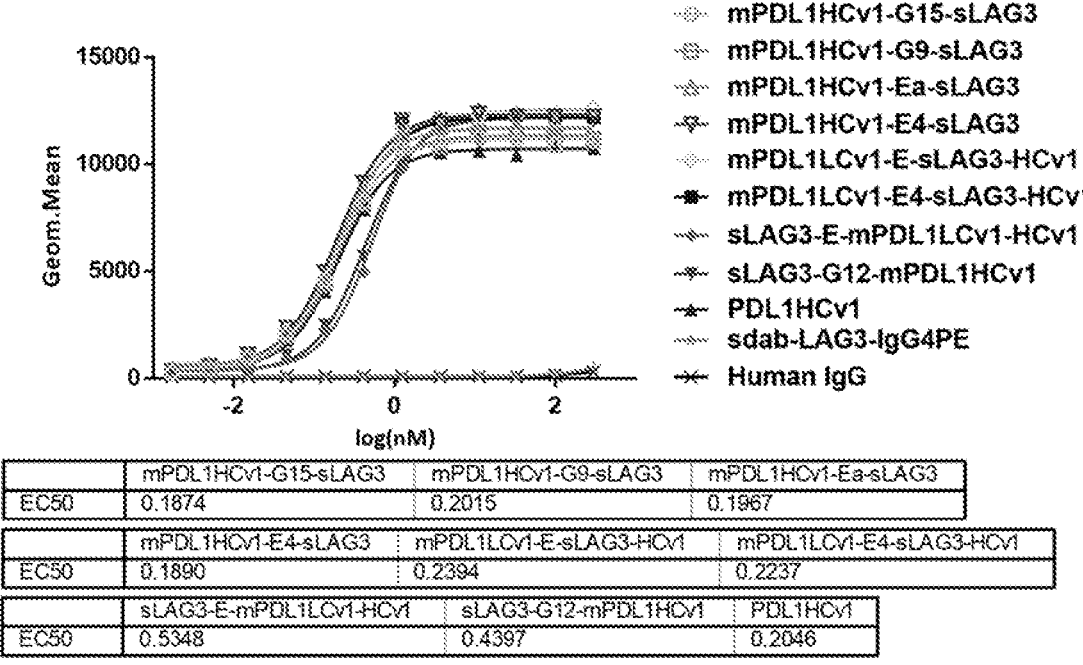
FIG. 9 depicts the results of a FACS binding assay using CHO-K1 cells expressing PD-L1.

When the other linkers are used for SMAB construction, SMABs showed similar binding affinity to PD-L1 compared to control of PDL1HCv1 mAb (FIG. 9).

Figure 10:
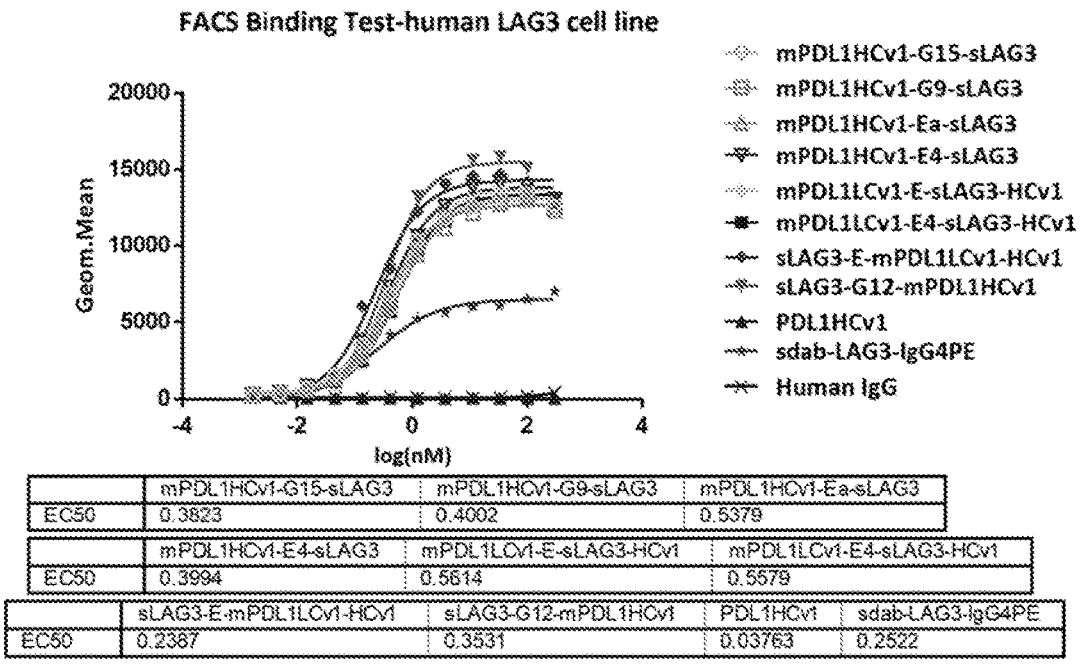
FIG. 10 depicts the results of a FACS binding assay using CHO-K1 cells expressing LAG-3.

For LAG-3 binding, as showed in FIG. 6 and FIG. 10, all of SMAB constructs showed much higher affinity to LAG-3 antigen compared to the control of Fc fusion protein of sdAb-LAG3-IgG4PE.

In Vitro Bioassay

A multiple antigen binding protein can bind to two target antigens, evaluating its synergistic effect is more challenging than checking the response by single antigen targeting. For the in vitro bioassay of anti-PD-L1/anti-LAG3 multiple antigen binding proteins, PD-1/PD-L1 and LAG-3 blockade bioassay were performed individually using Promega detection kits since there is no such assay system to detect both of PD-1/PD-L1 and LAG-3 blockade.

PD-1/PD-L1 Blockade Bioassay

The PD-1/PD-L1 blockade bioassay system from Promega (Madison, Wis.) can be used to measure the potency and stability of antibodies and other biologics designed to block the PD-1/PD-L1 interaction. The assay consists of two genetically engineered cell lines: PD-1 effector cells, which are Jurkat T cells expressing human PD-1 and a luciferase reporter driven by an NFAT response element (NFAT-RE), and PD-L1 aAPC/CHO-K1 Cells, which are CHO-K1 cells expressing human PD-L1 and an engineered cell surface protein designed to activate cognate TCRs in an antigen-independent manner. When the two cell types are co-cultured, the PD-1/PD-L1 interaction inhibits TCR signaling and NFAT-RE-mediated luminescence. Addition of either an anti-PD-1 or anti-PD-L1 antibody that blocks the PD-1/PD-L1 interaction releases the inhibitory signal and results in TCR activation and NFAT-RE-mediated luminescence.

The LAG-3 Blockade Bioassay works similarly and was used for detection of LAG-3 antibody. The assay consists of two genetically engineered cell lines: LAG-3 effector cells, which are Jurkat T cells expressing human LAG-3 and a luciferase reporter driven by a response element, and MHC II/Raji cells, which are Raji cells expressing human MHC II. When the two cell types are co-cultured, the LAG-3/MHC II interaction inhibits T-cell signaling and luminescence response. Addition of anti-LAG-3 antibody that blocks the LAG-3/MHC II interaction releases the inhibitory signal and results in T-cell activation and luminescence expression.

Figure 11:
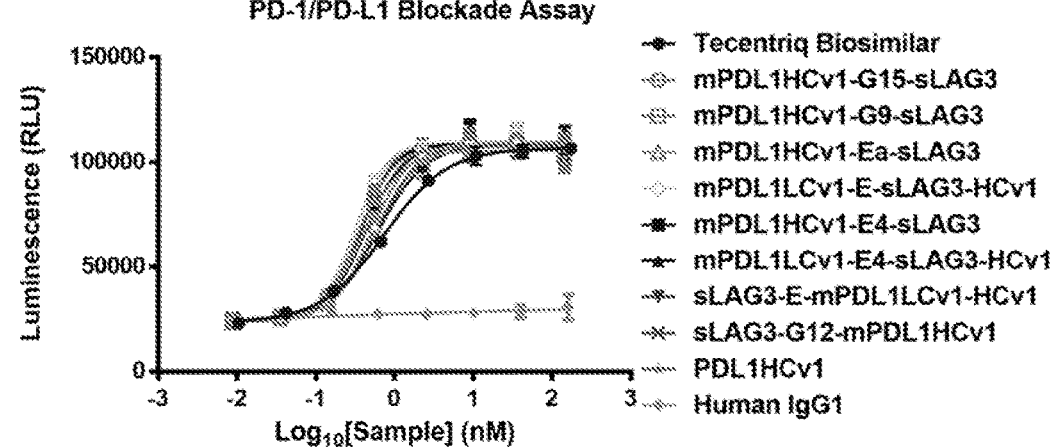
FIG. 11 depicts the results of a PD-1/PD-L1 blockade bioassay.

For the PD-1/PD-L1 blockade bioassay, a Tecentriq bio-similar was utilized as a reference antibody. As shown in FIG. 7, among these SMAB constructs, SMAB of mPDL1HCv1-E-sLAG3 exhibited the highest activity, which is even higher than its parent antibody of PDL1HCv1 (FIG. 7 and Table 7). It also showed similar activity when compared with reference antibody. When the other linkers are used for SMAB construction, SMABs also showed similar activity when compared with reference antibody (FIG. 11)

TABLE 7

| | | | | PD-1/PD-L1 blockade bioassay of SMAB samples | | | |
|---|---|---|---|---|---|---|---|
| Sample ID | Tecentriq Biosimilar | mPDL1LCv1-E-sLAG3-HCv1 | mPDL1LCv1-E-sLAG3-HCv5 | sLAG3-E-mPDL1HCv1 | mPDL1HCv1-E-sLAG3 | PDL1HCv1 | PDL1HCv5 |
| Bottom | 28673 | 30153 | 26304 | 28247 | 28402 | 28940 | 27755 |
| Top | 117172 | 116378 | 115650 | 111690 | 108817 | 113243 | 110103 |
| Log EC$_{50}$ | −0.4666 | 0.1407 | −0.245 | −0.02412 | −0.4826 | −0.3225 | −0.1113 |
| HillSlope | 1.946 | 1.717 | 1.392 | 1.42 | 1.888 | 2.002 | 1.664 |
| EC$_{50}$ | 0.3415 | 1.383 | 0.5688 | 0.946 | 0.3291 | 0.4759 | 0.7739 |

Figure 8:
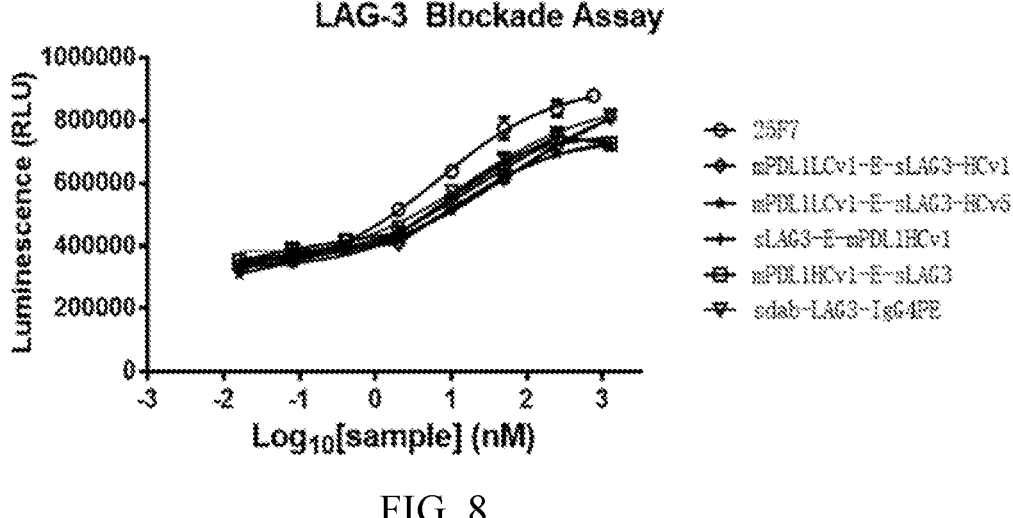
FIG. 8 depicts the results of a LAG-3 blockade bioassay.
Figure 12:
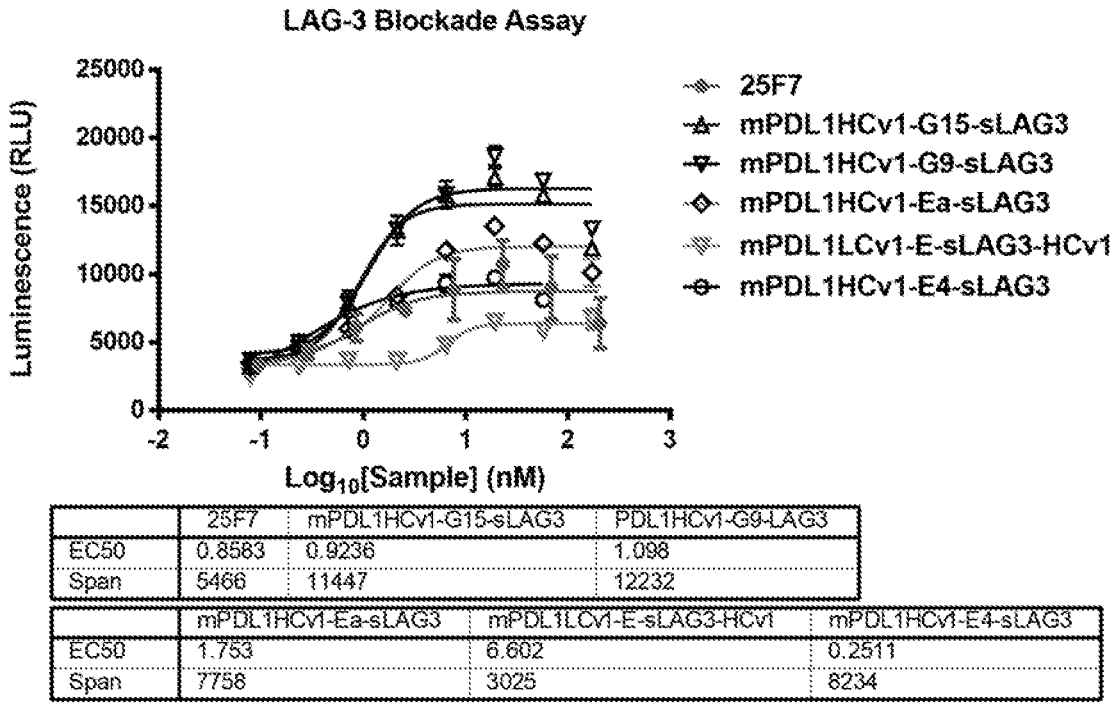
FIG. 12 depicts the results of a LAG-3 blockade bioassay.
Figure 13:
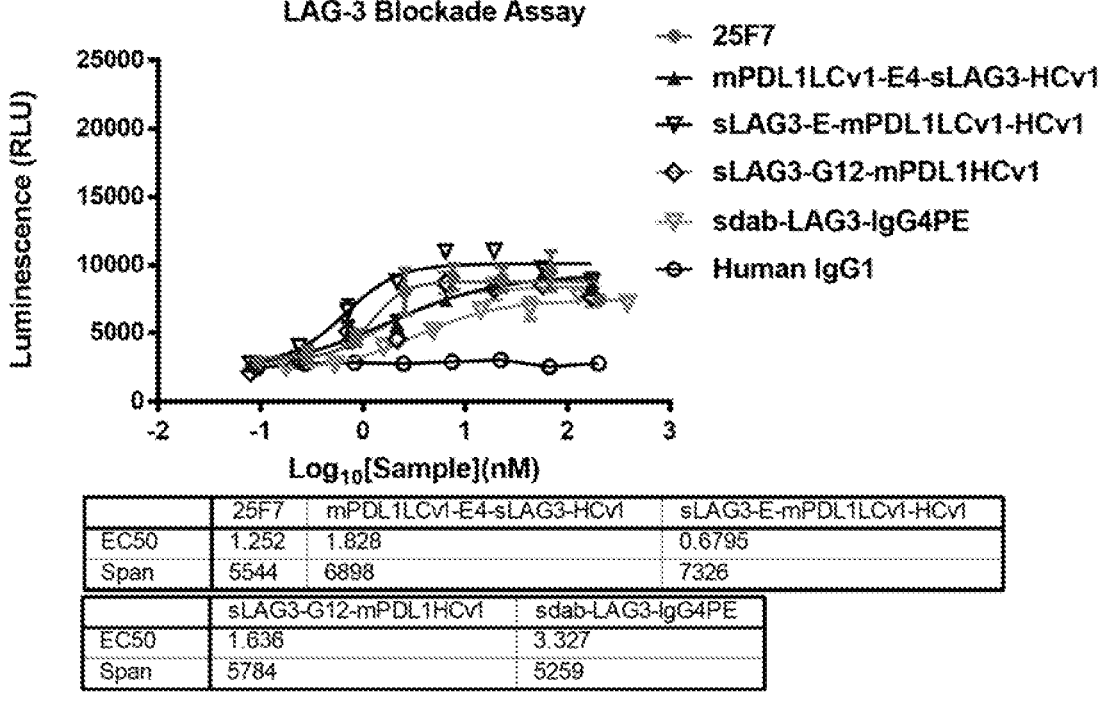
FIG. 13 depicts the results of a LAG-3 blockade bioassay.

For LAG-3 blockade bioassay, 25F7 biosimilar was utilized as a reference antibody. As shown in FIG. 8, among these SMAB constructs, SMAB of mPDL1HCv1-E-sLAG3 still exhibited the higher activity than the control of Fc fusion protein of sdAb-LAG3-IgG4PE, although its activity is a little lower than SMAB of sLAG3-E-mPDL1HCv1 (FIG. 8 and Table 8). When the other linkers are used for SMAB construction, among these SMAB constructs, SMABs of mPDL1HCv1-G15-sLAG3 and mPDL1HCv1-G9-sLAG3 exhibited the highest activity than the control of Fc fusion protein of sdAb-LAG3-IgG4PE (FIG. 12 and FIG. 13). They also showed higher activity than 25F7 mAb.

TABLE 8

| | | | | LAG-3 blockade bioassay of SMAB samples | | |
|---|---|---|---|---|---|---|
| Sample ID | 25F7 | mPDL1LCv1-E-sLAG3-HCv1 | mPDL1LCv1-E-sLAG3-HCv5 | sLAG3-E-mPDL1HCv1 | mPDL1HCv1-E-sLAG3 | sdAb-LAG3-IgG4PE |
| Bottom | 311912 | 339315 | 328468 | 358714 | 380548 | 342637 |
| Top | 917541 | 907832 | 754015 | 751670 | 753090 | 867057 |
| Log EC$_{50}$ | 0.8408 | 1.751 | 1.15 | 0.9886 | 1.142 | 1.231 |
| HillSlope | 0.5605 | 0.4897 | 0.6078 | 0.8279 | 0.8083 | 0.5152 |
| EC$_{50}$ | 6.932 | 56.33 | 14.13 | 9.741 | 13.86 | 17.01 |

Based on the results of LAG-3 blockade bioassay and PD-1/PD-L1 blockade bioassay, SMAB constructs of mPDL1HCv 1-E-sLAG3, mPDL1HCv1-G15-sLAG3 and mPDL1HCv 1-G9-sLAG3 showed better activity when compared to single antibody of PD-L1 or LAG-3. So, this example demonstrated that anti-PD-L1/anti-LAG-3 multiple antigen binding proteins have great potential to improve efficacy based on the in vitro bioassay.

```
DNA sequence of H1: PDL1HCv1 heavy chain (SEQ ID NO: 13):
GAAGTCCAGCTGGTGCAGAGCGGAGCCGAGGTGAAGAAACCAGGCGCTTCTGTGAAGGTGTCCTGCA

AGGCCTCTGGGTACATCTTCACCGGCTACGGCATCACCTGGGTGCGGCAGGCTCCTGGCCAGGGCCTG

GAATGGATGGGCGAGATCTTTCCCAGGAGAGTGCAGACCTACTACTCCGAGAAGTTCAAGGGCAGAG

TGACCATGACCACCGACACCTCCACCTCTACCGCCTACATGGAACTGCGGTCTCTGAGATCCGATGAC

ACCGCTGTGTACTACTGCGCCAGAGACTACGACCCTTATTTCGCCCTGGATTATTGGGGCCAAGGCAC

CACCGTGACAGTCTCCTCCGCCTCTACCAAGGGCCCTTCCGTGTTCCCCCTGGCCCCTAGCAGCAAGTC

CACATCAGGAGGCACCGCTGCTCTGGGCTGCCTGGTCAAGGACTACTTCCCTGAACCTGTGACCGTGT

CCTGGAACTCCGGCGCCCTGACAAGTGGAGTGCATACCTTCCCCGCCGTGCTGCAGTCCTCTGGCCTGT

ACTCTCTGTCTAGCGTGGTCACTGTGCCCTTCCTCTAGCCTCGGCACACAGACATACATCTGCAACGTGA

ACCACAAGCCTTCCAACACCAAAGTGGACAAGAAGGTGGAACCCAAGTCTTGCGACAAAACCCACAC

ATGTCCACCTTGTCCTGCCCCCGAGCTGCTGGGCGGCCCCTCCGTGTTTCTGTTTCCTCCTAAGCCGAA

GGATACACTGATGATCTCCCGGACCCCTGAGGTGACCTGTGTGGTGGTGGACGTGTCTCACGAGGACC

CCGAAGTGAAGTTCAACTGGTACGTGGATGGCGTGGAAGTGCACAATGCTAAGACCAAGCCTAGAGA
```

AGAGCAGTACGCCTCCACCTACCGGGTGGTCTCTGTGCTGACCGTCCTGCATCAGGACTGGCTGAACG

GCAAAGAGTACAAGTGCAAGGTGTCTAACAAGGCTCTGCCTGCTCCTATCGAGAAAACCATCTCTAAG

GCCAAGGGACAGCCTCGGGAACCACAAGTGTACACCCTGCCTCCTTCTAGAGAGGAGATGACCAAGA

ACCAGGTGAGCCTGACCTGCCTCGTGAAAGGCTTCTACCCCTCTGACATCGCCGTGGAGTGGGAGTCC

AATGGCCAGCCTGAGAACAACTACAAGACCACACCTCCAGTTCTGGACTCCGACGGTTCCTTCTTCCT

GTACTCCAAGCTGACCGTTGATAAGTCCAGATGGCAGCAGGGCAACGTGTTCTCCTGTTCCGTGATGC

ACGAGGCCCTGCACAACCACTACACCCAGAAGTCCCTGAGCTTGTCTCCTGGCAAG

Polypeptide sequence of H1: PDL1HCv1 heavy chain (SEQ ID NO: 14):
EVQLVQSGAEVKKPGASVKVSCKASGYIFTGYGITWVRQAPGQGLEWMGEIFPRRVQTYYSEKFKGRVT

MTTDTSTSTAYMELRSLRSDDTAVYYCARDYDPYFALDYWGQGTTVTVSSASTKGPSVFPLAPSSKSTSG

GTAALGCLVKDYFPEPVTVSWNSGALTSGVHTFPAVLQSSGLYSLSSVVTVPSSSLGTQTYICNVNHKPSNT

KVDKKVEPKSCDKTHTCPPCPAPELLGGPSVFLFPPKPKDTLMISRTPEVTCVVVDVSHEDPEVKFNWYVD

GVEVHNAKTKPREEQYASTYRVVSVLTVLHQDWLNGKEYKCKVSNKALPAPIEKTISKAKGQPREPQVYT

LPPSREEMTKNQVSLTCLVKGFYPSDIAVEWESNGQPENNYKTTPPVLDSDGSFFLYSKLTVDKSRWQQGN

VFSCSVMHEALHNHYTQKSLSLSPGK

DNA sequence of L1: PDL1HCv1 or PDL1HCv5 light chain (SEQ ID NO: 15):
GATATCCAGATGACCCAGTCTCCTAGCAGCCTGAGCGCTTCTGTGGGCGACAGAGTGACAATCACCTG

TAGAGCCTCTCAGGACGTGTCCACCGCCGTGGATTGGTACCAGCAGAAGCCCGGCAAGGCTCCTAAGC

TGCTGATCTACTCTGCCTCCTACCGGTACACAGGAGTCCCCGATAGATTCTCTGGCTCCGGCTCTGGAA

CCGACTTCACCTTCACCATCTCCTCTCTGCAGCCTGAGGACATTGCCACCTACTACTGCCAGCAGCACT

ACTCCATCCCTTTTACCTTCGGCCAGGGCACCAAGCTGGAAATCAAGCGGACCGTGGCCGCTCCATCC

GTGTTCATCTTTCCTCCTTCCGACGAGCAGCTGAAGTCTGGCACCGCTTCCGTGGTGTGCCTGCTGAAC

AACTTCTACCCTCGGGAAGCCAAGGTGCAGTGGAAAGTGGACAACGCCCTGCAGTCCGGCAATAGCC

AAGAGTCCGTCACCGAGCAAGACTCCAAGGACTCTACCTATTCTCTCTCCAGCACACTGACCCTGTCTA

AAGCCGACTACGAGAAGCACAAGGTGTACGCCTGCGAAGTGACCCACCAGGGCCTGTCTTCCCCCGTG

ACAAAGTCCTTCAACAGAGGCGAGTGT

Polypeptide sequence of L1: PDL1HCv1 or PDL1HCv5 light chain (SEQ ID NO: 16):
DIQMTQSPSSLSASVGDRVTITCRASQDVSTAVDWYQQKPGKAPKLLIYSASYRYTGVPDRFSGSGSGTDF

TFTISSLQPEDIATYYCQQHYSIPFTFGQGTKLEIKRTVAAPSVFIFPPSDEQLKSGTASVVCLLNNFYPREAK

VQWKVDNALQSGNSQESVTEQDSKDSTYSLSSTLTLSKADYEKHKVYACEVTHQGLSSPVTKSFNRGEC

DNA sequence of H2: PDL1HCv5 heavy chain (SEQ ID NO: 17):
GAAGTCCAGCTGGTGCAGAGCGGAGCCGAGGTGAAGAAACCAGGCGCTTCTGTGAAGGTGTCCTGCA

AGGCCTCTGGGTACATCTTCACCGGCTACGGCATCACCTGGGTGCGGCAGGCTCCTGGCCAGGGCCTG

GAATGGATGGGCGAGATCTTTCCCAGGAGAGTGCAGACCTACTACTCCGAGAAGTTCAAGGGCAGAG

TGACCATGACCgctGACACCTCCACCTCTACCGCCTACATGGAACTGCGGTCTCTGAGATCCGATGACAC

CGCTGTGTACTACTGCGCCAGAGACTACGACCCTTATTTCGCCCTGGATTATTGGGGCCAAGGCACCA

CCGTGACAGTCTCCTCCGCCTCTACCAAGGGCCCTTCCGTGTTCCCCCTGGCCCCTAGCAGCAAGTCCA

CATCAGGAGGCACCGCTGCTCTGGGCTGCCTGGTCAAGGACTACTTCCCTGAACCTGTGACCGTGTCCT

GGAACTCCGGCGCCCTGACAAGTGGAGTGCATACCTTCCCCGCCGTGCTGCAGTCCTCTGGCCTGTACT

CTCTGTCTAGCGTGGTCACTGTGCCTTCCTCTAGCCTCGGCACACAGACATACATCTGCAACGTGAACC

ACAAGCCTTCCAACACCAAAGTGGACAAGAAGGTGGAACCCAAGTCTTGCGACAAAACCCACACATG

TCCACCTTGTCCTGCCCCCGAGCTGCTGGGCGGCCCCTCCGTGTTTCTGTTTCCTCCTAAGCCGAAGGA

-continued

TACACTGATGATCTCCCGGACCCCTGAGGTGACCTGTGTGGTGGTGGACGTGTCTCACGAGGACCCCG

AAGTGAAGTTCAACTGGTACGTGGATGGCGTGGAAGTGCACAATGCTAAGACCAAGCCTAGAGAAGA

GCAGTACGCCTCCACCTACCGGGTGGTCTCTGTGCTGACCGTCCTGCATCAGGACTGGCTGAACGGCA

AAGAGTACAAGTGCAAGGTGTCTAACAAGGCTCTGCCTGCTCCTATCGAGAAAACCATCTCTAAGGCC

AAGGGACAGCCTCGGGAACCACAAGTGTACACCCTGCCTCCTTCTAGAGAGGAGATGACCAAGAACC

AGGTGAGCCTGACCTGCCTCGTGAAAGGCTTCTACCCCTCTGACATCGCCGTGGAGTGGGAGTCCAAT

GGCCAGCCTGAGAACAACTACAAGACCACACCTCCAGTTCTGGACTCCGACGGTTCCTTCTTCCTGTAC

TCCAAGCTGACCGTTGATAAGTCCAGATGGCAGCAGGGCAACGTGTTCTCCTGTTCCGTGATGCACGA

GGCCCTGCACAACCACTACACCCAGAAGTCCCTGAGCTTGTCTCCTGGCAAG

Polypeptide sequence of H2: PDL1HCv5 heavy chain (SEQ ID NO: 18):
EVQLVQSGAEVKKPGASVKVSCKASGYIFTGYGITWVRQAPGQGLEWMGEIFPRRVQTYYSEKFKGRVT

MTADTSTSTAYMELRSLRSDDTAVYYCARDYDPYFALDYWGQGTTVTVSSASTKGPSVFPLAPSSKSTSG

GTAALGCLVKDYFPEPVTVSWNSGALTSGVHTFPAVLQSSGLYSLSSVVTVPSSSLGTQTYICNVNHKPSNT

KVDKKVEPKSCDKTHTCPPCPAPELLGGPSVFLFPPKPKDTLMISRTPEVTCVVVDVSHEDPEVKFNWYVD

GVEVHNAKTKPREEQYASTYRVVSVLTVLHQDWLNGKEYKCKVSNKALPAPIEKTISKAKGQPREPQVYT

LPPSREEMTKNQVSLTCLVKGFYPSDIAVEWESNGQPENNYKTTPPVLDSDGSFFLYSKLTVDKSRWQQGN

VFSCSVMHEALHNHYTQKSLSLSPGK

DNA sequence of L2 (SEQ ID NO: 19):
GATATCCAGATGACCCAGTCTCCTAGCAGCCTGAGCGCTTCTGTGGGCGACAGAGTGACAATCACCTG

TAGAGCCTCTCAGGACGTGTCCACCGCCGTGGATTGGTACCAGCAGAAGCCCGGCAAGGCTCCTAAGC

TGCTGATCTACTCTGCCTCCTACCGGTACACAGGAGTCCCCGATAGATTCTCTGGCTCCGGCTCTGGAA

CCGACTTCACCTTCACCATCTCCTCTCTGCAGCCTGAGGACATTGCCACCTACTACTGCCAGCAGCACT

ACTCCATCCCTTTTACCTTCGGCCAGGGCACCAAGCTGGAAATCAAGCGGACCGTGGCCGCTCCATCC

GTGTTCATCTTTCCTCCTTCCGACGAGCAGCTGAAGTCTGGCACCGCTTCCGTGGTGTGCCTGCTGAAC

AACTTCTACCCTCGGGAAGCCAAGGTGCAGTGGAAAGTGGACAACGCCCTGCAGTCCGGCAATAGCC

AAGAGTCCGTCACCGAGCAAGACTCCAAGGACTCTACCTATTCTCTCTCCAGCACACTGACCCTGTCTA

AAGCCGACTACGAGAAGCACAAGGTGTACGCCTGCGAAGTGACCCACCAGGGCCTGTCTTCCCCCGTG

ACAAAGTCCTTCAACAGAGGCGAGTGTGAACCTAAGTCTAGCGACAAAACTCATACCAGCCCCCCTAG

TCCAGAGGTGCAGCTGGTGGAGTCCGGAGGAGGACTGGTGCAGCCAGGAGGCTCCCTGAGGCTGAGC

TGCGCCGCTTCTGGCTACACCGTGTCCAGCTATTGTATGGGCTGGTTCAGGCAGGCTCCTGGCAAGGG

AAGGGAGGGCGTGTCCGCTATCGACAGCGATGGCAGCGTGTCTTACGCCGACAGCGTGAAGGGCAGA

TTCACCATCTCTAAGGATAACTCCAAGAATACACTGTACCTGCAGATGAACTCTCTGCGCGCCGAGGA

CACCGCCGTGTACTTTTGCGCTGCTGACCTGTGCTGGGTGGACCAGGATCAGGGCGAGTATAATACAT

GGGGCCAGGGCACCCTGGTGACAGTGTCTTCC

Polypeptide sequence of L2 (SEQ ID NO: 20):
DIQMTQSPSSLSASVGDRVTITCRASQDVSTAVDWYQQKPGKAPKLLIYSASYRYTGVPDRFSGSGSGTDF

TFTISSLQPEDIATYYCQQHYSIPFTFGQGTKLEIKRTVAAPSVFIFPPSDEQLKSGTASVVCLLNNFYPREAK

VQWKVDNALQSGNSQESVTEQDSKDSTYSLSSTLTLSKADYEKHKVYACEVTHQGLSSPVTKSFNRGECE

PKSSDKTHTSPPPSPEVQLVESGGGLVQPGGSLRLSCAASGYTVSSYCMGWFRQAPGKGREGVSAIDSDGSV

SYADSVKGRFTISKDNSKNTLYLQMNSLRAEDTAVYFCAADLCWVDQDQGEYNTWGQGTLVTVSS

DNA sequence of H3 (SEQ ID NO: 21):
GAGGTGCAGCTGGTGGAGTCCGGAGGAGGACTGGTGCAGCCAGGAGGCTCCCTGAGGCTGAGCTGCG

CCGCTTCTGGCTACACCGTGTCCAGCTATTGTATGGGCTGGTTCAGGCAGGCTCCTGGCAAGGGAAGG

-continued

GAGGGCGTGTCCGCTATCGACAGCGATGGCAGCGTGTCTTACGCCGACAGCGTGAAGGGCAGATTCAC

CATCTCTAAGGATAACTCCAAGAATACACTGTACCTGCAGATGAACTCTCTGCGCGCCGAGGACACCG

CCGTGTACTTTTGCGCTGCTGACCTGTGCTGGGTGGACCAGGATCAGGGCGAGTATAATACATGGGGC

CAGGGCACCCTGGTGACAGTGTCTTCCGAACCTAAGTCTAGCGACAAAACTCATACCAGCCCCCCTAG

TCCAGAAGTCCAGCTGGTGCAGAGCGGAGCCGAGGTGAAGAAACCAGGCGCTTCTGTGAAGGTGTCC

TGCAAGGCCTCTGGGTACATCTTCACCGGCTACGGCATCACCTGGGTGCGGCAGGCTCCTGGCCAGGG

CCTGGAATGGATGGGCGAGATCTTTCCCAGGAGAGTGCAGACCTACTACTCCGAGAAGTTCAAGGGCA

GAGTGACCATGACCACCGACACCTCCACCTCTACCGCCTACATGGAACTGCGGTCTCTGAGATCCGAT

GACACCGCTGTGTACTACTGCGCCAGAGACTACGACCCTTATTTCGCCCTGGATTATTGGGGCCAAGG

CACCACCGTGACAGTCTCCTCCGCCTCTACCAAGGGCCCTTCCGTGTTCCCCCTGGCCCCTAGCAGCAA

GTCCACATCAGGAGGCACCGCTGCTCTGGGCTGCCTGGTCAAGGACTACTTCCCTGAACCTGTGACCG

TGTCCTGGAACTCCGGCGCCCTGACAAGTGGAGTGCATACCTTCCCCGCCGTGCTGCAGTCCTCTGGCC

TGTACTCTCTGTCTAGCGTGGTCACTGTGCCTTCCTCTAGCCTCGGCACACAGACATACATCTGCAACG

TGAACCACAAGCCTTCCAACACCAAAGTGGACAAGAAGGTGGAACCCAAGTCTTGCGACAAAACCCA

CACATGTCCACCTTGTCCTGCCCCCGAGCTGCTGGGCGGCCCCTCCGTGTTTCTGTTTCCTCCTAAGCC

GAAGGATACACTGATGATCTCCCGGACCCCTGAGGTGACCTGTGTGGTGGTGGACGTGTCTCACGAGG

ACCCCGAAGTGAAGTTCAACTGGTACGTGGATGGCGTGGAAGTGCACAATGCTAAGACCAAGCCTAG

AGAAGAGCAGTACGCCTCCACCTACCGGGTGGTCTCTGTGCTGACCGTCCTGCATCAGGACTGGCTGA

ACGGCAAAGAGTACAAGTGCAAGGTGTCTAACAAGGCTCTGCCTGCTCCTATCGAGAAAACCATCTCT

AAGGCCAAGGGACAGCCTCGGGAACCACAAGTGTACACCCTGCCTCCTTCTAGAGAGGAGATGACCA

AGAACCAGGTGAGCCTGACCTGCCTCGTGAAAGGCTTCTACCCCTCTGACATCGCCGTGGAGTGGGAG

TCCAATGGCCAGCCTGAGAACAACTACAAGACCACACCTCCAGTTCTGGACTCCGACGGTTCCTTCTTC

CTGTACTCCAAGCTGACCGTTGATAAGTCCAGATGGCAGCAGGGCAACGTGTTCTCCTGTTCCGTGAT

GCACGAGGCCCTGCACAACCACTACACCCAGAAGTCCCTGAGCTTGTCTCCTGGCAAG

Polypeptide sequence of H3 (SEQ ID NO: 22):
EVQLVESGGGLVQPGGSLRLSCAASGYTVSSYCMGWFRQAPGKGREGVSAIDSDGSVSYADSVKGRFTIS

KDNSKNTLYLQMNSLRAEDTAVYFCAADLCWVDQDQGEYNTWGQGTLVTVSSEPKSSDKTHTSPPSPEV

QLVQSGAEVKKPGASVKVSCKASGYIFTGYGITWVRQAPGQGLEWMGEIFPRRVQTYYSEKFKGRVTMTT

DTSTSTAYMELRSLRSDDTAVYYCARDYDPYFALDYWGQGTTVTVSSASTKGPSVFPLAPSSKSTSGGTAA

LGCLVKDYFPEPVTVSWNSGALTSGVHTFPAVLQSSGLYSLSSVVTVPSSSLGTQTYICNVNHKPSNTKVD

KKVEPKSCDKTHTCPPCPAPELLGGPSVFLFPPKPKDTLMISRTPEVTCVVVDVSHEDPEVKFNWYVDGVE

VHNAKTKPREEQYASTYRVVSVLTVLHQDWLNGKEYKCKVSNKALPAPIEKTISKAKGQPREPQVYTLPP

SREEMTKNQVSLTCLVKGFYPSDIAVEWESNGQPENNYKTTPPVLDSDGSFFLYSKLTVDKSRWQQGNVF

SCSVMHEALHNHYTQKSLSLSPGK

DNA sequence of H4 (SEQ ID NO: 23):
GAAGTCCAGCTGGTGCAGAGCGGAGCCGAGGTGAAGAAACCAGGCGCTTCTGTGAAGGTGTCCTGCA

AGGCCTCTGGGTACATCTTCACCGGCTACGGCATCACCTGGGTGCGGCAGGCTCCTGGCCAGGGCCTG

GAATGGATGGGCGAGATCTTTCCCAGGAGAGTGCAGACCTACTACTCCGAGAAGTTCAAGGGCAGAG

TGACCATGACCACCGACACCTCCACCTCTACCGCCTACATGGAACTGCGGTCTCTGAGATCCGATGAC

ACCGCTGTGTACTACTGCGCCAGAGACTACGACCCTTATTTCGCCCTGGATTATTGGGGCCAAGGCAC

CACCGTGACAGTCTCCTCCGCCTCTACCAAGGGCCCTTCCGTGTTCCCCCTGGCCCCTAGCAGCAAGTC

-continued

CACATCAGGAGGCACCGCTGCTCTGGGCTGCCTGGTCAAGGACTACTTCCCTGAACCTGTGACCGTGT

CCTGGAACTCCGGCGCCCTGACAAGTGGAGTGCATACCTTCCCCGCCGTGCTGCAGTCCTCTGGCCTGT

ACTCTCTGTCTAGCGTGGTCACTGTGCCTTCCTCTAGCCTCGGCACACAGACATACATCTGCAACGTGA

ACCACAAGCCTTCCAACACCAAAGTGGACAAGAAGGTGGAACCCAAGTCTTGCGACAAAACCCACAC

ATGTCCACCTTGTCCTGCCCCCGAGCTGCTGGGCGGCCCCTCCGTGTTTCTGTTTCCTCCTAAGCCGAA

GGATACACTGATGATCTCCCGGACCCCTGAGGTGACCTGTGTGGTGGTGGACGTGTCTCACGAGGACC

CCGAAGTGAAGTTCAACTGGTACGTGGATGGCGTGGAAGTGCACAATGCTAAGACCAAGCCTAGAGA

AGAGCAGTACGCCTCCACCTACCGGGTGGTCTCTGTGCTGACCGTCCTGCATCAGGACTGGCTGAACG

GCAAAGAGTACAAGTGCAAGGTGTCTAACAAGGCTCTGCCTGCTCCTATCGAGAAAACCATCTCTAAG

GCCAAGGGACAGCCTCGGGAACCACAAGTGTACACCCTGCCTCCTTCTAGAGAGGAGATGACCAAGA

ACCAGGTGAGCCTGACCTGCCTCGTGAAAGGCTTCTACCCCTCTGACATCGCCGTGGAGTGGGAGTCC

AATGGCCAGCCTGAGAACAACTACAAGACCACACCTCCAGTTCTGGACTCCGACGGTTCCTTCTTCCT

GTACTCCAAGCTGACCGTTGATAAGTCCAGATGGCAGCAGGGCAACGTGTTCTCCTGTTCCGTGATGC

ACGAGGCCCTGCACAACCACTACACCCAGAAGTCCCTGAGCTTGTCTCCTGGCAAGGAACCTAAGTCT

AGCGACAAAACTCATACCAGCCCCCCTAGTCCAGAGGTGCAGCTGGTGGAGTCCGGAGGAGGACTGG

TGCAGCCAGGAGGCTCCCTGAGGCTGAGCTGCGCCGCTTCTGGCTACACCGTGTCCAGCTATTGTATG

GGCTGGTTCAGGCAGGCTCCTGGCAAGGGAAGGGAGGGCGTGTCCGCTATCGACAGCGATGGCAGCG

TGTCTTACGCCGACAGCGTGAAGGGCAGATTCACCATCTCTAAGGATAACTCCAAGAATACACTGTAC

CTGCAGATGAACTCTCTGCGCGCCGAGGACACCGCCGTGTACTTTTGCGCTGCTGACCTGTGCTGGGTG

GACCAGGATCAGGGCGAGTATAATACATGGGGCCAGGGCACCCTGGTGACAGTGTCTTCC

Polypeptide sequence of H4 (SEQ ID NO: 24):
EVQLVQSGAEVKKPGASVKVSCKASGYIFTGYGITWVRQAPGQGLEWMGEIFPRRVQTYYSEKFKGRVT

MTTDTSTSTAYMELRSLRSDDTAVYYCARDYDPYFALDYWGQGTTVTVSSASTKGPSVFPLAPSSKSTSG

GTAALGCLVKDYFPEPVTVSWNSGALTSGVHTFPAVLQSSGLYSLSSVVTVPSSSLGTQTYICNVNHKPSNT

KVDKKVEPKSCDKTHTCPPCPAPELLGGPSVFLFPPKPKDTLMISRTPEVTCVVVDVSHEDPEVKFNWYVD

GVEVHNAKTKPREEQYASTYRVVSVLTVLHQDWLNGKEYKCKVSNKALPAPIEKTISKAKGQPREPQVYT

LPPSREEMTKNQVSLTCLVKGFYPSDIAVEWESNGQPENNYKTTPPVLDSDGSFFLYSKLTVDKSRWQQGN

VFSCSVMHEALHNHYTQKSLSLSPGKEPKSSDKTHTSPPSPEVQLVESGGGLVQPGGSLRLSCAASGYTVSS

YCMGWFRQAPGKGREGVSAIDSDGSVSYADSVKGRFTISKDNSKNTLYLQMNSLRAEDTAVYFCAADLC

WVDQDQGEYNTWGQGTLVTVSS

DNA sequence of H5 (SEQ ID NO: 25):
GAGGTGCAGCTGGTGGAGTCCGGAGGAGGACTGGTGCAGCCAGGAGGCTCCCTGAGGCTGAGCTGCG

CCGCTTCTGGCTACACCGTGTCCAGCTATTGTATGGGCTGGTTCAGGCAGGCTCCTGGCAAGGGAAGG

GAGGGCGTGTCCGCTATCGACAGCGATGGCAGCGTGTCTTACGCCGACAGCGTGAAGGGCAGATTCAC

CATCTCTAAGGATAACTCCAAGAATACACTGTACCTGCAGATGAACTCTCTGCGCGCCGAGGACACCG

CCGTGTACTTTTGCGCTGCTGACCTGTGCTGGGTGGACCAGGATCAGGGCGAGTATAATACATGGGGC

CAGGGCACCCTGGTGACAGTGTCTTCCGAACCTAAGTCTAGCGACAAAACTCATACCAGCCCCCCTAG

TCCAGAAGTCCAGCTGGTGCAGAGCGGAGCCGAGGTGAAGAAACCAGGCGCTTCTGTGAAGGTGTCC

TGCAAGGCCTCTGGGTACATCTTCACCGGCTACGGCATCACCTGGGTGCGGCAGGCTCCTGGCCAGGG

CCTGGAATGGATGGGCGAGATCTTTCCCAGGAGAGTGCAGACCTACTACTCCGAGAAGTTCAAGGGCA

GAGTGACCATGACCGctGACACCTCCACCTCTACCGCCTACATGGAACTGCGGTCTCTGAGATCCGATG

ACACCGCTGTGTACTACTGCGCCAGAGACTACGACCCTTATTTCGCCCTGGATTATTGGGGCCAAGGC

-continued

ACCACCGTGACAGTCTCCTCCGCCTCTACCAAGGGCCCTTCCGTGTTCCCCCTGGCCCCTAGCAGCAAG

TCCACATCAGGAGGCACCGCTGCTCTGGGCTGCCTGGTCAAGGACTACTTCCCTGAACCTGTGACCGT

GTCCTGGAACTCCGGCGCCCTGACAAGTGGAGTGCATACCTTCCCCGCCGTGCTGCAGTCCTCTGGCCT

GTACTCTCTGTCTAGCGTGGTCACTGTGCCTTCCTCTAGCCTCGGCACACAGACATACATCTGCAACGT

GAACCACAAGCCTTCCAACACCAAAGTGGACAAGAAGGTGGAACCCAAGTCTTGCGACAAAACCCAC

ACATGTCCACCTTGTCCTGCCCCCGAGCTGCTGGGCGGCCCCTCCGTGTTTCTGTTTCCTCCTAAGCCG

AAGGATACACTGATGATCTCCCGGACCCCTGAGGTGACCTGTGTGGTGGTGGACGTGTCTCACGAGGA

CCCCGAAGTGAAGTTCAACTGGTACGTGGATGGCGTGGAAGTGCACAATGCTAAGACCAAGCCTAGA

GAAGAGCAGTACGCCTCCACCTACCGGGTGGTCTCTGTGCTGACCGTCCTGCATCAGGACTGGCTGAA

CGGCAAAGAGTACAAGTGCAAGGTGTCTAACAAGGCTCTGCCTGCTCCTATCGAGAAAACCATCTCTA

AGGCCAAGGGACAGCCTCGGGAACCACAAGTGTACACCCTGCCTCCTTCTAGAGAGGAGATGACCAA

GAACCAGGTGAGCCTGACCTGCCTCGTGAAAGGCTTCTACCCCTCTGACATCGCCGTGGAGTGGGAGT

CCAATGGCCAGCCTGAGAACAACTACAAGACCACACCTCCAGTTCTGGACTCCGACGGTTCCTTCTTC

CTGTACTCCAAGCTGACCGTTGATAAGTCCAGATGGCAGCAGGGCAACGTGTTCTCCTGTTCCGTGAT

GCACGAGGCCCTGCACAACCACTACACCCAGAAGTCCCTGAGCTTGTCTCCTGGCAAG

Polypeptide sequence of H5 (SEQ ID NO: 26):
EVQLVESGGGLVQPGGSLRLSCAASGYTVSSYCMGWFRQAPGKGREGVSAIDSDGSVSYADSVKGRFTIS

KDNSKNTLYLQMNSLRAEDTAVYFCAADLCWVDQDQGEYNTWGQGTLVTVSSEPKSSDKTHTSPPSPEV

QLVQSGAEVKKPGASVKVSCKASGYIFTGYGITWVRQAPGQGLEWMGEIFPRRVQTYYSEKFKGRVTMT

ADTSTSTAYMELRSLRSDDTAVYYCARDYDPYFALDYWGQGTTVTVSSASTKGPSVFPLAPSSKSTSGGTA

ALGCLVKDYFPEPVTVSWNSGALTSGVHTFPAVLQSSGLYSLSSVVTVPSSSLGTQTYICNVNHKPSNTKV

DKKVEPKSCDKTHTCPPCPAPELLGGPSVFLFPPKPKDTLMISRTPEVTCVVVDVSHEDPEVKFNWYVDGV

EVHNAKTKPREEQYASTYRVVSVLTVLHQDWLNGKEYKCKVSNKALPAPIEKTISKAKGQPREPQVYTLP

PSREEMTKNQVSLTCLVKGFYPSDIAVEWESNGQPENNYKTTPPVLDSDGSFFLYSKLTVDKSRWQQGNV

FSCSVMHEALHNHYTQKSLSLSPGK

DNA sequence of H6 (SEQ ID NO: 27):
GAAGTCCAGCTGGTGCAGAGCGGAGCCGAGGTGAAGAAACCAGGCGCTTCTGTGAAGGTGTCCTGCA

AGGCCTCTGGGTACATCTTCACCGGCTACGGCATCACCTGGGTGCGGCAGGCTCCTGGCCAGGGCCTG

GAATGGATGGGCGAGATCTTTCCCAGGAGAGTGCAGACCTACTACTCCGAGAAGTTCAAGGGCAGAG

TGACCATGACCgctGACACCTCCACCTCTACCGCCTACATGGAACTGCGGTCTCTGAGATCCGATGACAC

CGCTGTGTACTACTGCGCCAGAGACTACGACCCTTATTTCGCCCTGGATTATTGGGGCCAAGGCACCA

CCGTGACAGTCTCCTCCGCCTCTACCAAGGGCCCTTCCGTGTTCCCCCTGGCCCCTAGCAGCAAGTCCA

CATCAGGAGGCACCGCTGCTCTGGGCTGCCTGGTCAAGGACTACTTCCCTGAACCTGTGACCGTGTCCT

GGAACTCCGGCGCCCTGACAAGTGGAGTGCATACCTTCCCCGCCGTGCTGCAGTCCTCTGGCCTGTACT

CTCTGTCTAGCGTGGTCACTGTGCCTTCCTCTAGCCTCGGCACACAGACATACATCTGCAACGTGAACC

ACAAGCCTTCCAACACCAAAGTGGACAAGAAGGTGGAACCCAAGTCTTGCGACAAAACCCACACATG

TCCACCTTGTCCTGCCCCCGAGCTGCTGGGCGGCCCCTCCGTGTTTCTGTTTCCTCCTAAGCCGAAGGA

TACACTGATGATCTCCCGGACCCCTGAGGTGACCTGTGTGGTGGTGGACGTGTCTCACGAGGACCCCG

AAGTGAAGTTCAACTGGTACGTGGATGGCGTGGAAGTGCACAATGCTAAGACCAAGCCTAGAGAAGA

GCAGTACGCCTCCACCTACCGGGTGGTCTCTGTGCTGACCGTCCTGCATCAGGACTGGCTGAACGGCA

AAGAGTACAAGTGCAAGGTGTCTAACAAGGCTCTGCCTGCTCCTATCGAGAAAACCATCTCTAAGGCC

AAGGGACAGCCTCGGGAACCACAAGTGTACACCCTGCCTCCTTCTAGAGAGGAGATGACCAAGAACC

AGGTGAGCCTGACCTGCCTCGTGAAAGGCTTCTACCCCTCTGACATCGCCGTGGAGTGGGAGTCCAAT

GGCCAGCCTGAGAACAACTACAAGACCACACCTCCAGTTCTGGACTCCGACGGTTCCTTCTTCCTGTAC

TCCAAGCTGACCGTTGATAAGTCCAGATGGCAGCAGGGCAACGTGTTCTCCTGTTCCGTGATGCACGA

GGCCCTGCACAACCACTACACCCAGAAGTCCCTGAGCTTGTCTCCTGGCAAGGAACCTAAGTCTAGCG

ACAAAACTCATACCAGCCCCCCTAGTCCAGAGGTGCAGCTGGTGGAGTCCGGAGGAGGACTGGTGCA

GCCAGGAGGCTCCCTGAGGCTGAGCTGCGCCGCTTCTGGCTACACCGTGTCCAGCTATTGTATGGGCT

GGTTCAGGCAGGCTCCTGGCAAGGGAAGGGAGGGCGTGTCCGCTATCGACAGCGATGGCAGCGTGTC

TTACGCCGACAGCGTGAAGGGCAGATTCACCATCTCTAAGGATAACTCCAAGAATACACTGTACCTGC

AGATGAACTCTCTGCGCGCCGAGGACACCGCCGTGTACTTTTGCGCTGCTGACCTGTGCTGGGTGGAC

CAGGATCAGGGCGAGTATAATACATGGGGCCAGGGCACCCTGGTGACAGTGTCTTCC

Polypeptide sequence of H6 (SEQ ID NO: 28):
EVQLVQSGAEVKKPGASVKVSCKASGYIFTGYGITWVRQAPGQGLEWMGEIFPRRVQTYYSEKFKGRVT

MTADTSTSTAYMELRSLRSDDTAVYYCARDYDPYFALDYWGQGTTVTVSSASTKGPSVFPLAPSSKSTSG

GTAALGCLVKDYFPEPVTVSWNSGALTSGVHTFPAVLQSSGLYSLSSVVTVPSSSLGTQTYICNVNHKPSNT

KVDKKVEPKSCDKTHTCPPCPAPELLGGPSVFLFPPKPKDTLMISRTPEVTCVVVDVSHEDPEVKFNWYVD

GVEVHNAKTKPREEQYASTYRVVSVLTVLHQDWLNGKEYKCKVSNKALPAPIEKTISKAKGQPREPQVYT

LPPSREEMTKNQVSLTCLVKGFYPSDIAVEWESNGQPENNYKTTPPVLDSDGSFFLYSKLTVDKSRWQQGN

VFSCSVMHEALHNHYTQKSLSLSPGKEPKSSDKTHTSPPSPEVQLVESGGGLVQPGGSLRLSCAASGYTVSS

YCMGWFRQAPGKGREGVSAIDSDGSVSYADSVKGRFTISKDNSKNTLYLQMNSLRAEDTAVYFCAADLC

WVDQDQGEYNTWGQGTLVTVSS

DNA sequence of L3 (SEQ ID NO: 29):
GAGGTGCAGCTGGTGGAGTCCGGAGGAGGACTGGTGCAGCCAGGAGGCTCCCTGAGGCTGAGCTGCG

CCGCTTCTGGCTACACCGTGTCCAGCTATTGTATGGGCTGGTTCAGGCAGGCTCCTGGCAAGGGAAGG

GAGGGCGTGTCCGCTATCGACAGCGATGGCAGCGTGTCTTACGCCGACAGCGTGAAGGGCAGATTCAC

CATCTCTAAGGATAACTCCAAGAATACACTGTACCTGCAGATGAACTCTCTGCGCGCCGAGGACACCG

CCGTGTACTTTTGCGCTGCTGACCTGTGCTGGGTGGACCAGGATCAGGGCGAGTATAATACATGGGGC

CAGGGCACCCTGGTGACAGTGTCTTCCGAACCTAAGTCTAGCGACAAAACTCATACCAGCCCCCCTAG

TCCAGATATCCAGATGACCCAGTCTCCTAGCAGCCTGAGCGCTTCTGTGGGCGACAGAGTGACAATCA

CCTGTAGAGCCTCTCAGGACGTGTCCACCGCCGTGGATTGGTACCAGCAGAAGCCCGGCAAGGCTCCT

AAGCTGCTGATCTACTCTGCCTCCTACCGGTACACAGGAGTCCCCGATAGATTCTCTGGCTCCGGCTCT

GGAACCGACTTCACCTTCACCATCTCCTCTCTGCAGCCTGAGGACATTGCCACCTACTACTGCCAGCAG

CACTACTCCATCCCTTTTACCTTCGGCCAGGGCACCAAGCTGGAAATCAAGCGGACCGTGGCCGCTCC

ATCCGTGTTCATCTTTCCTCCTTCCGACGAGCAGCTGAAGTCTGGCACCGCTTCCGTGGTGTGCCTGCT

GAACAACTTCTACCCTCGGGAAGCCAAGGTGCAGTGGAAAGTGGACAACGCCCTGCAGTCCGGCAAT

AGCCAAGAGTCCGTCACCGAGCAAGACTCCAAGGACTCTACCTATTCTCTCTCCAGCACACTGACCCT

GTCTAAAGCCGACTACGAGAAGCACAAGGTGTACGCCTGCGAAGTGACCCACCAGGGCCTGTCTTCCC

CCGTGACAAAGTCCTTCAACAGAGGCGAGTGT

Polypeptide sequence of L3 (SEQ ID NO: 30):
EVQLVESGGGLVQPGGSLRLSCAASGYTVSSYCMGWFRQAPGKGREGVSAIDSDGSVSYADSVKGRFTIS

KDNSKNTLYLQMNSLRAEDTAVYFCAADLCWVDQDQGEYNTWGQGTLVTVSSEPKSSDKTHTSPPSPDIQ

MTQSPSSLSASVGDRVTITCRASQDVSTAVDWYQQKPGKAPKLLIYSASYRYTGVPDRFSGSGSGTDFTFTI

-continued

SSLQPEDIATYYCQQHYSIPFTFGQGTKLEIKRTVAAPSVFIFPPSDEQLKSGTASVVCLLNNFYPREAKVQW

KVDNALQSGNSQESVTEQDSKDSTYSLSSTLTLSKADYEKHKVYACEVTHQGLSSPVTKSFNRGEC

DNA sequence of H7 (SEQ ID NO: 31):
GAGGTGCAGCTGGTGGAGTCCGGAGGAGGACTGGTGCAGCCAGGAGGCTCCCTGAGGCTGAGCTGCG

CCGCTTCTGGCTACACCGTGTCCAGCTATTGTATGGGCTGGTTCAGGCAGGCTCCTGGCAAGGGAAGG

GAGGGCGTGTCCGCTATCGACAGCGATGGCAGCGTGTCTTACGCCGACAGCGTGAAGGGCAGATTCAC

CATCTCTAAGGATAACTCCAAGAATACACTGTACCTGCAGATGAACTCTCTGCGCGCCGAGGACACCG

CCGTGTACTTTTGCGCTGCTGACCTGTGCTGGGTGGACCAGGATCAGGGCGAGTATAATACATGGGGC

CAGGGCACCCTGGTGACAGTGTCTTCCGAGAGCAAGTACGGACCACCTTGCCCACCATGTCCAGCTCC

TGAGTTTGAGGGAGGACCATCCGTGTTCCTGTTTCCTCCAAAGCCTAAGGACACCCTGATGATCAGCC

GGACACCTGAGGTGACCTGCGTGGTGGTGGACGTGTCTCAGGAGGATCCAGAGGTGCAGTTCAACTGG

TACGTGGATGGCGTGGAGGTGCACAATGCTAAGACCAAGCCAAGAGAGGAGCAGTTTAATTCCACAT

ACCGCGTGGTGAGCGTGCTGACCGTGCTGCATCAGGATTGGCTGAACGGCAAGGAGTATAAGTGCAA

GGTGTCCAATAAGGGCCTGCCCAGCTCTATCGAGAAGACAATCAGCAAGGCTAAGGGACAGCCTAGG

GAGCCACAGGTGTACACCCTGCCCCCTTCTCAGGAGGAGATGACAAAGAACCAGGTGTCCCTGACCTG

TCTGGTGAAGGGCTTCTATCCAAGCGACATCGCTGTGGAGTGGGAGTCTAATGGCCAGCCCGAGAACA

ATTACAAGACCACACCACCCGTGCTGGACTCTGATGGCTCCTTCTTTCTGTATTCTAGGCTGACAGTGG

ATAAGTCCCGGTGGCAGGAGGGCAACGTGTTTAGCTGCTCTGTGATGCACGAGGCCCTGCACAATCAT

TATACCCAGAAGTCCCTGAGCCTGTCTCTGGGCAAGT

Polypeptide sequence of H7 (SEQ ID NO: 32):
EVQLVESGGGLVQPGGSLRLSCAASGYTVSSYCMGWFRQAPGKGREGVSAIDSDGSVSYADSVKGRFTIS

KDNSKNTLYLQMNSLRAEDTAVYFCAADLCWVDQDQGEYNTWGQGTLVTVSSESKYGPPCPPCPAPEFE

GGPSVFLFPPKPKDTLMISRTPEVTCVVVDVSQEDPEVQFNWYVDGVEVHNAKTKPREEQFNSTYRVVSV

LTVLHQDWLNGKEYKCKVSNKGLPSSIEKTISKAKGQPREPQVYTLPPSQEEMTKNQVSLTCLVKGFYPSD

IAVEWESNGQPENNYKTTPPVLDSDGSFFLYSRLTVDKSRWQEGNVFSCSVMHEALHNHYTQKSLSLSLG

K

Amino acid sequence of E4-linker (SEQ ID NO: 40):
ESKYGPPSPPSP

Amino acid sequence of G9-linker (SEQ ID NO: 41):
GGGGSGGGS

Amino acid sequence of G12-linker (SEQ ID NO: 42):
GGGGSGGGGSGS

Amino acid sequence of Ea-linker (SEQ ID NO: 43):
EPKSSDKGHGGPPGP

DNA sequence of H8 (SEQ ID NO: 44):
GAAGTCCAGCTGGTGCAGAGCGGAGCCGAGGTGAAGAAACCAGGCGCTTCTGTGAAGGTGTCCTGCA

AGGCCTCTGGGTACATCTTCACCGGCTACGGCATCACCTGGGTGCGGCAGGCTCCTGGCCAGGGCCTG

GAATGGATGGGCGAGATCTTTCCCAGGAGAGTGCAGACCTACTACTCCGAGAAGTTCAAGGGCAGAG

TGACCATGACCACCGACACCTCCACCTCTACCGCCTACATGGAACTGCGGTCTCTGAGATCCGATGAC

ACCGCTGTGTACTACTGCGCCAGAGACTACGACCCTTATTTCGCCCTGGATTATTGGGGCCAAGGCAC

CACCGTGACAGTCTCCTCCGCCTCTACCAAGGGCCCTTCCGTGTTCCCCCTGGCCCCTAGCAGCAAGTC

CACATCAGGAGGCACCGCTGCTCTGGGCTGCCTGGTCAAGGACTACTTCCCTGAACCTGTGACCGTGT

CCTGGAACTCCGGCGCCCTGACAAGTGGAGTGCATACCTTCCCCGCCGTGCTGCAGTCCTCTGGCCTGT

ACTCTCTGTCTAGCGTGGTCACTGTGCCTTCCTCTAGCCTCGGCACACAGACATACATCTGCAACGTGA

-continued

```
ACCACAAGCCTTCCAACACCAAAGTGGACAAGAAGGTGGAACCCAAGTCTTGCGACAAAACCCACAC

ATGTCCACCTTGTCCTGCCCCCGAGCTGCTGGGCGGCCCCTCCGTGTTTCTGTTTCCTCCTAAGCCGAA

GGATACACTGATGATCTCCCGGACCCCTGAGGTGACCTGTGTGGTGGTGGACGTGTCTCACGAGGACC

CCGAAGTGAAGTTCAACTGGTACGTGGATGGCGTGGAAGTGCACAATGCTAAGACCAAGCCTAGAGA

AGAGCAGTACGCCTCCACCTACCGGGTGGTCTCTGTGCTGACCGTCCTGCATCAGGACTGGCTGAACG

GCAAAGAGTACAAGTGCAAGGTGTCTAACAAGGCTCTGCCTGCTCCTATCGAGAAAACCATCTCTAAG

GCCAAGGGACAGCCTCGGGAACCACAAGTGTACACCCTGCCTCCTTCTAGAGAGGAGATGACCAAGA

ACCAGGTGAGCCTGACCTGCCTCGTGAAAGGCTTCTACCCCTCTGACATCGCCGTGGAGTGGGAGTCC

AATGGCCAGCCTGAGAACAACTACAAGACCACACCTCCAGTTCTGGACTCCGACGGTTCCTTCTTCCT

GTACTCCAAGCTGACCGTTGATAAGTCCAGATGGCAGCAGGGCAACGTGTTCTCCTGTTCCGTGATGC

ACGAGGCCCTGCACAACCACTACACCCAGAAGTCCCTGAGCTTGTCTCCTGGCAAGGGTGGAGGCGGT

AGTGGAGGCGGTGGTTCAGGCGGAGGCGGATCTGAGGTGCAGCTGGTGGAGTCCGGAGGAGGACTGG

TGCAGCCAGGAGGCTCCCTGAGGCTGAGCTGCGCCGCTTCTGGCTACACCGTGTCCAGCTATTGTATG

GGCTGGTTCAGGCAGGCTCCTGGCAAGGGAAGGGAGGGCGTGTCCGCTATCGACAGCGATGGCAGCG

TGTCTTACGCCGACAGCGTGAAGGGCAGATTCACCATCTCTAAGGATAACTCCAAGAATACACTGTAC

CTGCAGATGAACTCTCTGCGCGCCGAGGACACCGCCGTGTACTTTTGCGCTGCTGACCTGTGCTGGGTG

GACCAGGATCAGGGCGAGTATAATACATGGGGCCAGGGCACCCTGGTGACAGTGTCTTCC
```

Polypeptide sequence of H8 (SEQ ID NO: 45):
```
EVQLVQSGAEVKKPGASVKVSCKASGYIFTGYGITWVRQAPGQGLEWMGEIFPRRVQTYYSEKFKGRVT

MTTDTSTSTAYMELRSLRSDDTAVYYCARDYDPYFALDYWGQGTTVTVSSASTKGPSVFPLAPSSKSTSG

GTAALGCLVKDYFPEPVTVSWNSGALTSGVHTFPAVLQSSGLYSLSSVVTVPSSSLGTQTYICNVNHKPSNT

KVDKKVEPKSCDKTHTCPPCPAPELLGGPSVFLFPPKPKDTLMISRTPEVTCVVVDVSHEDPEVKFNWYVD

GVEVHNAKTKPREEQYASTYRVVSVLTVLHQDWLNGKEYKCKVSNKALPAPIEKTISKAKGQPREPQVYT

LPPSREEMTKNQVSLTCLVKGFYPSDIAVEWESNGQPENNYKTTPPVLDSDGSFFLYSKLTVDKSRWQQGN

VFSCSVMHEALHNHYTQKSLSLSPGKGGGGSGGGGSGGGGSEVQLVESGGGLVQPGGSLRLSCAASGYTV

SSYCMGWFRQAPGKGREGVSAIDSDGSVSYADSVKGRFTISKDNSKNTLYLQMNSLRAEDTAVYFCAADL

CWVDQDQGEYNTWGQGTLVTVSS
```

DNA sequence of H9 (SEQ ID NO: 46):
```
GAAGTCCAGCTGGTGCAGAGCGGAGCCGAGGTGAAGAAACCAGGCGCTTCTGTGAAGGTGTCCTGCA

AGGCCTCTGGGTACATCTTCACCGGCTACGGCATCACCTGGGTGCGGCAGGCTCCTGGCCAGGGCCTG

GAATGGATGGGCGAGATCTTTCCCAGGAGAGTGCAGACCTACTACTCCGAGAAGTTCAAGGGCAGAG

TGACCATGACCACCGACACCTCCACCTCTACCGCCTACATGGAACTGCGGTCTCTGAGATCCGATGAC

ACCGCTGTGTACTACTGCGCCAGAGACTACGACCCTTATTTCGCCCTGGATTATTGGGGCCAAGGCAC

CACCGTGACAGTCTCCTCCGCCTCTACCAAGGGCCCTTCCGTGTTCCCCCTGGCCCCTAGCAGCAAGTC

CACATCAGGAGGCACCGCTGCTCTGGGCTGCCTGGTCAAGGACTACTTCCCTGAACCTGTGACCGTGT

CCTGGAACTCCGGCGCCCTGACAAGTGGAGTGCATACCTTCCCCGCCGTGCTGCAGTCCTCTGGCCTGT

ACTCTCTGTCTAGCGTGGTCACTGTGCCTTCCTCTAGCCTCGGCACACAGACATACATCTGCAACGTGA

ACCACAAGCCTTCCAACACCAAAGTGGACAAGAAGGTGGAACCCAAGTCTTGCGACAAAACCCACAC

ATGTCCACCTTGTCCTGCCCCCGAGCTGCTGGGCGGCCCCTCCGTGTTTCTGTTTCCTCCTAAGCCGAA

GGATACACTGATGATCTCCCGGACCCCTGAGGTGACCTGTGTGGTGGTGGACGTGTCTCACGAGGACC

CCGAAGTGAAGTTCAACTGGTACGTGGATGGCGTGGAAGTGCACAATGCTAAGACCAAGCCTAGAGA

AGAGCAGTACGCCTCCACCTACCGGGTGGTCTCTGTGCTGACCGTCCTGCATCAGGACTGGCTGAACG
```

-continued

```
GCAAAGAGTACAAGTGCAAGGTGTCTAACAAGGCTCTGCCTGCTCCTATCGAGAAAACCATCTCTAAG

GCCAAGGGACAGCCTCGGGAACCACAAGTGTACACCCTGCCTCCTTCTAGAGAGGAGATGACCAAGA

ACCAGGTGAGCCTGACCTGCCTCGTGAAAGGCTTCTACCCCTCTGACATCGCCGTGGAGTGGGAGTCC

AATGGCCAGCCTGAGAACAACTACAAGACCACACCTCCAGTTCTGGACTCCGACGGTTCCTTCTTCCT

GTACTCCAAGCTGACCGTTGATAAGTCCAGATGGCAGCAGGGCAACGTGTTCTCCTGTTCCGTGATGC

ACGAGGCCCTGCACAACCACTACACCCAGAAGTCCCTGAGCTTGTCTCCTGGCAAGGGTGGAGGCGGT

AGTGGAGGCGGTTCAGAGGTGCAGCTGGTGGAGTCCGGAGGAGGACTGGTGCAGCCAGGAGGCTCCC

TGAGGCTGAGCTGCGCCGCTTCTGGCTACACCGTGTCCAGCTATTGTATGGGCTGGTTCAGGCAGGCTC

CTGGCAAGGGAAGGGAGGGCGTGTCCGCTATCGACAGCGATGGCAGCGTGTCTTACGCCGACAGCGT

GAAGGGCAGATTCACCATCTCTAAGGATAACTCCAAGAATACACTGTACCTGCAGATGAACTCTCTGC

GCGCCGAGGACACCGCCGTGTACTTTTGCGCTGCTGACCTGTGCTGGGTGGACCAGGATCAGGGCGAG

TATAATACATGGGGCCAGGGCACCCTGGTGACAGTGTCTTCC
```

Polypeptide sequence of H9 (SEQ ID NO: 47):
```
EVQLVQSGAEVKKPGASVKVSCKASGYIFTGYGITWVRQAPGQGLEWMGEIFPRRVQTYYSEKF

KGRVTMTTDTSTSTAYMELRSLRSDDTAVYYCARDYDPYFALDYWGQGTTVTVSSASTKGPSV

FPLAPSSKSTSGGTAALGCLVKDYFPEPVTVSWNSGALTSGVHTFPAVLQSSGLYSLSSVVTVPSS

SLGTQTYICNVNHKPSNTKVDKKVEPKSCDKTHTCPPCPAPELLGGPSVFLFPPKPKDTLMISRTP

EVTCVVVDVSHEDPEVKFNWYVDGVEVHNAKTKPREEQYASTYRVVSVLTVLHQDWLNGKEY

KCKVSNKALPAPIEKTISKAKGQPREPQVYTLPPSREEMTKNQVSLTCLVKGFYPSDIAVEWESN

GQPENNYKTTPPVLDSDGSFFLYSKLTVDKSRWQQGNVFSCSVMHEALHNHYTQKSLSLSPGKG

GGGSGGGSEVQLVESGGGLVQPGGSLRLSCAASGYTVSSYCMGWFRQAPGKGREGVSAIDSDG

SVSYADSVKGRFTISKDNSKNTLYLQMNSLRAEDTAVYFCAADLCWVDQDQGEYNTWGQGTL

VTVSS
```

DNA sequence of H10 (SEQ ID NO: 48):
```
GAAGTCCAGCTGGTGCAGAGCGGAGCCGAGGTGAAGAAACCAGGCGCTTCTGTGAAGGTGTCCTGCA

AGGCCTCTGGGTACATCTTCACCGGCTACGGCATCACCTGGGTGCGGCAGGCTCCTGGCCAGGGCCTG

GAATGGATGGGCGAGATCTTTCCCAGGAGAGTGCAGACCTACTACTCCGAGAAGTTCAAGGGCAGAG

TGACCATGACCACCGACACCTCCACCTCTACCGCCTACATGGAACTGCGGTCTCTGAGATCCGATGAC

ACCGCTGTGTACTACTGCGCCAGAGACTACGACCCTTATTTCGCCCTGGATTATTGGGGCCAAGGCAC

CACCGTGACAGTCTCCTCCGCCTCTACCAAGGGCCCTTCCGTGTTCCCCCTGGCCCCTAGCAGCAAGTC

CACATCAGGAGGCACCGCTGCTCTGGGCTGCCTGGTCAAGGACTACTTCCCTGAACCTGTGACCGTGT

CCTGGAACTCCGGCGCCCTGACAAGTGGAGTGCATACCTTCCCCGCCGTGCTGCAGTCCTCTGGCCTGT

ACTCTCTGTCTAGCGTGGTCACTGTGCCTTCCTCTAGCCTCGGCACACAGACATACATCTGCAACGTGA

ACCACAAGCCTTCCAACACCAAAGTGGACAAGAAGGTGGAACCCAAGTCTTGCGACAAAACCCACAC

ATGTCCACCTTGTCCTGCCCCCGAGCTGCTGGGCGGCCCCTCCGTGTTTCTGTTTCCTCCTAAGCCGAA

GGATACACTGATGATCTCCCGGACCCCTGAGGTGACCTGTGTGGTGGTGGACGTGTCTCACGAGGACC

CCGAAGTGAAGTTCAACTGGTACGTGGATGGCGTGGAAGTGCACAATGCTAAGACCAAGCCTAGAGA

AGAGCAGTACGCCTCCACCTACCGGGTGGTCTCTGTGCTGACCGTCCTGCATCAGGACTGGCTGAACG

GCAAAGAGTACAAGTGCAAGGTGTCTAACAAGGCTCTGCCTGCTCCTATCGAGAAAACCATCTCTAAG

GCCAAGGGACAGCCTCGGGAACCACAAGTGTACACCCTGCCTCCTTCTAGAGAGGAGATGACCAAGA

ACCAGGTGAGCCTGACCTGCCTCGTGAAAGGCTTCTACCCCTCTGACATCGCCGTGGAGTGGGAGTCC
```

-continued

AATGGCCAGCCTGAGAACAACTACAAGACCACACCTCCAGTTCTGGACTCCGACGGTTCCTTCTTCCT

GTACTCCAAGCTGACCGTTGATAAGTCCAGATGGCAGCAGGGCAACGTGTTCTCCTGTTCCGTGATGC

ACGAGGCCCTGCACAACCACTACACCCAGAAGTCCCTGAGCTTGTCTCCTGGCAAGGAACCTAAGTCT

AGCGACAAAGGCCATGGAGGTCCCCCTGGACCAGAGGTGCAGCTGGTGGAGTCCGGAGGAGGACTGG

TGCAGCCAGGAGGCTCCCTGAGGCTGAGCTGCGCCGCTTCTGGCTACACCGTGTCCAGCTATTGTATG

GGCTGGTTCAGGCAGGCTCCTGGCAAGGGAAGGGAGGGCGTGTCCGCTATCGACAGCGATGGCAGCG

TGTCTTACGCCGACAGCGTGAAGGGCAGATTCACCATCTCTAAGGATAACTCCAAGAATACACTGTAC

CTGCAGATGAACTCTCTGCGCGCCGAGGACACCGCCGTGTACTTTTGCGCTGCTGACCTGTGCTGGGTG

GACCAGGATCAGGGCGAGTATAATACATGGGGCCAGGGCACCCTGGTGACAGTGTCTTCC

Polypeptide sequence of H10 (SEQ ID NO: 49):
EVQLVQSGAEVKKPGASVKVSCKASGYIFTGYGITWVRQAPGQGLEWMGEIFPRRVQTYYSEKF

KGRVTMTTDTSTSTAYMELRSLRSDDTAVYYCARDYDPYFALDYWGQGTTVTVSSASTKGPSV

FPLAPSSKSTSGGTAALGCLVKDYFPEPVTVSWNSGALTSGVHTFPAVLQSSGLYSLSSVVTVPSS

SLGTQTYICNVNHKPSNTKVDKKVEPKSCDKTHTCPPCPAPELLGGPSVFLFPPKPKDTLMISRTP

EVTCVVVDVSHEDPEVKFNWYVDGVEVHNAKTKPREEQYASTYRVVSVLTVLHQDWLNGKEY

KCKVSNKALPAPIEKTISKAKGQPREPQVYTLPPSREEMTKNQVSLTCLVKGFYPSDIAVEWESN

GQPENNYKTTPPVLDSDGSFFLYSKLTVDKSRWQQGNVFSCSVMHEALHNHYTQKSLSLSPGKE

PKSSDKGHGGPPGPEVQLVESGGGLVQPGGSLRLSCAASGYTVSSYCMGWFRQAPGKGREGVS

AIDSDGSVSYADSVKGRFTISKDNSKNTLYLQMNSLRAEDTAVYFCAADLCWVDQDQGEYNTW

GQGTLVTVSS

DNA sequence of H11 (SEQ ID NO: 50):
GAGGTGCAGCTGGTGGAGTCCGGAGGAGGACTGGTGCAGCCAGGAGGCTCCCTGAGGCTGAGCTGCG

CCGCTTCTGGCTACACCGTGTCCAGCTATTGTATGGGCTGGTTCAGGCAGGCTCCTGGCAAGGGAAGG

GAGGGCGTGTCCGCTATCGACAGCGATGGCAGCGTGTCTTACGCCGACAGCGTGAAGGGCAGATTCAC

CATCTCTAAGGATAACTCCAAGAATACACTGTACCTGCAGATGAACTCTCTGCGCGCCGAGGACACCG

CCGTGTACTTTTGCGCTGCTGACCTGTGCTGGGTGGACCAGGATCAGGGCGAGTATAATACATGGGGC

CAGGGCACCCTGGTGACAGTGTCTTCCGGTGGAGGCGGTAGTGGAGGCGGTGGTTCAGGATCTGAAGT

CCAGCTGGTGCAGAGCGGAGCCGAGGTGAAGAAACCAGGCGCTTCTGTGAAGGTGTCCTGCAAGGCC

TCTGGGTACATCTTCACCGGCTACGGCATCACCTGGGTGCGGCAGGCTCCTGGCCAGGGCCTGGAATG

GATGGGCGAGATCTTTCCCAGGAGAGTGCAGACCTACTACTCCGAGAAGTTCAAGGGCAGAGTGACC

ATGACCACCGACACCTCCACCTCTACCGCCTACATGGAACTGCGGTCTCTGAGATCCGATGACACCGC

TGTGTACTACTGCGCCAGAGACTACGACCCTTATTTCGCCCTGGATTATTGGGGCCAAGGCACCACCGT

GACAGTCTCCTCCGCCTCTACCAAGGGCCCTTCCGTGTTCCCCCTGGCCCCTAGCAGCAAGTCCACATC

AGGAGGCACCGCTGCTCTGGGCTGCCTGGTCAAGGACTACTTCCCTGAACCTGTGACCGTGTCCTGGA

ACTCCGGCGCCCTGACAAGTGGAGTGCATACCTTCCCCGCCGTGCTGCAGTCCTCTGGCCTGTACTCTC

TGTCTAGCGTGGTCACTGTGCCTTCCTCTAGCCTCGGCACACAGACATACATCTGCAACGTGAACCACA

AGCCTTCCAACACCAAAGTGGACAAGAAGGTGGAACCCAAGTCTTGCGACAAAACCCACACATGTCC

ACCTTGTCCTGCCCCCGAGCTGCTGGGCGGCCCCTCCGTGTTTCTGTTTCCTCCTAAGCCGAAGGATAC

ACTGATGATCTCCCGGACCCCTGAGGTGACCTGTGTGGTGGTGGACGTGTCTCACGAGGACCCCGAAG

TGAAGTTCAACTGGTACGTGGATGGCGTGGAAGTGCACAATGCTAAGACCAAGCCTAGAGAAGAGCA

GTACGCCTCCACCTACCGGGTGGTCTCTGTGCTGACCGTCCTGCATCAGGACTGGCTGAACGGCAAAG

AGTACAAGTGCAAGGTGTCTAACAAGGCTCTGCCTGCTCCTATCGAGAAACCCATCTCTAAGGCCAAG

-continued

GGACAGCCTCGGGAACCACAAGTGTACACCCTGCCTCCTTCTAGAGAGGAGATGACCAAGAACCAGG

TGAGCCTGACCTGCCTCGTGAAAGGCTTCTACCCCTCTGACATCGCCGTGGAGTGGGAGTCCAATGGC

CAGCCTGAGAACAACTACAAGACCACACCTCCAGTTCTGGACTCCGACGGTTCCTTCTTCCTGTACTCC

AAGCTGACCGTTGATAAGTCCAGATGGCAGCAGGGCAACGTGTTCTCCTGTTCCGTGATGCACGAGGC

CCTGCACAACCACTACACCCAGAAGTCCCTGAGCTTGTCTCCTGGCAAG

Polypeptide sequence of H11 (SEQ ID NO: 51):
EVQLVESGGGLVQPGGSLRLSCAASGYTVSSYCMGWFRQAPGKGREGVSAIDSDGSVSYADSV

KGRFTISKDNSKNTLYLQMNSLRAEDTAVYFCAADLCWVDQDQGEYNTWGQGTLVTVSSGGG

GSGGGGSGSEVQLVQSGAEVKKPGASVKVSCKASGYIFTGYGITWVRQAPGQGLEWMGEIFPR

RVQTYYSEKFKGRVTMTTDTSTSTAYMELRSLRSDDTAVYYCARDYDPYFALDYWGQGTTVT

VSSASTKGPSVFPLAPSSKSTSGGTAALGCLVKDYFPEPVTVSWNSGALTSGVHTFPAVLQSSGL

YSLSSVVTVPSSSLGTQTYICNVNHKPSNTKVDKKVEPKSCDKTHTCPPCPAPELLGGPSVFLFPP

KPKDTLMISRTPEVTCVVVDVSHEDPEVKFNWYVDGVEVHNAKTKPREEQYASTYRVVSVLTV

LHQDWLNGKEYKCKVSNKALPAPIEKTISKAKGQPREPQVYTLPPSREEMTKNQVSLTCLVKGF

YPSDIAVEWESNGQPENNYKTTPPVLDSDGSFFLYSKLTVDKSRWQQGNVFSCSVMHEALHNH

YTQKSLSLSPGK

DNA sequence of L4 (SEQ ID NO: 52):
GATATCCAGATGACCCAGTCTCCTAGCAGCCTGAGCGCTTCTGTGGGCGACAGAGTGACAATCACCTG

TAGAGCCTCTCAGGACGTGTCCACCGCCGTGGATTGGTACCAGCAGAAGCCCGGCAAGGCTCCTAAGC

TGCTGATCTACTCTGCCTCCTACCGGTACACAGGAGTCCCCGATAGATTCTCTGGCTCCGGCTCTGGAA

CCGACTTCACCTTCACCATCTCCTCTCTGCAGCCTGAGGACATTGCCACCTACTACTGCCAGCAGCACT

ACTCCATCCCTTTTACCTTCGGCCAGGGCACCAAGCTGGAAATCAAGCGGACCGTGGCCGCTCCATCC

GTGTTCATCTTTCCTCCTTCCGACGAGCAGCTGAAGTCTGGCACCGCTTCCGTGGTGTGCCTGCTGAAC

AACTTCTACCCTCGGGAAGCCAAGGTGCAGTGGAAAGTGGACAACGCCCTGCAGTCCGGCAATAGCC

AAGAGTCCGTCACCGAGCAAGACTCCAAGGACTCTACCTATTCTCTCTCCAGCACACTGACCCTGTCTA

AAGCCGACTACGAGAAGCACAAGGTGTACGCCTGCGAAGTGACCCACCAGGGCCTGTCTTCCCCCGTG

ACAAAGTCCTTCAACAGAGGCGAGTGTGAATCGAAGTACGGACCTCCATCTCCACCTAGTCCAGAGGT

GCAGCTGGTGGAGTCCGGAGGAGGACTGGTGCAGCCAGGAGGCTCCCTGAGGCTGAGCTGCGCCGCT

TCTGGCTACACCGTGTCCAGCTATTGTATGGGCTGGTTCAGGCAGGCTCCTGGCAAGGGAAGGGAGGG

CGTGTCCGCTATCGACAGCGATGGCAGCGTGTCTTACGCCGACAGCGTGAAGGGCAGATTCACCATCT

CTAAGGATAACTCCAAGAATACACTGTACCTGCAGATGAACTCTCTGCGCGCCGAGGACACCGCCGTG

TACTTTTGCGCTGCTGACCTGTGCTGGGTGGACCAGGATCAGGGCGAGTATAATACATGGGGCCAGGG

CACCCTGGTGACAGTGTCTTCC

Polypeptide sequence of L4 (SEQ ID NO: 53):
DIQMTQSPSSLSASVGDRVTITCRASQDVSTAVDWYQQKPGKAPKLLIYSASYRYTGVPDRFSGS

GSGTDFTFTISSLQPEDIATYYCQQHYSIPFTFGQGTKLEIKRTVAAPSVFIFPPSDEQLKSGTASVV

CLLNNFYPREAKVQWKVDNALQSGNSQESVTEQDSKDSTYSLSSTLTLSKADYEKHKVYACEV

THQGLSSPVTKSFNRGECESKYGPPSPPSPEVQLVESGGGLVQPGGSLRLSCAASGYTVSSYCMG

WFRQAPGKGREGVSAIDSDGSVSYADSVKGRFTISKDNSKNTLYLQMNSLRAEDTAVYFCAAD

LCWVDQDQGEYNTWGQGTLVTVSS

-continued

DNA sequence of H12 (SEQ ID NO: 54):
GAAGTCCAGCTGGTGCAGAGCGGAGCCGAGGTGAAGAAACCAGGCGCTTCTGTGAAGGTGTCCTGCA

AGGCCTCTGGGTACATCTTCACCGGCTACGGCATCACCTGGGTGCGGCAGGCTCCTGGCCAGGGCCTG

GAATGGATGGGCGAGATCTTTCCCAGGAGAGTGCAGACCTACTACTCCGAGAAGTTCAAGGGCAGAG

TGACCATGACCACCGACACCTCCACCTCTACCGCCTACATGGAACTGCGGTCTCTGAGATCCGATGAC

ACCGCTGTGTACTACTGCGCCAGAGACTACGACCCTTATTTCGCCCTGGATTATTGGGGCCAAGGCAC

CACCGTGACAGTCTCCTCCGCCTCTACCAAGGGCCCTTCCGTGTTCCCCCTGGCCCCTAGCAGCAAGTC

CACATCAGGAGGCACCGCTGCTCTGGGCTGCCTGGTCAAGGACTACTTCCCTGAACCTGTGACCGTGT

CCTGGAACTCCGGCGCCCTGACAAGTGGAGTGCATACCTTCCCCGCCGTGCTGCAGTCCTCTGGCCTGT

ACTCTCTGTCTAGCGTGGTCACTGTGCCTTCCTCTAGCCTCGGCACACAGACATACATCTGCAACGTGA

ACCACAAGCCTTCCAACACCAAAGTGGACAAGAAGGTGGAACCCAAGTCTTGCGACAAAACCCACAC

ATGTCCACCTTGTCCTGCCCCCGAGCTGCTGGGCGGCCCCTCCGTGTTTCTGTTTCCTCCTAAGCCGAA

GGATACACTGATGATCTCCCGGACCCCTGAGGTGACCTGTGTGGTGGTGGACGTGTCTCACGAGGACC

CCGAAGTGAAGTTCAACTGGTACGTGGATGGCGTGGAAGTGCACAATGCTAAGACCAAGCCTAGAGA

AGAGCAGTACGCCTCCACCTACCGGGTGGTCTCTGTGCTGACCGTCCTGCATCAGGACTGGCTGAACG

GCAAAGAGTACAAGTGCAAGGTGTCTAACAAGGCTCTGCCTGCTCCTATCGAGAAAACCATCTCTAAG

GCCAAGGGACAGCCTCGGGAACCACAAGTGTACACCCTGCCTCCTTCTAGAGAGGAGATGACCAAGA

ACCAGGTGAGCCTGACCTGCCTCGTGAAAGGCTTCTACCCCTCTGACATCGCCGTGGAGTGGGAGTCC

AATGGCCAGCCTGAGAACAACTACAAGACCACACCTCCAGTTCTGGACTCCGACGGTTCCTTCTTCCT

GTACTCCAAGCTGACCGTTGATAAGTCCAGATGGCAGCAGGGCAACGTGTTCTCCTGTTCCGTGATGC

ACGAGGCCCTGCACAACCACTACACCCAGAAGTCCCTGAGCTTGTCTCCTGGCAAGGAATCGAAGTAC

GGACCTCCATCTCCACCTAGTCCAGAGGTGCAGCTGGTGGAGTCCGGAGGAGGACTGGTGCAGCCAG

GAGGCTCCCTGAGGCTGAGCTGCGCCGCTTCTGGCTACACCGTGTCCAGCTATTGTATGGGCTGGTTCA

GGCAGGCTCCTGGCAAGGGAAGGGAGGGCGTGTCCGCTATCGACAGCGATGGCAGCGTGTCTTACGC

CGACAGCGTGAAGGGCAGATTCACCATCTCTAAGGATAACTCCAAGAATACACTGTACCTGCAGATGA

ACTCTCTGCGCGCCGAGGACACCGCCGTGTACTTTTGCGCTGCTGACCTGTGCTGGGTGGACCAGGAT

CAGGGCGAGTATAATACATGGGGCCAGGGCACCCTGGTGACAGTGTCTTCC

Polypeptide sequence of H12 (SEQ ID NO: 55):
EVQLVQSGAEVKKPGASVKVSCKASGYIFTGYGITWVRQAPGQGLEWMGEIFPRRVQTYYSEKF

KGRVTMTTDTSTSTAYMELRSLRSDDTAVYYCARDYDPYFALDYWGQGTTVTVSSASTKGPSV

FPLAPSSKSTSGGTAALGCLVKDYFPEPVTVSWNSGALTSGVHTFPAVLQSSGLYSLSSVVTVPSS

SLGTQTYICNVNHKPSNTKVDKKVEPKSCDKTHTCPPCPAPELLGGPSVFLFPPKPKDTLMISRTP

EVTCVVVDVSHEDPEVKFNWYVDGVEVHNAKTKPREEQYASTYRVVSVLTVLHQDWLNGKEY

KCKVSNKALPAPIEKTISKAKGQPREPQVYTLPPSREEMTKNQVSLTCLVKGFYPSDIAVEWESN

GQPENNYKTTPPVLDSDGSFFLYSKLTVDKSRWQQGNVFSCSVMHEALHNHYTQKSLSLSPGKE

SKYGPPSPPSPEVQLVESGGGLVQPGGSLRLSCAASGYTVSSYCMGWFRQAPGKGREGVSAIDS

DGSVSYADSVKGRFTISKDNSKNTLYLQMNSLRAEDTAVYFCAADLCWVDQDQGEYNTWGQG

TLVTVSS

What is claimed is:

1. An isolated anti-PD-L1/anti-LAG-3 multiple antigen binding protein or antigen binding fragment thereof comprising:

(a) a first antigen binding portion comprising a heavy chain variable domain ($V_H$) and a light chain variable domain ($V_L$), wherein:

the $V_H$ and $V_L$ together form an antigen-binding site that specifically binds PD-L1;

the $V_H$ comprises a heavy chain complementarity determining region 1 (HCDR1), HCDR2, and HCDR3 comprising the amino acid sequences of SEQ ID NO:3, SEQ ID NO:4, and SEQ ID NO:5, respectively;

and the $V_L$ comprises a light chain complementarity determining region 1 (LCDR1), LCDR2, and LCDR3 comprising the amino acid sequences of SEQ ID NO:6, SEQ ID NO: 7, and SEQ ID NO:8, respectively; and (b) a second antigen binding portion comprising a single-domain antibody that specifically binds LAG-3, wherein the single-domain antibody comprises a complementarity determining region 1 (CDR1), CDR2, and CDR3 comprising the amino acid sequences of SEQ ID NO:33, SEQ ID NO:34, and SEQ ID NO:35, respectively;

wherein the first antigen binding portion and the second antigen binding portion are fused to each other via a peptide linker comprising the amino acid sequence of SEQ ID NO:12;

wherein the amino (N)-terminus of the second antigen binding portion is fused to the carboxy (C)-terminus of at least one light chain of the first antigen binding portion.

2. The isolated anti-PD-L1/anti-LAG-3 multiple antigen binding protein or antigen binding fragment thereof of claim 1, wherein the first antigen binding portion is a full-length antibody comprising two heavy chains and two light chains.

3. The isolated anti-PD-L1/anti-LAG-3 multiple antigen binding protein or antigen binding fragment thereof of claim 1, wherein the first antigen binding portion is an antibody fragment comprising a heavy chain comprising the $V_H$ and a light chain comprising the $V_L$.

4. The isolated anti-PD-L1/anti-LAG-3 multiple antigen binding protein or antigen binding fragment thereof of claim 1 wherein the heavy chain of the first antigen binding portion comprises an amino acid sequence at least 95% identical to SEQ ID NO:14 or SEQ ID NO:18, and the light chain of the first antigen binding portion comprises an amino acid sequence at least 95% identical to SEQ ID NO:16.

5. The isolated anti-PD-L1/anti-LAG-3 multiple antigen binding protein or antigen binding fragment thereof of claim 1, wherein the second antigen binding portion comprises an amino acid sequence at least 95% identical to an amino acid sequence of SEQ ID NO: 37.

6. The isolated anti-PD-L1/anti-LAG-3 multiple antigen binding protein or antigen binding fragment thereof of claim 1, wherein the first antigen binding portion comprises a human, humanized or chimeric antibody or antigen binding fragment thereof.

7. The isolated anti-PD-L1/anti-LAG-3 multiple antigen binding protein or antigen binding fragment thereof of claim 1, wherein the second antigen binding portion comprising a single-domain antibody that specifically binds LAG-3 is camelid, chimeric, partially humanized, or fully humanized.

8. The isolated anti-PD-L1/anti-LAG-3 multiple antigen binding protein or antigen binding fragment thereof of claim 1, comprising an anti-PD-L1 full-length antibody and an anti-LAG-3 single-domain antibody, wherein:

the N-terminus of the anti-LAG-3 sdAb is fused to the C-terminus of both light chains of the anti-PD-L1 full-length antibody, and wherein the light chain fusion polypeptide comprises the amino acid sequence of SEQ ID NO:20 and the heavy chain polypeptide comprises the amino acid sequence of SEQ ID NO:14 or 18.

9. A pharmaceutical composition comprising the isolated anti-PD-L1/anti-LAG-3 multiple antigen binding protein or antigen binding fragment thereof of claim 1, and a pharmaceutical acceptable carrier.

10. A method of treating a subject having or at risk of having a PD-L1 and/or LAG-3-related cancer, the method comprising administering to the subject an effective amount of the pharmaceutical composition of claim 9.

11. The method of claim 10, wherein the cancer is a solid tumor.

* * * * *

SEQUENCE LISTING

<160> NUMBER OF SEQ ID NOS: 55

<210> SEQ ID NO 1
<211> LENGTH: 57
<212> TYPE: DNA
<213> ORGANISM: Artificial Sequence
<220> FEATURE:
<223> OTHER INFORMATION: Secretory Signal Peptide DNA sequence

<400> SEQUENCE: 1
atgggctggt cctgcatcat cctgttcctg gtggctaccg ccaccggcgt gcactcc          57

<210> SEQ ID NO 2
<211> LENGTH: 19
<212> TYPE: PRT
<213> ORGANISM: Artificial Sequence
<220> FEATURE:
<223> OTHER INFORMATION: Secretory Signal Peptide

<400> SEQUENCE: 2

Met Gly Trp Ser Cys Ile Ile Leu Phe Leu Val Ala Thr Ala Thr Gly
1               5                   10                  15

Val His Ser

<210> SEQ ID NO 3
<211> LENGTH: 10
<212> TYPE: PRT
<213> ORGANISM: Artificial Sequence
<220> FEATURE:
<223> OTHER INFORMATION: PDL1HCv1 HCDR1

<400> SEQUENCE: 3

Gly Tyr Ile Phe Thr Gly Tyr Gly Ile Thr
1               5                   10

<210> SEQ ID NO 4
<211> LENGTH: 17
<212> TYPE: PRT
<213> ORGANISM: Artificial Sequence
<220> FEATURE:
<223> OTHER INFORMATION: PDL1HCv1 HCDR2

<400> SEQUENCE: 4

Glu Ile Phe Pro Arg Arg Val Gln Thr Tyr Tyr Ser Glu Lys Phe Lys
1               5                   10                  15

Gly

<210> SEQ ID NO 5
<211> LENGTH: 10
<212> TYPE: PRT
<213> ORGANISM: Artificial Sequence
<220> FEATURE:
<223> OTHER INFORMATION: PDL1HCv1 HCDR3

<400> SEQUENCE: 5

Asp Tyr Asp Pro Tyr Phe Ala Leu Asp Tyr
1               5                   10

<210> SEQ ID NO 6
<211> LENGTH: 11
<212> TYPE: PRT
<213> ORGANISM: Artificial Sequence
<220> FEATURE:
<223> OTHER INFORMATION: PDL1HCv1 or PDL1HCv5 LCDR1

-continued

<400> SEQUENCE: 6

Arg Ala Ser Gln Asp Val Ser Thr Ala Val Asp
1               5                   10

<210> SEQ ID NO 7
<211> LENGTH: 7
<212> TYPE: PRT
<213> ORGANISM: Artificial Sequence
<220> FEATURE:
<223> OTHER INFORMATION: PDL1HCv1 or PDL1HCv5 LCDR2

<400> SEQUENCE: 7

Ser Ala Ser Tyr Arg Tyr Thr
1               5

<210> SEQ ID NO 8
<211> LENGTH: 9
<212> TYPE: PRT
<213> ORGANISM: Artificial Sequence
<220> FEATURE:
<223> OTHER INFORMATION: PDL1HCv1 or PDL1HCv5 LCDR3

<400> SEQUENCE: 8

Gln Gln His Tyr Ser Ile Pro Phe Thr
1               5

<210> SEQ ID NO 9
<211> LENGTH: 10
<212> TYPE: PRT
<213> ORGANISM: Artificial Sequence
<220> FEATURE:
<223> OTHER INFORMATION: PDL1HCv5 HCDR1

<400> SEQUENCE: 9

Gly Tyr Ile Phe Thr Gly Tyr Gly Ile Thr
1               5                   10

<210> SEQ ID NO 10
<211> LENGTH: 17
<212> TYPE: PRT
<213> ORGANISM: Artificial Sequence
<220> FEATURE:
<223> OTHER INFORMATION: PDL1HCv5 HCDR2

<400> SEQUENCE: 10

Glu Ile Phe Pro Arg Arg Val Gln Thr Tyr Tyr Ser Glu Lys Phe Lys
1               5                   10                  15

Gly

<210> SEQ ID NO 11
<211> LENGTH: 10
<212> TYPE: PRT
<213> ORGANISM: Artificial Sequence
<220> FEATURE:
<223> OTHER INFORMATION: PDL1HCv5 HCDR3

<400> SEQUENCE: 11

Asp Tyr Asp Pro Tyr Phe Ala Leu Asp Tyr
1               5                   10

<210> SEQ ID NO 12
<211> LENGTH: 15
<212> TYPE: PRT
<213> ORGANISM: Artificial Sequence
<220> FEATURE:

-continued

<223> OTHER INFORMATION: Peptide E-Linker

<400> SEQUENCE: 12

Glu Pro Lys Ser Ser Asp Lys Thr His Thr Ser Pro Pro Ser Pro
1               5                   10                  15

<210> SEQ ID NO 13
<211> LENGTH: 1347
<212> TYPE: DNA
<213> ORGANISM: Artificial Sequence
<220> FEATURE:
<223> OTHER INFORMATION: PDL1HCv1 Heavy Chain

<400> SEQUENCE: 13
gaagtccagc tggtgcagag cggagccgag gtgaagaaac caggcgcttc tgtgaaggtg      60
tcctgcaagg cctctgggta catcttcacc ggctacggca tcacctgggt gcggcaggct     120
cctggccagg gcctggaatg gatgggcgag atctttccca ggagagtgca gacctactac     180
tccgagaagt tcaagggcag agtgaccatg accaccgaca cctccacctc taccgcctac     240
atggaactgc ggtctctgag atccgatgac accgctgtgt actactgcgc cagagactac     300
gacccttatt tcgccctgga ttattggggc caaggcacca ccgtgacagt ctcctccgcc     360
tctaccaagg gcccttccgt gttccccctg gcccctagca gcaagtccac atcaggaggc     420
accgctgctc tgggctgcct ggtcaaggac tacttccctg aacctgtgac cgtgtcctgg     480
aactccggcg ccctgacaag tggagtgcat accttccccg ccgtgctgca gtcctctggc     540
ctgtactctc tgtctagcgt ggtcactgtg ccttcctcta gcctcggcac acagacatac     600
atctgcaacg tgaaccacaa gccttccaac accaaagtgg acaagaaggt ggaacccaag     660
tcttgcgaca aaacccacac atgtccacct tgtcctgccc ccgagctgct gggcggcccc     720
tccgtgtttc tgtttcctcc taagcccgaag gatacactga tgatctcccg gacccctgag     780
gtgacctgtg tggtggtgga cgtgtctcac gaggaccccg aagtgaagtt caactggtac     840
gtggatggcg tggaagtgca caatgctaag accaagccta gaagagagca gtacgcctcc     900
acctaccggg tggtctctgt gctgaccgtc ctgcatcagg actggctgaa cggcaaagag     960
tacaagtgca aggtgtctaa caaggctctg cctgctccta tcgagaaaac catctctaag    1020
gccaagggac agcctcggga accacaagtg tacaccctgc ctccttctag agaggagatg    1080
accaagaacc aggtgagcct gacctgcctc gtgaaaggct tctacccctc tgacatcgcc    1140
gtggagtggg agtccaatgg ccagcctgag aacaactaca gaccacacc tccagttctg    1200 gactccgacg gttccttctt cctgtactcc aagctgaccg ttgataagtc cagatggcag    1260
cagggcaacg tgttctcctg ttccgtgatg cacgaggccc tgcacaacca ctacacccag    1320
aagtccctga gcttgtctcc tggcaag                                        1347

<210> SEQ ID NO 14
<211> LENGTH: 449
<212> TYPE: PRT
<213> ORGANISM: Artificial Sequence
<220> FEATURE:
<223> OTHER INFORMATION: PDL1HCv1 Heavy Chain

<400> SEQUENCE: 14

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
                20                  25                  30

-continued

```
Gly Ile Thr Trp Val Arg Gln Ala Pro Gly Gln Gly Leu Glu Trp Met
    35                  40                  45

Gly Glu Ile Phe Pro Arg Arg Val Gln Thr Tyr Tyr Ser Glu Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys
```

-continued

<210> SEQ ID NO 15
<211> LENGTH: 642
<212> TYPE: DNA
<213> ORGANISM: Artificial Sequence
<220> FEATURE:
<223> OTHER INFORMATION: PDL1HCv1 or PDL1HCv5 Light Chain

<400> SEQUENCE: 15
gatatccaga tgacccagtc tcctagcagc ctgagcgctt ctgtgggcga cagagtgaca      60
atcacctgta gagcctctca ggacgtgtcc accgccgtgg attggtacca gcagaagccc     120
ggcaaggctc ctaagctgct gatctactct gcctcctacc ggtacacagg agtccccgat     180
agattctctg gctccggctc tggaaccgac ttcaccttca ccatctcctc tctgcagcct     240
gaggacattg ccacctacta ctgccagcag cactactcca tccctttac cttcggccag      300 ggcaccaagc tggaaatcaa gcggaccgtg gccgctccat ccgtgttcat ctttcctcct     360
tccgacgagc agctgaagtc tggcaccgct tccgtggtgt gcctgctgaa caacttctac     420
cctcgggaag ccaaggtgca gtggaaagtg gacaacgccc tgcagtccgg caatagccaa     480
gagtccgtca ccgagcaaga ctccaaggac tctacctatt ctctctccag cacactgacc     540
ctgtctaaag ccgactacga gaagcacaag gtgtacgcct gcgaagtgac ccaccagggc     600
ctgtcttccc ccgtgacaaa gtccttcaac agaggcgagt gt                        642

<210> SEQ ID NO 16
<211> LENGTH: 214
<212> TYPE: PRT
<213> ORGANISM: Artificial Sequence
<220> FEATURE:
<223> OTHER INFORMATION: PDL1HCv1 or PDL1HCv5 Light Chain

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
                20                  25                  30

Val Asp Trp Tyr Gln Gln Lys Pro Gly Lys Ala Pro Lys Leu Leu Ile
            35                  40                  45

Tyr Ser Ala Ser Tyr Arg Tyr Thr Gly Val Pro Asp Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Ile Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

```
Ala Cys Glu Val Thr His Gln Gly Leu Ser Ser Pro Val Thr Lys Ser
        195                 200                 205

Phe Asn Arg Gly Glu Cys
    210

<210> SEQ ID NO 17
<211> LENGTH: 1347
<212> TYPE: DNA
<213> ORGANISM: Artificial Sequence
<220> FEATURE:
<223> OTHER INFORMATION: PDL1HCv5 Heavy Chain

<400> SEQUENCE: 17
gaagtccagc tggtgcagag cggagccgag gtgaagaaac caggcgcttc tgtgaaggtg      60
tcctgcaagg cctctgggta catcttcacc ggctacggca tcacctgggt gcggcaggct     120
cctggccagg gcctggaatg gatgggcgag atctttccca ggagagtgca gacctactac     180
tccgagaagt tcaagggcag agtgaccatg accgctgaca cctccacctc taccgcctac     240
atggaactgc ggtctctgag atccgatgac accgctgtgt actactgcgc cagagactac     300
gacccttatt tcgccctgga ttattggggc caaggcacca ccgtgacagt ctcctccgcc     360
tctaccaagg gcccttccgt gttccccctg gcccctagca gcaagtccac atcaggaggc     420
accgctgctc tgggctgcct ggtcaaggac tacttccctg aacctgtgac cgtgtcctgg     480
aactccggcg ccctgacaag tggagtgcat accttccccg ccgtgctgca gtcctctggc     540
ctgtactctc tgtctagcgt ggtcactgtg ccttcctcta gcctcggcac acagacatac     600
atctgcaacg tgaaccacaa gccttccaac accaaagtgg acaagaaggt ggaacccaag     660
tcttgcgaca aaacccacac atgtccacct tgtcctgccc ccgagctgct gggcggcccc     720
tccgtgtttc tgtttcctcc taagccgaag gatacactga tgatctcccg gacccctgag     780
gtgacctgtg tggtggtgga cgtgtctcac gaggaccccg aagtgaagtt caactggtac     840
gtggatggcg tggaagtgca caatgctaag accaagccta gagaagagca gtacgcctcc     900
acctaccggg tggtctctgt gctgaccgtc ctgcatcagg actggctgaa cggcaaagag     960
tacaagtgca aggtgtctaa caaggctctg cctgctccta tcgagaaaac catctctaag    1020
gccaagggac agcctcggga accacaagtg tacaccctgc ctccttctag agaggagatg    1080
accaagaacc aggtgagcct gacctgcctc gtgaaaggct tctacccctc tgacatcgcc    1140
gtggagtggg agtccaatgg ccagcctgag aacaactaca gaccacacc tccagttctg    1200 gactccgacg gttccttctt cctgtactcc aagctgaccg ttgataagtc cagatggcag    1260
cagggcaacg tgttctcctg ttccgtgatg cacgaggccc tgcacaacca ctacacccag    1320
aagtccctga gcttgtctcc tggcaag                                        1347

<210> SEQ ID NO 18
<211> LENGTH: 449
<212> TYPE: PRT
<213> ORGANISM: Artificial Sequence
<220> FEATURE:
<223> OTHER INFORMATION: PDL1HCv5 Heavy Chain

<400> SEQUENCE: 18

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
            20                  25                  30
```

-continued

```
Gly Ile Thr Trp Val Arg Gln Ala Pro Gly Gln Gly Leu Glu Trp Met
        35                  40                  45

Gly Glu Ile Phe Pro Arg Arg Val Gln Thr Tyr Tyr Ser Glu Lys Phe
        50                  55                  60

Lys Gly Arg Val Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
                100                 105                 110

Thr Thr Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Ala Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430
```

```
Ala Leu His Asn His Tyr Thr Gln Lys Ser Leu Ser Leu Ser Pro Gly
        435                 440                 445

Lys
```

<210> SEQ ID NO 19
<211> LENGTH: 1053
<212> TYPE: DNA
<213> ORGANISM: Artificial Sequence
<220> FEATURE:
<223> OTHER INFORMATION: L2

<400> SEQUENCE: 19

```
gatatccaga tgacccagtc tcctagcagc ctgagcgctt ctgtgggcga cagagtgaca      60
atcacctgta gagcctctca ggacgtgtcc accgccgtgg attggtacca gcagaagccc     120
ggcaaggctc ctaagctgct gatctactct gcctcctacc ggtacacagg agtccccgat     180
agattctctg gctccggctc tggaaccgac ttcaccttca ccatctcctc tctgcagcct     240
gaggacattg ccacctacta ctgccagcag cactactcca tcccttttac cttcggccag     300
ggcaccaagc tggaaatcaa gcggaccgtg gccgctccat ccgtgttcat ctttcctcct     360
tccgacgagc agctgaagtc tggcaccgct tccgtggtgt gcctgctgaa caacttctac     420
cctcgggaag ccaaggtgca gtggaaagtg gacaacgccc tgcagtccgg caatagccaa     480
gagtccgtca ccgagcaaga ctccaaggac tctacctatt ctctctccag cacactgacc     540
ctgtctaaag ccgactacga gaagcacaag gtgtacgcct gcgaagtgac ccaccagggc     600
ctgtcttccc ccgtgacaaa gtccttcaac agaggcgagt gtgaacctaa gtctagcgac     660
aaaactcata ccagcccccc tagtccagag gtgcagctgg tggagtccgg aggaggactg     720
gtgcagccag gaggctccct gaggctgagc tgcgccgctt ctggctacac cgtgtccagc     780
tattgtatgg gctggttcag gcaggctcct ggcaagggaa gggagggcgt gtccgctatc     840
gacagcgatg gcagcgtgtc ttacgccgac agcgtgaagg gcagattcac catctctaag     900
gataactcca gaatacact gtacctgcag atgaactctc tgcgcgccga ggacaccgcc     960
gtgtactttt gcgctgctga cctgtgctgg gtggaccagg atcagggcga gtataataca    1020
tggggccagg gcaccctggt gacagtgtct tcc                                 1053
```

<210> SEQ ID NO 20
<211> LENGTH: 351
<212> TYPE: PRT
<213> ORGANISM: Artificial Sequence
<220> FEATURE:
<223> OTHER INFORMATION: L2

<400> SEQUENCE: 20

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Asp Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Ile Pro Phe
                85                  90                  95
```

```
Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys Glu Pro Lys Ser Ser Asp Lys Thr His Thr
            210                 215                 220

Ser Pro Pro Ser Pro Glu Val Gln Leu Val Glu Ser Gly Gly Gly Leu
225                 230                 235                 240

Val Gln Pro Gly Gly Ser Leu Arg Leu Ser Cys Ala Ala Ser Gly Tyr
                245                 250                 255

Thr Val Ser Ser Tyr Cys Met Gly Trp Phe Arg Gln Ala Pro Gly Lys
                260                 265                 270

Gly Arg Glu Gly Val Ser Ala Ile Asp Ser Asp Gly Ser Val Ser Tyr
                275                 280                 285

Ala Asp Ser Val Lys Gly Arg Phe Thr Ile Ser Lys Asp Asn Ser Lys
            290                 295                 300

Asn Thr Leu Tyr Leu Gln Met Asn Ser Leu Arg Ala Glu Asp Thr Ala
305                 310                 315                 320

Val Tyr Phe Cys Ala Ala Asp Leu Cys Trp Val Asp Gln Asp Gln Gly
                325                 330                 335

Glu Tyr Asn Thr Trp Gly Gln Gly Thr Leu Val Thr Val Ser Ser
                340                 345                 350
```

<210> SEQ ID NO 21
<211> LENGTH: 1758
<212> TYPE: DNA
<213> ORGANISM: Artificial Sequence
<220> FEATURE:
<223> OTHER INFORMATION: H3

<400> SEQUENCE: 21

```
gaggtgcagc tggtggagtc cggaggagga ctggtgcagc caggaggctc cctgaggctg      60
agctgcgccg cttctggcta caccgtgtcc agctattgta tgggctggtt caggcaggct     120
cctggcaagg gaagggaggg cgtgtccgct atcgacagcg atggcagcgt gtcttacgcc     180
gacagcgtga aggcagatt caccatctct aaggataact ccaagaatac actgtacctg     240
cagatgaact ctctgcgcgc cgaggacacc gccgtgtact tttgcgctgc tgacctgtgc     300
tgggtggacc aggatcaggg cgagtataat acatggggcc agggcaccct ggtgacagtg     360
tcttccgaac ctaagtctag cgacaaaact cataccagcc ccctagtccc agaagtccag     420
ctggtgcaga gcggagccga ggtgaagaaa ccaggcgctt ctgtgaaggt gtcctgcaag     480
gcctctgggt acatcttcac cggctacggc atcacctggg tgcggcaggc tcctggccag     540
ggcctggaat ggatgggcga gatctttccc aggagagtgc agacctacta ctccgagaag     600
```

-continued

```
ttcaagggca gagtgaccat gaccaccgac acctccacct ctaccgccta catggaactg      660
cggtctctga gatccgatga caccgctgtg tactactgcg ccagagacta cgacccttat      720
ttcgccctgg attattgggg ccaaggcacc accgtgacag tctcctccgc ctctaccaag      780
ggcccttccg tgttccccct ggcccctagc agcaagtcca catcaggagg caccgctgct      840
ctgggctgcc tggtcaagga ctacttccct gaacctgtga ccgtgtcctg gaactccggc      900
gccctgacaa gtggagtgca taccttcccc gccgtgctgc agtcctctgg cctgtactct      960
ctgtctagcg tggtcactgt gccttcctct agcctcggca cacagacata catctgcaac     1020
gtgaaccaca gccttccaa caccaaagtg gacaagaagg tggaacccaa gtcttgcgac     1080
aaaacccaca catgtccacc ttgtcctgcc cccgagctgc tgggcggccc ctccgtgttt     1140
ctgtttcctc ctaagccgaa ggatacactg atgatctccc ggacccctga ggtgacctgt     1200
gtggtggtgg acgtgtctca cgaggacccc gaagtgaagt tcaactggta cgtggatggc     1260
gtggaagtgc acaatgctaa gaccaagcct agagaagagc agtacgcctc cacctaccgg     1320
gtggtctctg tgctgaccgt cctgcatcag gactggctga cggcaaaga gtacaagtgc      1380 aaggtgtcta caaaggctct gcctgctcct atcgagaaaa ccatctctaa ggccaaggga     1440
cagcctcggg aaccacaagt gtacaccctg cctccttcta gagaggagat gaccaagaac     1500
caggtgagcc tgacctgcct cgtgaaaggc ttctacccct ctgacatcgc cgtggagtgg     1560
gagtccaatg gccagcctga gaacaactac aagaccacac tccagttct ggactccgac      1620 ggttccttct tcctgtactc caagctgacc gttgataagt ccagatggca gcagggcaac     1680
gtgttctcct gttccgtgat gcacgaggcc ctgcacaacc actacaccca gaagtccctg     1740
agcttgtctc ctggcaag                                                    1758
```

```
<210> SEQ ID NO 22
<211> LENGTH: 586
<212> TYPE: PRT
<213> ORGANISM: Artificial Sequence
<220> FEATURE:
<223> OTHER INFORMATION: H3

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Val Ser Ser Tyr
            20                  25                  30

Cys Met Gly Trp Phe Arg Gln Ala Pro Gly Lys Gly Arg Glu Gly Val
        35                  40                  45

Ser Ala Ile Asp Ser Asp Gly Ser Val Ser Tyr Ala Asp Ser Val Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Phe Cys Ala
                85                  90                  95

Ala Asp Leu Cys Trp Val Asp Gln Asp Gln Gly Glu Tyr Asn Thr Trp
            100                 105                 110

Gly Gln Gly Thr Leu Val Thr Val Ser Ser Glu Pro Lys Ser Ser Asp
        115                 120                 125

Lys Thr His Thr Ser Pro Pro Ser Pro Glu Val Gln Leu Val Gln Ser
    130                 135                 140

Gly Ala Glu Val Lys Lys Pro Gly Ala Ser Val Lys Val Ser Cys Lys
145                 150                 155                 160
```

-continued

```
Ala Ser Gly Tyr Ile Phe Thr Gly Tyr Gly Ile Thr Trp Val Arg Gln
            165                 170                 175

Ala Pro Gly Gln Gly Leu Glu Trp Met Gly Glu Ile Phe Pro Arg Arg
            180                 185                 190

Val Gln Thr Tyr Tyr Ser Glu Lys Phe Lys Gly Arg Val Thr Met Thr
            195                 200                 205

Thr Asp Thr Ser Thr Ser Thr Ala Tyr Met Glu Leu Arg Ser Leu Arg
    210                 215                 220

Ser Asp Asp Thr Ala Val Tyr Tyr Cys Ala Arg Asp Tyr Asp Pro Tyr
225                 230                 235                 240

Phe Ala Leu Asp Tyr Trp Gly Gln Gly Thr Thr Val Thr Val Ser Ser
            245                 250                 255

Ala Ser Thr Lys Gly Pro Ser Val Phe Pro Leu Ala Pro Ser Ser Lys
            260                 265                 270

Ser Thr Ser Gly Gly Thr Ala Ala Leu Gly Cys Leu Val Lys Asp Tyr
            275                 280                 285

Phe Pro Glu Pro Val Thr Val Ser Trp Asn Ser Gly Ala Leu Thr Ser
    290                 295                 300

Gly Val His Thr Phe Pro Ala Val Leu Gln Ser Ser Gly Leu Tyr Ser
305                 310                 315                 320

Leu Ser Ser Val Val Thr Val Pro Ser Ser Ser Leu Gly Thr Gln Thr
            325                 330                 335

Tyr Ile Cys Asn Val Asn His Lys Pro Ser Asn Thr Lys Val Asp Lys
            340                 345                 350

Lys Val Glu Pro Lys Ser Cys Asp Lys Thr His Thr Cys Pro Pro Cys
            355                 360                 365

Pro Ala Pro Glu Leu Leu Gly Gly Pro Ser Val Phe Leu Phe Pro Pro
    370                 375                 380

Lys Pro Lys Asp Thr Leu Met Ile Ser Arg Thr Pro Glu Val Thr Cys
385                 390                 395                 400

Val Val Val Asp Val Ser His Glu Asp Pro Glu Val Lys Phe Asn Trp
            405                 410                 415

Tyr Val Asp Gly Val Glu Val His Asn Ala Lys Thr Lys Pro Arg Glu
            420                 425                 430

Glu Gln Tyr Ala Ser Thr Tyr Arg Val Val Ser Val Leu Thr Val Leu
            435                 440                 445

His Gln Asp Trp Leu Asn Gly Lys Glu Tyr Lys Cys Lys Val Ser Asn
    450                 455                 460

Lys Ala Leu Pro Ala Pro Ile Glu Lys Thr Ile Ser Lys Ala Lys Gly
465                 470                 475                 480

Gln Pro Arg Glu Pro Gln Val Tyr Thr Leu Pro Pro Ser Arg Glu Glu
            485                 490                 495

Met Thr Lys Asn Gln Val Ser Leu Thr Cys Leu Val Lys Gly Phe Tyr
            500                 505                 510

Pro Ser Asp Ile Ala Val Glu Trp Glu Ser Asn Gly Gln Pro Glu Asn
            515                 520                 525

Asn Tyr Lys Thr Thr Pro Pro Val Leu Asp Ser Asp Gly Ser Phe Phe
    530                 535                 540

Leu Tyr Ser Lys Leu Thr Val Asp Lys Ser Arg Trp Gln Gln Gly Asn
545                 550                 555                 560

Val Phe Ser Cys Ser Val Met His Glu Ala Leu His Asn His Tyr Thr
            565                 570                 575
```

-continued

Gln Lys Ser Leu Ser Leu Ser Pro Gly Lys
          580                     585

<210> SEQ ID NO 23
<211> LENGTH: 1758
<212> TYPE: DNA
<213> ORGANISM: Artificial Sequence
<220> FEATURE:
<223> OTHER INFORMATION: H4

<400> SEQUENCE: 23

```
gaagtccagc tggtgcagag cggagccgag gtgaagaaac caggcgcttc tgtgaaggtg      60
tcctgcaagg ccctctgggta catcttcacc ggctacggca tcacctgggt gcggcaggct     120
cctggccagg gcctggaatg gatgggcgag atctttccca ggagagtgca gacctactac     180
tccgagaagt tcaagggcag agtgaccatg accaccgaca cctccacctc taccgcctac     240
atggaactgc ggtctctgag atccgatgac accgctgtgt actactgcgc cagagactac     300
gacccttatt tcgccctgga ttattggggc caaggcacca ccgtgacagt ctcctccgcc     360
tctaccaagg gcccttccgt gttccccctg gcccctagca gcaagtccac atcaggaggc     420
accgctgctc tgggctgcct ggtcaaggac tacttccctg aacctgtgac cgtgtcctgg     480
aactccggcg ccctgacaag tggagtgcat accttccccg ccgtgctgca gtcctctggc     540
ctgtactctc tgtctagcgt ggtcactgtg ccttcctcta gcctcggcac acagacatac     600
atctgcaacg tgaaccacaa gccttccaac accaaagtgg acaagaaggt ggaacccaag     660
tcttgcgaca aaacccacac atgtccacct tgtcctgccc ccgagctgct gggcggcccc     720
tccgtgtttc tgtttcctcc taagccgaag gatacactga tgatctcccg gacccctgag     780
gtgacctgtg tggtggtgga cgtgtctcac gaggaccccg aagtgaagtt caactggtac     840
gtggatggcg tggaagtgca caatgctaag accaagccta gaagagca gtacgcctcc     900 acctaccggg tggtctctgt gctgaccgtc ctgcatcagg actggctgaa cggcaaagag     960
tacaagtgca aggtgtctaa caaggctctg cctgctccta tcgagaaaac catctctaag    1020
gccaagggac agcctcggga accacaagtg tacaccctgc ctccttctag agaggagatg    1080
accaagaacc aggtgagcct gacctgcctc gtgaaaggct tctacccctc tgacatcgcc    1140
gtggagtggg agtccaatgg ccagcctgag aacaactaca agaccacacc tccagttctg    1200
gactccgacg gttccttctt cctgtactcc aagctgaccg ttgataagtc cagatggcag    1260
cagggcaacg tgttctcctg ttccgtgatg cacgaggccc tgcacaacca ctacacccag    1320
aagtccctga gcttgtctcc tggcaaggaa cctaagtcta gcgacaaaac tcataccagc    1380 cccctagtc cagaggtgca gctggtggag tccggaggag gactggtgca gccaggaggc    1440
tccctgaggc tgagctgcgc cgcttctggc tacaccgtgt ccagctattg tatgggctgg    1500
ttcaggcagg ctcctggcaa gggaagggag ggcgtgtccg ctatcgacag cgatggcagc    1560
gtgtcttacg ccgacagcgt gaagggcaga ttcaccatct ctaaggataa ctccaagaat    1620
acactgtacc tgcagatgaa ctctctgcgc gccgaggaca ccgccgtgta cttttgcgct    1680
gctgacctgt gctgggtgga ccaggatcag ggcgagtata atacatgggg ccagggcacc    1740
ctggtgacag tgtcttcc                                                    1758
```

<210> SEQ ID NO 24
<211> LENGTH: 586
<212> TYPE: PRT
<213> ORGANISM: Artificial Sequence
<220> FEATURE:

<223> OTHER INFORMATION: H4

<400> SEQUENCE: 24

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
                20                  25                  30

Gly Ile Thr Trp Val Arg Gln Ala Pro Gly Gln Gly Leu Glu Trp Met
            35                  40                  45

Gly Glu Ile Phe Pro Arg Arg Val Gln Thr Tyr Tyr Ser Glu Lys Phe
        50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Ala Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400
```

-continued

```
Asp Ser Asp Gly Ser Phe Phe Leu Tyr Ser Lys Leu Thr Val Asp Lys
                405                     410                     415

Ser Arg Trp Gln Gln Gly Asn Val Phe Ser Cys Ser Val Met His Glu
            420                     425                 430

Ala Leu His Asn His Tyr Thr Gln Lys Ser Leu Ser Leu Ser Pro Gly
            435                     440                 445

Lys Glu Pro Lys Ser Ser Asp Lys Thr His Thr Ser Pro Pro Ser Pro
    450                     455                 460

Glu Val Gln Leu Val Glu Ser Gly Gly Gly Leu Val Gln Pro Gly Gly
465                     470                 475                     480

Ser Leu Arg Leu Ser Cys Ala Ala Ser Gly Tyr Thr Val Ser Ser Tyr
                485                     490                     495

Cys Met Gly Trp Phe Arg Gln Ala Pro Gly Lys Gly Arg Glu Gly Val
                500                     505                 510

Ser Ala Ile Asp Ser Asp Gly Ser Val Ser Tyr Ala Asp Ser Val Lys
                515                     520                 525

Gly Arg Phe Thr Ile Ser Lys Asp Asn Ser Lys Asn Thr Leu Tyr Leu
        530                     535                 540

Gln Met Asn Ser Leu Arg Ala Glu Asp Thr Ala Val Tyr Phe Cys Ala
545                     550                     555                     560

Ala Asp Leu Cys Trp Val Asp Gln Asp Gln Gly Glu Tyr Asn Thr Trp
                565                     570                 575

Gly Gln Gly Thr Leu Val Thr Val Ser Ser
                580                     585
```

<210> SEQ ID NO 25
<211> LENGTH: 1758
<212> TYPE: DNA
<213> ORGANISM: Artificial Sequence
<220> FEATURE:
<223> OTHER INFORMATION: H5

<400> SEQUENCE: 25

```
gaggtgcagc tggtggagtc cggaggagga ctggtgcagc caggaggctc cctgaggctg      60
agctgcgccg cttctggcta caccgtgtcc agctattgta tgggctggtt caggcaggct     120
cctggcaagg gaagggaggg cgtgtccgct atcgacagcg atggcagcgt gtcttacgcc     180
gacagcgtga aggcagatt caccatctct aaggataact ccaagaatac actgtacctg      240
cagatgaact ctctgcgcgc cgaggacacc gccgtgtact tttgcgctgc tgacctgtgc     300
tgggtggacc aggatcaggg cgagtataat acatggggcc agggcaccct ggtgacagtg     360
tcttccgaac ctaagtctag cgacaaaact cataccagcc ccctagtcc agaagtccag       420 ctggtgcaga gcggagccga ggtgaagaaa ccaggcgctt ctgtgaaggt gtcctgcaag     480
gcctctgggt acatcttcac cggctacggc atcacctggg tgcggcaggc tcctggccag     540
ggcctggaat ggatgggcga gatctttccc aggagagtgc agacctacta ctccgagaag     600
ttcaagggca gagtgaccat gaccgctgac acctccacct ctaccgccta catggaactg     660
cggtctctga gatccgatga caccgctgtg tactactgcg ccagagacta cgacccttat     720
ttcgccctgg attattgggg ccaaggcacc accgtgacag tctcctccgc tctaccaag      780 ggcccttccg tgttccccct ggccctagc agcaagtcca tcaggagg caccgctgct        840 ctgggctgcc tggtcaagga ctacttccct gaacctgtga ccgtgtcctg gaactccggc     900
gccctgacaa gtggagtgca taccttcccc gccgtgctgc agtcctctgg cctgtactct     960
ctgtctagcg tggtcactgt gccttcctct agcctcggca cacagacata catctgcaac    1020
```

```
gtgaaccaca agccttccaa caccaaagtg gacaagaagg tggaacccaa gtcttgcgac      1080
aaaacccaca catgtccacc ttgtcctgcc cccgagctgc tgggcggccc ctccgtgttt      1140
ctgtttcctc ctaagccgaa ggatacactg atgatctccc ggacccctga ggtgacctgt      1200
gtggtggtgg acgtgtctca cgaggacccc gaagtgaagt tcaactggta cgtggatggc      1260
gtggaagtgc acaatgctaa gaccaagcct agagaagagc agtacgcctc cacctaccgg      1320
gtggtctctg tgctgaccgt cctgcatcag gactggctga acggcaaaga gtacaagtgc      1380
aaggtgtcta acaaggctct gcctgctcct atcgagaaaa ccatctctaa ggccaaggga      1440
cagcctcggg aaccacaagt gtacaccctg cctccttcta gagaggagat gaccaagaac      1500
caggtgagcc tgacctgcct cgtgaaaggc ttctacccct ctgacatcgc cgtggagtgg      1560
gagtccaatg gccagcctga gaacaactac aagaccacac tccagttct ggactccgac      1620 ggttccttct tcctgtactc caagctgacc gttgataagt ccagatggca gcaggcaac       1680 gtgttctcct gttccgtgat gcacgaggcc ctgcacaacc actacaccca gaagtccctg      1740
agcttgtctc ctggcaag                                                    1758
```

<210> SEQ ID NO 26
<211> LENGTH: 586
<212> TYPE: PRT
<213> ORGANISM: Artificial Sequence
<220> FEATURE:
<223> OTHER INFORMATION: H5

<400> SEQUENCE: 26

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Val Ser Ser Tyr
            20                  25                  30

Cys Met Gly Trp Phe Arg Gln Ala Pro Gly Lys Gly Arg Glu Gly Val
        35                  40                  45

Ser Ala Ile Asp Ser Asp Gly Ser Val Ser Tyr Ala Asp Ser Val Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Phe Cys Ala
                85                  90                  95

Ala Asp Leu Cys Trp Val Asp Gln Asp Gln Gly Glu Tyr Asn Thr Trp
            100                 105                 110

Gly Gln Gly Thr Leu Val Thr Val Ser Ser Glu Pro Lys Ser Ser Asp
        115                 120                 125

Lys Thr His Thr Ser Pro Pro Ser Pro Glu Val Gln Leu Val Gln Ser
    130                 135                 140

Gly Ala Glu Val Lys Lys Pro Gly Ala Ser Val Lys Val Ser Cys Lys
145                 150                 155                 160

Ala Ser Gly Tyr Ile Phe Thr Gly Tyr Gly Ile Thr Trp Val Arg Gln
                165                 170                 175

Ala Pro Gly Gln Gly Leu Glu Trp Met Gly Glu Ile Phe Pro Arg Arg
            180                 185                 190

Val Gln Thr Tyr Tyr Ser Glu Lys Phe Lys Gly Arg Val Thr Met Thr
        195                 200                 205

Ala Asp Thr Ser Thr Ser Thr Ala Tyr Met Glu Leu Arg Ser Leu Arg
    210                 215                 220
```

-continued

Ser Asp Asp Thr Ala Val Tyr Tyr Cys Ala Arg Asp Tyr Asp Pro Tyr
225                 230                 235                 240

Phe Ala Leu Asp Tyr Trp Gly Gln Gly Thr Thr Val Thr Val Ser Ser
                245                 250                 255

Ala Ser Thr Lys Gly Pro Ser Val Phe Pro Leu Ala Pro Ser Ser Lys
                260                 265                 270

Ser Thr Ser Gly Gly Thr Ala Ala Leu Gly Cys Leu Val Lys Asp Tyr
                275                 280                 285

Phe Pro Glu Pro Val Thr Val Ser Trp Asn Ser Gly Ala Leu Thr Ser
                290                 295                 300

Gly Val His Thr Phe Pro Ala Val Leu Gln Ser Ser Gly Leu Tyr Ser
305                 310                 315                 320

Leu Ser Ser Val Val Thr Val Pro Ser Ser Ser Leu Gly Thr Gln Thr
                325                 330                 335

Tyr Ile Cys Asn Val Asn His Lys Pro Ser Asn Thr Lys Val Asp Lys
                340                 345                 350

Lys Val Glu Pro Lys Ser Cys Asp Lys Thr His Thr Cys Pro Pro Cys
                355                 360                 365

Pro Ala Pro Glu Leu Leu Gly Gly Pro Ser Val Phe Leu Phe Pro Pro
                370                 375                 380

Lys Pro Lys Asp Thr Leu Met Ile Ser Arg Thr Pro Glu Val Thr Cys
385                 390                 395                 400

Val Val Val Asp Val Ser His Glu Asp Pro Glu Val Lys Phe Asn Trp
                405                 410                 415

Tyr Val Asp Gly Val Glu Val His Asn Ala Lys Thr Lys Pro Arg Glu
                420                 425                 430

Glu Gln Tyr Ala Ser Thr Tyr Arg Val Val Ser Val Leu Thr Val Leu
                435                 440                 445

His Gln Asp Trp Leu Asn Gly Lys Glu Tyr Lys Cys Lys Val Ser Asn
                450                 455                 460

Lys Ala Leu Pro Ala Pro Ile Glu Lys Thr Ile Ser Lys Ala Lys Gly
465                 470                 475                 480

Gln Pro Arg Glu Pro Gln Val Tyr Thr Leu Pro Pro Ser Arg Glu Glu
                485                 490                 495

Met Thr Lys Asn Gln Val Ser Leu Thr Cys Leu Val Lys Gly Phe Tyr
                500                 505                 510

Pro Ser Asp Ile Ala Val Glu Trp Glu Ser Asn Gly Gln Pro Glu Asn
                515                 520                 525

Asn Tyr Lys Thr Thr Pro Pro Val Leu Asp Ser Asp Gly Ser Phe Phe
                530                 535                 540

Leu Tyr Ser Lys Leu Thr Val Asp Lys Ser Arg Trp Gln Gln Gly Asn
545                 550                 555                 560

Val Phe Ser Cys Ser Val Met His Glu Ala Leu His Asn His Tyr Thr
                565                 570                 575

Gln Lys Ser Leu Ser Leu Ser Pro Gly Lys
                580                 585

<210> SEQ ID NO 27
<211> LENGTH: 1758
<212> TYPE: DNA
<213> ORGANISM: Artificial Sequence
<220> FEATURE:
<223> OTHER INFORMATION: H6

-continued

<400> SEQUENCE: 27

```
gaagtccagc tggtgcagag cggagccgag gtgaagaaac caggcgcttc tgtgaaggtg     60
tcctgcaagg cctctgggta catcttcacc ggctacggca tcacctgggt gcggcaggct    120
cctggccagg gcctggaatg gatgggcgag atctttccca ggagagtgca gacctactac    180
tccgagaagt tcaagggcag agtgaccatg accgctgaca cctccacctc taccgcctac    240
atggaactgc ggtctctgag atccgatgac accgctgtgt actactgcgc cagagactac    300
gacccttatt tcgccctgga ttattggggc caaggcacca ccgtgacagt cctcctcgcc    360
tctaccaagg gcccttccgt gttccccctg gcccctagca gcaagtccac atcaggaggc    420
accgctgctc tgggctgcct ggtcaaggac tacttccctg aacctgtgac cgtgtcctgg    480
aactccggcg ccctgacaag tggagtgcat accttccccg ccgtgctgca gtcctctggc    540
ctgtactctc tgtctagcgt ggtcactgtg ccttcctcta gcctcggcac acagacatac    600
atctgcaacg tgaaccacaa gccttccaac accaaagtgg acaagaaggt ggaacccaag    660
tcttgcgaca aaacccacac atgtccacct tgtcctgccc ccgagctgct gggcggcccc    720
tccgtgtttc tgtttcctcc taagccgaag gatacactga tgatctcccg gacccctgag    780
gtgacctgtg tggtggtgga cgtgtctcac gaggaccccg aagtgaagtt caactggtac    840
gtggatggcg tggaagtgca caatgctaag accaagccta gaagagca gtacgcctcc    900 acctaccggg tggtctctgt gctgaccgtc ctgcatcagg actggctgaa cggcaaagag    960
tacaagtgca aggtgtctaa caaggctctg cctgctccta tcgagaaaac catctctaag   1020
gccaagggac agcctcggga accacaagtg tacaccctgc ctccttctag agaggagatg   1080
accaagaacc aggtgagcct gacctgcctc gtgaaaggct tctacccctc tgacatcgcc   1140
gtggagtggg agtccaatgg ccagcctgag aacaactaca gaccacacc tccagttctg   1200 gactccgacg gttccttctt cctgtactcc aagctgaccg ttgataagtc cagatggcag   1260
cagggcaacg tgttctcctg ttccgtgatg cacgaggccc tgcacaacca ctacacccag   1320
aagtccctga gcttgtctcc tggcaaggaa cctaagtcta gcgacaaaac tcataccagc   1380 cccctagtc cagaggtgca gctggtggag tccgaggag actggtgca gccaggaggc   1440 tccctgaggc tgagctgcgc cgcttctggc tacaccgtgt ccagctattg tatgggctgg   1500
ttcaggcagg ctcctggcaa gggaagggag ggcgtgccg ctatcgacag cgatggcagc   1560
gtgtcttacg ccgacagcgt gaagggcaga ttcaccatct ctaaggataa ctccaagaat   1620
acactgtacc tgcagatgaa ctctctgcgc gccgaggaca ccgccgtgta cttttgcgct   1680
gctgacctgt gctgggtgga ccaggatcag ggcgagtata atacatgggg ccaggcacc   1740 ctggtgacag tgtcttcc                                                 1758
```

<210> SEQ ID NO 28
<211> LENGTH: 586
<212> TYPE: PRT
<213> ORGANISM: Artificial Sequence
<220> FEATURE:
<223> OTHER INFORMATION: H6

<400> SEQUENCE: 28

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
            20                  25                  30
```

-continued

```
Gly Ile Thr Trp Val Arg Gln Ala Pro Gly Gln Gly Leu Glu Trp Met
    35                  40                  45

Gly Glu Ile Phe Pro Arg Arg Val Gln Thr Tyr Tyr Ser Glu Lys Phe
    50                  55                  60

Lys Gly Arg Val Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445
```

```
Lys Glu Pro Lys Ser Ser Asp Lys Thr His Thr Ser Pro Pro Ser Pro
    450             455             460

Glu Val Gln Leu Val Glu Ser Gly Gly Gly Leu Val Gln Pro Gly Gly
465             470             475             480

Ser Leu Arg Leu Ser Cys Ala Ala Ser Gly Tyr Thr Val Ser Ser Tyr
            485             490             495

Cys Met Gly Trp Phe Arg Gln Ala Pro Gly Lys Gly Arg Glu Gly Val
            500             505             510

Ser Ala Ile Asp Ser Asp Gly Ser Val Ser Tyr Ala Asp Ser Val Lys
        515             520             525

Gly Arg Phe Thr Ile Ser Lys Asp Asn Ser Lys Asn Thr Leu Tyr Leu
    530             535             540

Gln Met Asn Ser Leu Arg Ala Glu Asp Thr Ala Val Tyr Phe Cys Ala
545             550             555             560

Ala Asp Leu Cys Trp Val Asp Gln Asp Gln Gly Glu Tyr Asn Thr Trp
            565             570             575

Gly Gln Gly Thr Leu Val Thr Val Ser Ser
            580             585
```

```
<210> SEQ ID NO 29
<211> LENGTH: 1053
<212> TYPE: DNA
<213> ORGANISM: Artificial Sequence
<220> FEATURE:
<223> OTHER INFORMATION: L3

<400> SEQUENCE: 29
gaggtgcagc tggtggagtc cggaggagga ctggtgcagc caggaggctc cctgaggctg      60
agctgcgccg cttctggcta caccgtgtcc agctattgta tgggctggtt caggcaggct     120
cctggcaagg gaagggaggg cgtgtccgct atcgacagcg atggcagcgt gtcttacgcc     180
gacagcgtga aggcagatt caccatctct aaggataact ccaagaatac actgtacctg      240
cagatgaact ctctgcgcgc cgaggacacc gccgtgtact tttgcgctgc tgacctgtgc     300
tgggtggacc aggatcaggg cgagtataat acatggggcc agggcaccct ggtgacagtg     360
tcttccgaac ctaagtctag cgacaaaact cataccagcc ccctagtcc agatatccag       420 atgacccagt ctcctagcag cctgagcgct tctgtgggcg acagagtgac aatcacctgt      480
agagcctctc aggacgtgtc caccgccgtg gattggtacc agcagaagcc cggcaaggct      540
cctaagctgc tgatctactc tgcctcctac cggtacacag gagtccccga tagattctct      600
ggctccggct ctggaaccga cttcaccttc accatctcct ctctgcagcc tgaggacatt      660
gccacctact actgccagca gcactactcc atccctttta ccttcggcca gggcaccaag      720
ctggaaatca gcggaccgt ggccgctcca tccgtgttca tctttcctcc ttccgacgag       780
cagctgaagt ctggcaccgc ttccgtggtg tgcctgctga caacttcta ccctcgggaa       840 gccaaggtgc agtggaaagt ggacaacgcc ctgcagtccg gcaatagcca agagtccgtc      900
accgagcaag actccaagga ctctacctat tctctctcca gcacactgac cctgtctaaa      960
gccgactacg agaagcacaa ggtgtacgcc tgcgaagtga cccaccaggg cctgtcttcc     1020
cccgtgacaa agtccttcaa cagaggcgag tgt                                  1053
```

```
<210> SEQ ID NO 30
<211> LENGTH: 351
<212> TYPE: PRT
<213> ORGANISM: Artificial Sequence
```

<220> FEATURE:
<223> OTHER INFORMATION: L3

<400> SEQUENCE: 30

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Val Ser Ser Tyr
            20                  25                  30

Cys Met Gly Trp Phe Arg Gln Ala Pro Gly Lys Gly Arg Glu Gly Val
        35                  40                  45

Ser Ala Ile Asp Ser Asp Gly Ser Val Ser Tyr Ala Asp Ser Val Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Phe Cys Ala
                85                  90                  95

Ala Asp Leu Cys Trp Val Asp Gln Asp Gln Gly Glu Tyr Asn Thr Trp
            100                 105                 110

Gly Gln Gly Thr Leu Val Thr Val Ser Ser Glu Pro Lys Ser Ser Asp
        115                 120                 125

Lys Thr His Thr Ser Pro Pro Ser Pro Asp Ile Gln Met Thr Gln Ser
    130                 135                 140

Pro Ser Ser Leu Ser Ala Ser Val Gly Asp Arg Val Thr Ile Thr Cys
145                 150                 155                 160

Arg Ala Ser Gln Asp Val Ser Thr Ala Val Asp Trp Tyr Gln Gln Lys
                165                 170                 175

Pro Gly Lys Ala Pro Lys Leu Leu Ile Tyr Ser Ala Ser Tyr Arg Tyr
            180                 185                 190

Thr Gly Val Pro Asp Arg Phe Ser Gly Ser Gly Ser Gly Thr Asp Phe
        195                 200                 205

Thr Phe Thr Ile Ser Ser Leu Gln Pro Glu Asp Ile Ala Thr Tyr Tyr
    210                 215                 220

Cys Gln Gln His Tyr Ser Ile Pro Phe Thr Phe Gly Gln Gly Thr Lys
225                 230                 235                 240

Leu Glu Ile Lys Arg Thr Val Ala Ala Pro Ser Val Phe Ile Phe Pro
                245                 250                 255

Pro Ser Asp Glu Gln Leu Lys Ser Gly Thr Ala Ser Val Val Cys Leu
            260                 265                 270

Leu Asn Asn Phe Tyr Pro Arg Glu Ala Lys Val Gln Trp Lys Val Asp
        275                 280                 285

Asn Ala Leu Gln Ser Gly Asn Ser Gln Glu Ser Val Thr Glu Gln Asp
    290                 295                 300

Ser Lys Asp Ser Thr Tyr Ser Leu Ser Ser Thr Leu Thr Leu Ser Lys
305                 310                 315                 320

Ala Asp Tyr Glu Lys His Lys Val Tyr Ala Cys Glu Val Thr His Gln
                325                 330                 335

Gly Leu Ser Ser Pro Val Thr Lys Ser Phe Asn Arg Gly Glu Cys
            340                 345                 350
```

<210> SEQ ID NO 31
<211> LENGTH: 1054
<212> TYPE: DNA
<213> ORGANISM: Artificial Sequence
<220> FEATURE:
<223> OTHER INFORMATION: H7

```
<400> SEQUENCE: 31
gaggtgcagc tggtggagtc cggaggagga ctggtgcagc caggaggctc cctgaggctg     60
agctgcgccg cttctggcta caccgtgtcc agctattgta tgggctggtt caggcaggct    120
cctggcaagg gaagggaggg cgtgtccgct atcgacagcg atggcagcgt gtcttacgcc    180
gacagcgtga agggcagatt caccatctct aaggataact ccaagaatac actgtacctg    240
cagatgaact ctctgcgcgc cgaggacacc gccgtgtact tttgcgctgc tgacctgtgc    300
tgggtggacc aggatcaggg cgagtataat acatggggcc agggcaccct ggtgacagtg    360
tcttccgaga gcaagtacgg accaccttgc ccaccatgtc cagctcctga gtttgaggga    420
ggaccatccg tgttcctgtt tcctccaaag cctaaggaca ccctgatgat cagccggaca    480
cctgaggtga cctgcgtggt ggtggacgtg tctcaggagg atccagaggt gcagttcaac    540
tggtacgtgg atggcgtgga ggtgcacaat gctaagacca gccaagaga ggagcagttt    600 aattccacat accgcgtggt gagcgtgctg accgtgctgc atcaggattg gctgaacggc    660
aaggagtata agtgcaaggt gtccaataag ggcctgccca gctctatcga aagacaatc    720 agcaaggcta agggacagcc tagggagcca caggtgtaca ccctgccccc ttctcaggag    780
gagatgacaa agaaccaggt gtccctgacc tgtctggtga agggcttcta tccaagcgac    840
atcgctgtgg agtgggagtc taatggccag cccgagaaca attacaagac cacaccaccc    900
gtgctggact ctgatggctc cttctttctg tattctaggc tgacagtgga taagtcccgg    960
tggcaggagg gcaacgtgtt tagctgctct gtgatgcacg aggccctgca caatcattat   1020
acccagaagt ccctgagcct gtctctgggc aagt                                1054

<210> SEQ ID NO 32
<211> LENGTH: 351
<212> TYPE: PRT
<213> ORGANISM: Artificial Sequence
<220> FEATURE:
<223> OTHER INFORMATION: H7

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Val Ser Ser Tyr
            20                  25                  30

Cys Met Gly Trp Phe Arg Gln Ala Pro Gly Lys Gly Arg Glu Gly Val
        35                  40                  45

Ser Ala Ile Asp Ser Asp Gly Ser Val Ser Tyr Ala Asp Ser Val Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Phe Cys Ala
                85                  90                  95

Ala Asp Leu Cys Trp Val Asp Gln Asp Gln Gly Glu Tyr Asn Thr Trp
            100                 105                 110

Gly Gln Gly Thr Leu Val Thr Val Ser Ser Glu Ser Lys Tyr Gly Pro
        115                 120                 125

Pro Cys Pro Pro Cys Pro Ala Pro Glu Phe Glu Gly Gly Pro Ser Val
    130                 135                 140

Phe Leu Phe Pro Pro Lys Pro Lys Asp Thr Leu Met Ile Ser Arg Thr
145                 150                 155                 160
```

```
Pro Glu Val Thr Cys Val Val Val Asp Val Ser Gln Glu Asp Pro Glu
                165                 170                 175

Val Gln Phe Asn Trp Tyr Val Asp Gly Val Glu Val His Asn Ala Lys
                180                 185                 190

Thr Lys Pro Arg Glu Glu Gln Phe Asn Ser Thr Tyr Arg Val Val Ser
            195                 200                 205

Val Leu Thr Val Leu His Gln Asp Trp Leu Asn Gly Lys Glu Tyr Lys
        210                 215                 220

Cys Lys Val Ser Asn Lys Gly Leu Pro Ser Ser Ile Glu Lys Thr Ile
225                 230                 235                 240

Ser Lys Ala Lys Gly Gln Pro Arg Glu Pro Gln Val Tyr Thr Leu Pro
                245                 250                 255

Pro Ser Gln Glu Glu Met Thr Lys Asn Gln Val Ser Leu Thr Cys Leu
                260                 265                 270

Val Lys Gly Phe Tyr Pro Ser Asp Ile Ala Val Glu Trp Glu Ser Asn
            275                 280                 285

Gly Gln Pro Glu Asn Asn Tyr Lys Thr Thr Pro Pro Val Leu Asp Ser
        290                 295                 300

Asp Gly Ser Phe Phe Leu Tyr Ser Arg Leu Thr Val Asp Lys Ser Arg
305                 310                 315                 320

Trp Gln Glu Gly Asn Val Phe Ser Cys Ser Val Met His Glu Ala Leu
                325                 330                 335

His Asn His Tyr Thr Gln Lys Ser Leu Ser Leu Ser Leu Gly Lys
                340                 345                 350
```

```
<210> SEQ ID NO 33
<211> LENGTH: 10
<212> TYPE: PRT
<213> ORGANISM: Artificial Sequence
<220> FEATURE:
<223> OTHER INFORMATION: Anti-LAG-3 sdAb CDR1

<400> SEQUENCE: 33

Gly Tyr Thr Val Ser Ser Tyr Cys Met Gly
1               5               10
```

```
<210> SEQ ID NO 34
<211> LENGTH: 16
<212> TYPE: PRT
<213> ORGANISM: Artificial Sequence
<220> FEATURE:
<223> OTHER INFORMATION: Anti-LAG-3 sdAb CDR2

<400> SEQUENCE: 34

Ala Ile Asp Ser Asp Gly Ser Val Ser Tyr Ala Asp Ser Val Lys Gly
1               5               10                  15
```

```
<210> SEQ ID NO 35
<211> LENGTH: 14
<212> TYPE: PRT
<213> ORGANISM: Artificial Sequence
<220> FEATURE:
<223> OTHER INFORMATION: Anti-LAG-3 sdAb CDR3

<400> SEQUENCE: 35

Asp Leu Cys Trp Val Asp Gln Asp Gln Gly Glu Tyr Asn Thr
1               5                   10
```

```
<210> SEQ ID NO 36
<211> LENGTH: 366
```

<212> TYPE: DNA
<213> ORGANISM: Artificial Sequence
<220> FEATURE:
<223> OTHER INFORMATION: Anti-LAG-3 sdAb

<400> SEQUENCE: 36

```
gaggtgcagc tggtggagtc cggaggagga ctggtgcagc caggaggctc cctgaggctg      60
agctgcgccg cttctggcta caccgtgtcc agctattgta tgggctggtt caggcaggct     120
cctggcaagg gaagggaggg cgtgtccgct atcgacagcg atggcagcgt gtcttacgcc     180
gacagcgtga aggcagatt caccatctct aaggataact ccaagaatac actgtacctg     240
cagatgaact ctctgcgcgc cgaggacacc gccgtgtact tttgcgctgc tgacctgtgc     300
tgggtggacc aggatcaggg cgagtataat acatggggcc agggcaccct ggtgacagtg     360
tcttcc                                                                366
```

<210> SEQ ID NO 37
<211> LENGTH: 122
<212> TYPE: PRT
<213> ORGANISM: Artificial Sequence
<220> FEATURE:
<223> OTHER INFORMATION: Anti-LAG-3 sdAb

<400> SEQUENCE: 37

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Val Ser Ser Tyr
            20                  25                  30

Cys Met Gly Trp Phe Arg Gln Ala Pro Gly Lys Gly Arg Glu Gly Val
        35                  40                  45

Ser Ala Ile Asp Ser Asp Gly Ser Val Ser Tyr Ala Asp Ser Val Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Phe Cys Ala
                85                  90                  95

Ala Asp Leu Cys Trp Val Asp Gln Asp Gln Gly Glu Tyr Asn Thr Trp
            100                 105                 110

Gly Gln Gly Thr Leu Val Thr Val Ser Ser
        115                 120
```

<210> SEQ ID NO 38
<211> LENGTH: 15
<212> TYPE: PRT
<213> ORGANISM: Artificial Sequence
<220> FEATURE:
<223> OTHER INFORMATION: G-Linker

<400> SEQUENCE: 38

```
Gly Gly Gly Gly Ser Gly Gly Gly Gly Ser Gly Gly Gly Gly Ser
1               5                   10                  15
```

<210> SEQ ID NO 39
<211> LENGTH: 229
<212> TYPE: PRT
<213> ORGANISM: Artificial Sequence
<220> FEATURE:
<223> OTHER INFORMATION: IgG4 Fc -continued

<400> SEQUENCE: 39

```
Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225
```

<210> SEQ ID NO 40
<211> LENGTH: 12
<212> TYPE: PRT
<213> ORGANISM: Artificial Sequence
<220> FEATURE:
<223> OTHER INFORMATION: E4-linker

<400> SEQUENCE: 40

```
Glu Ser Lys Tyr Gly Pro Pro Ser Pro Pro Ser Pro
1               5                   10
```

<210> SEQ ID NO 41
<211> LENGTH: 9
<212> TYPE: PRT
<213> ORGANISM: Artificial Sequence
<220> FEATURE:
<223> OTHER INFORMATION: G9-linker

<400> SEQUENCE: 41

```
Gly Gly Gly Gly Ser Gly Gly Gly Ser
1               5
```

<210> SEQ ID NO 42
<211> LENGTH: 12
<212> TYPE: PRT
<213> ORGANISM: Artificial Sequence
<220> FEATURE:
<223> OTHER INFORMATION: G12-linker

<400> SEQUENCE: 42

Gly Gly Gly Gly Ser Gly Gly Gly Gly Ser Gly Ser
1               5                   10

<210> SEQ ID NO 43
<211> LENGTH: 15
<212> TYPE: PRT
<213> ORGANISM: Artificial Sequence
<220> FEATURE:
<223> OTHER INFORMATION: Ea-linker

<400> SEQUENCE: 43

Glu Pro Lys Ser Ser Asp Lys Gly His Gly Gly Pro Pro Gly Pro
1               5                   10                  15

<210> SEQ ID NO 44
<211> LENGTH: 1758
<212> TYPE: DNA
<213> ORGANISM: Artificial Sequence
<220> FEATURE:
<223> OTHER INFORMATION: H8

<400> SEQUENCE: 44
gaagtccagc tggtgcagag cggagccgag gtgaagaaac caggcgcttc tgtgaaggtg      60
tcctgcaagg cctctgggta catcttcacc ggctacggca tcacctgggt gcggcaggct     120
cctggccagg gcctggaatg gatgggcgag atctttccca ggagagtgca gacctactac     180
tccgagaagt tcaagggcag agtgaccatg accaccgaca cctccacctc taccgcctac     240
atggaactgc ggtctctgag atccgatgac accgctgtgt actactgcgc cagagactac     300
gacccttatt cgccctgga  ttattggggc caaggcacca ccgtgacagt ctcctccgcc     360
tctaccaagg gcccttccgt gttccccctg gccctagca  gcaagtccac atcaggaggc     420
accgctgctc tgggctgcct ggtcaaggac tacttccctg aacctgtgac cgtgtcctgg     480
aactccggcg ccctgacaag tggagtgcat accttccccg ccgtgctgca gtcctctggc     540
ctgtactctc tgtctagcgt ggtcactgtg ccttcctcta gcctcggcac acagacatac     600
atctgcaacg tgaaccacaa gccttccaac accaaagtgg acaagaaggt ggaacccaag     660
tcttgcgaca aacccacac  atgtccacct tgtcctgccc ccgagctgct gggcggcccc     720
tccgtgtttc tgtttcctcc taagccgaag gatacactga tgatctcccg gacccctgag     780
gtgacctgtg tggtggtgga cgtgtctcac gaggaccccg aagtgaagtt caactggtac     840
gtggatggcg tggaagtgca caatgctaag accaagccta gagagagca  gtacgcctcc     900 acctaccggg tggtctctgt gctgaccgtc ctgcatcagg actggctgaa cggcaaagag     960
tacaagtgca aggtgtctaa caaggctctg cctgctccta tcgagaaaac catctctaag    1020
gccaagggac agcctcggga accacaagtg tacaccctgc ctccttctag agaggagatg    1080
accaagaacc aggtgagcct gacctgcctc gtgaaaggct tctacccctc tgacatcgcc    1140
gtggagtggg agtccaatgg ccagcctgag aacaactaca agaccacacc tccagttctg    1200
gactccgacg gttccttctt cctgtactcc aagctgaccg ttgataagtc cagatggcag    1260
cagggcaacg tgttctcctg ttccgtgatg cacgaggccc tgcacaacca ctacacccag    1320
aagtccctga gcttgtctcc tggcaagggg ggaggcggta gtggaggcgg tggttcaggc    1380
ggaggcggat ctgaggtgca gctggtggag tccggaggag gactggtgca gccaggaggc    1440

```
tccctgaggc tgagctgcgc cgcttctggc tacaccgtgt ccagctattg tatgggctgg      1500
ttcaggcagg ctcctggcaa gggaagggag ggcgtgtccg ctatcgacag cgatggcagc      1560
gtgtcttacg ccgacagcgt gaagggcaga ttcaccatct ctaaggataa ctccaagaat      1620
acactgtacc tgcagatgaa ctctctgcgc gccgaggaca ccgccgtgta cttttgcgct      1680
gctgacctgt gctgggtgga ccaggatcag ggcgagtata atacatgggg ccagggcacc      1740
ctggtgacag tgtcttcc                                                    1758
```

```
<210> SEQ ID NO 45
<211> LENGTH: 586
<212> TYPE: PRT
<213> ORGANISM: Artificial Sequence
<220> FEATURE:
<223> OTHER INFORMATION: H8

<400> SEQUENCE: 45

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Met
        35                  40                  45

Gly Glu Ile Phe Pro Arg Arg Val Gln Thr Tyr Tyr Ser Glu Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300
```

```
Val Ser Val Leu Thr Val Leu His Gln Asp Trp Leu Asn Gly Lys Glu
305             310             315             320

Tyr Lys Cys Lys Val Ser Asn Lys Ala Leu Pro Ala Pro Ile Glu Lys
                325             330             335

Thr Ile Ser Lys Ala Lys Gly Gln Pro Arg Glu Pro Gln Val Tyr Thr
            340             345             350

Leu Pro Pro Ser Arg Glu Glu Met Thr Lys Asn Gln Val Ser Leu Thr
            355             360             365

Cys Leu Val Lys Gly Phe Tyr Pro Ser Asp Ile Ala Val Glu Trp Glu
            370             375             380

Ser Asn Gly Gln Pro Glu Asn Asn Tyr Lys Thr Thr Pro Pro Val Leu
385             390             395             400

Asp Ser Asp Gly Ser Phe Phe Leu Tyr Ser Lys Leu Thr Val Asp Lys
                405             410             415

Ser Arg Trp Gln Gln Gly Asn Val Phe Ser Cys Ser Val Met His Glu
            420             425             430

Ala Leu His Asn His Tyr Thr Gln Lys Ser Leu Ser Leu Ser Pro Gly
            435             440             445

Lys Gly Gly Gly Gly Ser Gly Gly Gly Gly Ser Gly Gly Gly Gly Ser
    450             455             460

Glu Val Gln Leu Val Glu Ser Gly Gly Gly Leu Val Gln Pro Gly Gly
465             470             475             480

Ser Leu Arg Leu Ser Cys Ala Ala Ser Gly Tyr Thr Val Ser Ser Tyr
            485             490             495

Cys Met Gly Trp Phe Arg Gln Ala Pro Gly Lys Gly Arg Glu Gly Val
            500             505             510

Ser Ala Ile Asp Ser Asp Gly Ser Val Ser Tyr Ala Asp Ser Val Lys
            515             520             525

Gly Arg Phe Thr Ile Ser Lys Asp Asn Ser Lys Asn Thr Leu Tyr Leu
            530             535             540

Gln Met Asn Ser Leu Arg Ala Glu Asp Thr Ala Val Tyr Phe Cys Ala
545             550             555             560

Ala Asp Leu Cys Trp Val Asp Gln Asp Gln Gly Glu Tyr Asn Thr Trp
            565             570             575

Gly Gln Gly Thr Leu Val Thr Val Ser Ser
            580             585
```

<210> SEQ ID NO 46
<211> LENGTH: 1740
<212> TYPE: DNA
<213> ORGANISM: Artificial Sequence
<220> FEATURE:
<223> OTHER INFORMATION: H9

<400> SEQUENCE: 46

```
gaagtccagc tggtgcagag cggagccgag gtgaagaaac caggcgcttc tgtgaaggtg      60
tcctgcaagg cctctgggta catcttcacc ggctacggca tcacctgggt gcggcaggct     120
cctggccagg gcctggaatg gatgggcgag atctttccca ggagagtgca gacctactac     180
tccgagaagt tcaagggcag agtgaccatg accaccgaca cctccacctc taccgcctac     240
atggaactgc ggtctctgag atccgatgac accgctgtgt actactgcgc cagagactac     300
gacccttatt cgccctgga ttattggggc caaggcacca ccgtgacagt ctcctccgcc     360
tctaccaagg gcccttccgt gttccccctg gccctagca gcaagtccac atcaggaggc     420
accgctgctc tgggctgcct ggtcaaggac tacttccctg aacctgtgac cgtgtcctgg     480
```

-continued

```
aactccggcg ccctgacaag tggagtgcat accttccccg ccgtgctgca gtcctctggc      540
ctgtactctc tgtctagcgt ggtcactgtg ccttcctcta gcctcggcac acagacatac      600
atctgcaacg tgaaccacaa gccttccaac accaaagtgg acaagaaggt ggaacccaag      660
tcttgcgaca aaacccacac atgtccacct tgtcctgccc ccgagctgct gggcggcccc      720
tccgtgtttc tgtttcctcc taagccgaag gatacactga tgatctcccg gacccctgag      780
gtgacctgtg tggtggtgga cgtgtctcac gaggaccccg aagtgaagtt caactggtac      840
gtggatggcg tggaagtgca caatgctaag accaagccta gagaagagca gtacgcctcc      900
acctaccggg tggtctctgt gctgaccgtc ctgcatcagg actggctgaa cggcaaagag      960
tacaagtgca aggtgtctaa caaggctctg cctgctccta tcgagaaaac catctctaag     1020
gccaagggac agcctcggga accacaagtg tacaccctgc ctccttctag agaggagatg     1080
accaagaacc aggtgagcct gacctgcctc gtgaaaggct tctacccctc tgacatcgcc     1140
gtggagtggg agtccaatgg ccagcctgag aacaactaca agaccacacc tccagttctg     1200
gactccgacg gttccttctt cctgtactcc aagctgaccg ttgataagtc cagatggcag     1260
cagggcaacg tgttctcctg ttccgtgatg cacgaggccc tgcacaacca ctacacccag     1320
aagtccctga gcttgtctcc tggcaagggt ggaggcggta gtggaggcgg ttcagaggtg     1380
cagctggtgg agtccggagg aggactggtg cagccaggag ctccctgag gctgagctgc      1440 gccgcttctg gctacaccgt gtccagctat tgtatgggct ggttcaggca ggctcctggc     1500
aagggaaggg agggcgtgtc cgctatcgac agcgatggca gcgtgtctta cgccgacagc     1560
gtgaagggca gattcaccat ctctaaggat aactccaaga atacactgta cctgcagatg     1620
aactctctgc gcgccgagga caccgccgtg tactttgcg ctgctgacct gtgctgggtg      1680
gaccaggatc agggcgagta taatacatgg ggccagggca ccctggtgac agtgtcttcc     1740
```

```
<210> SEQ ID NO 47
<211> LENGTH: 580
<212> TYPE: PRT
<213> ORGANISM: Artificial Sequence
<220> FEATURE:
<223> OTHER INFORMATION: H9

<400> SEQUENCE: 47

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Met
        35                  40                  45

Gly Glu Ile Phe Pro Arg Arg Val Gln Thr Tyr Tyr Ser Glu Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140
```

-continued

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys Gly Gly Gly Ser Gly Gly Gly Ser Glu Val Gln Leu Val Glu
    450                 455                 460

Ser Gly Gly Gly Leu Val Gln Pro Gly Gly Ser Leu Arg Leu Ser Cys
465                 470                 475                 480

Ala Ala Ser Gly Tyr Thr Val Ser Ser Tyr Cys Met Gly Trp Phe Arg
            485                 490                 495

Gln Ala Pro Gly Lys Gly Arg Glu Gly Val Ser Ala Ile Asp Ser Asp
            500                 505                 510

Gly Ser Val Ser Tyr Ala Asp Ser Val Lys Gly Arg Phe Thr Ile Ser
            515                 520                 525

Lys Asp Asn Ser Lys Asn Thr Leu Tyr Leu Gln Met Asn Ser Leu Arg
    530                 535                 540

Ala Glu Asp Thr Ala Val Tyr Phe Cys Ala Ala Asp Leu Cys Trp Val
545                 550                 555                 560
```

```
Asp Gln Asp Gln Gly Glu Tyr Asn Thr Trp Gly Gln Gly Thr Leu Val
            565                 570                 575

Thr Val Ser Ser
            580
```

<210> SEQ ID NO 48
<211> LENGTH: 1758
<212> TYPE: DNA
<213> ORGANISM: Artificial Sequence
<220> FEATURE:
<223> OTHER INFORMATION: H10

<400> SEQUENCE: 48

```
gaagtccagc tggtgcagag cggagccgag gtgaagaaac caggcgcttc tgtgaaggtg      60
tcctgcaagg cctctgggta catcttcacc ggctacggca tcacctgggt gcggcaggct     120
cctggccagg gcctggaatg gatgggcgag atctttccca ggagagtgca gacctactac     180
tccgagaagt tcaagggcag agtgaccatg accaccgaca cctccacctc taccgcctac     240
atggaactgc ggtctctgag atccgatgac accgctgtgt actactgcgc cagagactac     300
gacccttatt tcgccctgga ttattggggc caaggcacca ccgtgacagt ctcctccgcc     360
tctaccaagg gcccttccgt gttccccctg gcccctagca gcaagtccac atcaggaggc     420
accgctgctc tgggctgcct ggtcaaggac tacttccctg aacctgtgac cgtgtcctgg     480
aactccggcg ccctgacaag tggagtgcat accttccccg ccgtgctgca gtcctctggc     540
ctgtactctc tgtctagcgt ggtcactgtg ccttcctcta gcctcggcac acagacatac     600
atctgcaacg tgaaccacaa gccttccaac accaaagtgg acaagaaggt ggaacccaag     660
tcttgcgaca aaacccacac atgtccacct tgtcctgccc ccgagctgct gggcggcccc     720
tccgtgtttc tgtttcctcc taagccgaag gatacactga tgatctcccg gacccctgag     780
gtgacctgtg tggtggtgga cgtgtctcac gaggaccccg aagtgaagtt caactggtac     840
gtggatggcg tggaagtgca caatgctaag accaagccta gaagagagca gtacgcctcc     900
acctaccggg tggtctctgt gctgaccgtc ctgcatcagg actggctgaa cggcaaagag     960
tacaagtgca aggtgtctaa caaggctctg cctgctccta tcgagaaaac catctctaag    1020
gccaagggac agcctcggga accacaagtg tacaccctgc ctccttctag agaggagatg    1080
accaagaacc aggtgagcct gacctgcctc gtgaaaggct tctacccctc tgacatcgcc    1140
gtggagtggg agtccaatgg ccagcctgag aacaactaca gaccacacc tccagttctg     1200 gactccgacg gttccttctt cctgtactcc aagctgaccg ttgataagtc cagatggcag    1260
cagggcaacg tgttctcctg ttccgtgatg cacgaggccc tgcacaacca ctacacccag    1320
aagtccctga gcttgtctcc tggcaaggaa cctaagtcta gcgacaaagg ccatggaggt    1380 cccctggac cagaggtgca gctggtggag tccggaggag gactggtgca gccaggaggc     1440
tccctgaggc tgagctgcgc cgcttctggc tacaccgtgt ccagctattg tatgggctgg    1500
ttcaggcagg ctcctggcaa gggaagggag ggcgtgtccg ctatcgacag cgatggcagc    1560
gtgtcttacg ccgacagcgt gaagggcaga ttcaccatct ctaaggataa ctccaagaat    1620
acactgtacc tgcagatgaa ctctctgcgc gccgaggaca ccgccgtgta cttttgcgct    1680
gctgacctgt gctgggtgga ccaggatcag ggcgagtata atacatgggg ccagggcacc    1740
ctggtgacag tgtcttcc                                                  1758
```

<210> SEQ ID NO 49
<211> LENGTH: 586

```
<212> TYPE: PRT
<213> ORGANISM: Artificial Sequence
<220> FEATURE:
<223> OTHER INFORMATION: H10

<400> SEQUENCE: 49

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
                20                  25                  30

Gly Ile Thr Trp Val Arg Gln Ala Pro Gly Gln Gly Leu Glu Trp Met
            35                  40                  45

Gly Glu Ile Phe Pro Arg Arg Val Gln Thr Tyr Tyr Ser Glu Lys Phe
        50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
                100                 105                 110

Thr Thr Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Ala Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
        370                 375                 380
```

```
Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys Glu Pro Lys Ser Ser Asp Lys Gly His Gly Gly Pro Pro Gly Pro
        450                 455                 460

Glu Val Gln Leu Val Glu Ser Gly Gly Gly Leu Val Gln Pro Gly Gly
465                 470                 475                 480

Ser Leu Arg Leu Ser Cys Ala Ala Ser Gly Tyr Thr Val Ser Ser Tyr
                485                 490                 495

Cys Met Gly Trp Phe Arg Gln Ala Pro Gly Lys Gly Arg Glu Gly Val
                500                 505                 510

Ser Ala Ile Asp Ser Asp Gly Ser Val Ser Tyr Ala Asp Ser Val Lys
            515                 520                 525

Gly Arg Phe Thr Ile Ser Lys Asp Asn Ser Lys Asn Thr Leu Tyr Leu
        530                 535                 540

Gln Met Asn Ser Leu Arg Ala Glu Asp Thr Ala Val Tyr Phe Cys Ala
545                 550                 555                 560

Ala Asp Leu Cys Trp Val Asp Gln Asp Gln Gly Glu Tyr Asn Thr Trp
                565                 570                 575

Gly Gln Gly Thr Leu Val Thr Val Ser Ser
            580                 585
```

```
<210> SEQ ID NO 50
<211> LENGTH: 1749
<212> TYPE: DNA
<213> ORGANISM: Artificial Sequence
<220> FEATURE:
<223> OTHER INFORMATION: H11

<400> SEQUENCE: 50
gaggtgcagc tggtggagtc cggaggagga ctggtgcagc caggaggctc cctgaggctg          60
agctgcgccg cttctggcta caccgtgtcc agctattgta tgggctggtt caggcaggct         120
cctggcaagg gaagggaggg cgtgtccgct atcgacagcg atggcagcgt gtcttacgcc         180
gacagcgtga aggcagatt caccatctct aaggataact ccaagaatac actgtacctg          240
cagatgaact ctctgcgcgc cgaggacacc gccgtgtact tttgcgctgc tgacctgtgc         300
tgggtggacc aggatcaggg cgagtataat acatggggcc agggcaccct ggtgacagtg         360
tcttccggtg gaggcggtag tggaggcggt ggttcaggat ctgaagtcca gctggtgcag         420
agcggagccg aggtgaagaa accaggcgct tctgtgaagg tgtcctgcaa ggcctctggg         480
tacatcttca ccggctacgg catcacctgg gtgcggcagg ctcctggcca gggcctggaa         540
tggatgggcg agatctttcc caggagagtg cagacctact actccgagaa gttcaagggc         600
agagtgacca tgaccaccga cacctccacc tctaccgcct acatggaact gcggtctctg         660
agatccgatg acaccgctgt gtactactgc gccagagact acgacccta tttcgccctg          720 gattattggg gccaaggcac caccgtgaca gtctcctccg cctctaccaa gggcccttcc         780
gtgttccccc tggcccctag cagcaagtcc acatcaggag gcaccgctgc tctgggctgc         840
ctggtcaagg actacttccc tgaacctgtg accgtgtcct ggaactccgg cgccctgaca         900
```

```
agtggagtgc ataccttccc cgccgtgctg cagtcctctg gcctgtactc tctgtctagc     960
gtggtcactg tgccttcctc tagcctcggc acacagacat acatctgcaa cgtgaaccac    1020
aagccttcca acaccaaagt ggacaagaag gtggaaccca agtcttgcga caaaacccac    1080
acatgtccac cttgtcctgc ccccgagctg ctgggcggcc cctccgtgtt tctgtttcct    1140
cctaagccga aggatacact gatgatctcc cggacccctg aggtgacctg tgtggtggtg    1200
gacgtgtctc acgaggaccc cgaagtgaag ttcaactggt acgtggatgg cgtggaagtg    1260
cacaatgcta agaccaagcc tagagaagag cagtacgcct ccacctaccg ggtggtctct    1320
gtgctgaccg tcctgcatca ggactggctg aacggcaaag agtacaagtg caaggtgtct    1380
aacaaggctc tgcctgctcc tatcgagaaa accatctcta aggccaaggg acagcctcgg    1440
gaaccacaag tgtacaccct gcctccttct agagaggaga tgaccaagaa ccaggtgagc    1500
ctgacctgcc tcgtgaaagg cttctacccc tctgacatcg ccgtggagtg ggagtccaat    1560
ggccagcctg agaacaacta caagaccaca cctccagttc tggactccga cggttccttc    1620
ttcctgtact ccaagctgac cgttgataag tccagatggc agcagggcaa cgtgttctcc    1680
tgttccgtga tgcacgaggc cctgcacaac cactacaccc agaagtccct gagcttgtct    1740
cctggcaag                                                            1749
```

<210> SEQ ID NO 51
<211> LENGTH: 583
<212> TYPE: PRT
<213> ORGANISM: Artificial Sequence
<220> FEATURE:
<223> OTHER INFORMATION: H11

<400> SEQUENCE: 51

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Val Ser Ser Tyr
            20                  25                  30

Cys Met Gly Trp Phe Arg Gln Ala Pro Gly Lys Gly Arg Glu Gly Val
        35                  40                  45

Ser Ala Ile Asp Ser Asp Gly Ser Val Ser Tyr Ala Asp Ser Val Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Phe Cys Ala
                85                  90                  95

Ala Asp Leu Cys Trp Val Asp Gln Asp Gln Gly Glu Tyr Asn Thr Trp
            100                 105                 110

Gly Gln Gly Thr Leu Val Thr Val Ser Ser Gly Gly Gly Gly Ser Gly
        115                 120                 125

Gly Gly Gly Ser Gly Ser Glu Val Gln Leu Val Gln Ser Gly Ala Glu
    130                 135                 140

Val Lys Lys Pro Gly Ala Ser Val Lys Val Ser Cys Lys Ala Ser Gly
145                 150                 155                 160

Tyr Ile Phe Thr Gly Tyr Gly Ile Thr Trp Val Arg Gln Ala Pro Gly
                165                 170                 175

Gln Gly Leu Glu Trp Met Gly Glu Ile Phe Pro Arg Arg Val Gln Thr
            180                 185                 190

Tyr Tyr Ser Glu Lys Phe Lys Gly Arg Val Thr Met Thr Thr Asp Thr
            195                 200                 205
```

```
Ser Thr Ser Thr Ala Tyr Met Glu Leu Arg Ser Leu Arg Ser Asp Asp
    210                 215                 220

Thr Ala Val Tyr Tyr Cys Ala Arg Asp Tyr Asp Pro Tyr Phe Ala Leu
225                 230                 235                 240

Asp Tyr Trp Gly Gln Gly Thr Thr Val Thr Val Ser Ser Ala Ser Thr
            245                 250                 255

Lys Gly Pro Ser Val Phe Pro Leu Ala Pro Ser Ser Lys Ser Thr Ser
            260                 265                 270

Gly Gly Thr Ala Ala Leu Gly Cys Leu Val Lys Asp Tyr Phe Pro Glu
        275                 280                 285

Pro Val Thr Val Ser Trp Asn Ser Gly Ala Leu Thr Ser Gly Val His
    290                 295                 300

Thr Phe Pro Ala Val Leu Gln Ser Ser Gly Leu Tyr Ser Leu Ser Ser
305                 310                 315                 320

Val Val Thr Val Pro Ser Ser Ser Leu Gly Thr Gln Thr Tyr Ile Cys
            325                 330                 335

Asn Val Asn His Lys Pro Ser Asn Thr Lys Val Asp Lys Lys Val Glu
            340                 345                 350

Pro Lys Ser Cys Asp Lys Thr His Thr Cys Pro Pro Cys Pro Ala Pro
            355                 360                 365

Glu Leu Leu Gly Gly Pro Ser Val Phe Leu Phe Pro Pro Lys Pro Lys
    370                 375                 380

Asp Thr Leu Met Ile Ser Arg Thr Pro Glu Val Thr Cys Val Val Val
385                 390                 395                 400

Asp Val Ser His Glu Asp Pro Glu Val Lys Phe Asn Trp Tyr Val Asp
            405                 410                 415

Gly Val Glu Val His Asn Ala Lys Thr Lys Pro Arg Glu Glu Gln Tyr
            420                 425                 430

Ala Ser Thr Tyr Arg Val Val Ser Val Leu Thr Val Leu His Gln Asp
            435                 440                 445

Trp Leu Asn Gly Lys Glu Tyr Lys Cys Lys Val Ser Asn Lys Ala Leu
    450                 455                 460

Pro Ala Pro Ile Glu Lys Thr Ile Ser Lys Ala Lys Gly Gln Pro Arg
465                 470                 475                 480

Glu Pro Gln Val Tyr Thr Leu Pro Pro Ser Arg Glu Glu Met Thr Lys
            485                 490                 495

Asn Gln Val Ser Leu Thr Cys Leu Val Lys Gly Phe Tyr Pro Ser Asp
            500                 505                 510

Ile Ala Val Glu Trp Glu Ser Asn Gly Gln Pro Glu Asn Asn Tyr Lys
            515                 520                 525

Thr Thr Pro Pro Val Leu Asp Ser Asp Gly Ser Phe Phe Leu Tyr Ser
    530                 535                 540

Lys Leu Thr Val Asp Lys Ser Arg Trp Gln Gln Gly Asn Val Phe Ser
545                 550                 555                 560

Cys Ser Val Met His Glu Ala Leu His Asn His Tyr Thr Gln Lys Ser
            565                 570                 575

Leu Ser Leu Ser Pro Gly Lys
            580
```

```
<210> SEQ ID NO 52
<211> LENGTH: 1044
<212> TYPE: DNA
<213> ORGANISM: Artificial Sequence
<220> FEATURE:
<223> OTHER INFORMATION: L4
```

-continued

<400> SEQUENCE: 52

```
gatatccaga tgacccagtc tcctagcagc ctgagcgctt ctgtgggcga cagagtgaca      60
atcacctgta gagcctctca ggacgtgtcc accgccgtgg attggtacca gcagaagccc     120
ggcaaggctc ctaagctgct gatctactct gcctcctacc ggtacacagg agtccccgat     180
agattctctg gctccggctc tggaaccgac ttcaccttca ccatctcctc tctgcagcct     240
gaggacattg ccacctacta ctgccagcag cactactcca tcccttttac cttcggccag     300
ggcaccaagc tggaaatcaa gcggaccgtg gccgctccat ccgtgttcat ctttcctcct     360
tccgacgagc agctgaagtc tggcaccgct tccgtggtgt gcctgctgaa caacttctac     420
cctcgggaag ccaaggtgca gtggaaagtg gacaacgccc tgcagtccgg caatagccaa     480
gagtccgtca ccgagcaaga ctccaaggac tctacctatt ctctctccag cacactgacc     540
ctgtctaaag ccgactacga gaagcacaag gtgtacgcct gcgaagtgac ccaccagggc     600
ctgtcttccc ccgtgacaaa gtccttcaac agaggcgagt gtgaatcgaa gtacggacct     660
ccatctccac ctagtccaga ggtgcagctg gtggagtccg gaggaggact ggtgcagcca     720
ggaggctccc tgaggctgag ctgcgccgct tctggctaca ccgtgtccag ctattgtatg     780
ggctggttca ggcaggctcc tggcaaggga agggagggcg tgtccgctat cgacagcgat     840
ggcagcgtgt cttacgccga cagcgtgaag ggcagattca ccatctctaa ggataactcc     900
aagaatacac tgtacctgca gatgaactct ctgcgcgccg aggacaccgc cgtgtacttt     960
tgcgctgctg acctgtgctg gtggaccag gatcagggcg agtataatac atggggccag    1020
ggcaccctgg tgacagtgtc ttcc                                          1044
```

<210> SEQ ID NO 53
<211> LENGTH: 348
<212> TYPE: PRT
<213> ORGANISM: Artificial Sequence
<220> FEATURE:
<223> OTHER INFORMATION: L4

<400> SEQUENCE: 53

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Asp Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Ile Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

-continued

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys Glu Ser Lys Tyr Gly Pro Pro Ser Pro Pro
        210                 215                 220

Ser Pro Glu Val Gln Leu Val Glu Ser Gly Gly Gly Leu Val Gln Pro
225                 230                 235                 240

Gly Gly Ser Leu Arg Leu Ser Cys Ala Ala Ser Gly Tyr Thr Val Ser
                245                 250                 255

Ser Tyr Cys Met Gly Trp Phe Arg Gln Ala Pro Gly Lys Gly Arg Glu
                260                 265                 270

Gly Val Ser Ala Ile Asp Ser Asp Gly Ser Val Ser Tyr Ala Asp Ser
            275                 280                 285

Val Lys Gly Arg Phe Thr Ile Ser Lys Asp Asn Ser Lys Asn Thr Leu
        290                 295                 300

Tyr Leu Gln Met Asn Ser Leu Arg Ala Glu Asp Thr Ala Val Tyr Phe
305                 310                 315                 320

Cys Ala Ala Asp Leu Cys Trp Val Asp Gln Asp Gln Gly Glu Tyr Asn
                325                 330                 335

Thr Trp Gly Gln Gly Thr Leu Val Thr Val Ser Ser
                340                 345
```

```
<210> SEQ ID NO 54
<211> LENGTH: 1749
<212> TYPE: DNA
<213> ORGANISM: Artificial Sequence
<220> FEATURE:
<223> OTHER INFORMATION: H12

<400> SEQUENCE: 54
gaagtccagc tggtgcagag cggagccgag gtgaagaaac caggcgcttc tgtgaaggtg      60
tcctgcaagg cctctgggta catcttcacc ggctacggca tcacctgggt gcggcaggct     120
cctggccagg gcctggaatg gatgggcgag atctttccca ggagagtgca gacctactac     180
tccgagaagt tcaagggcag agtgaccatg accaccgaca cctccacctc taccgcctac     240
atggaactgc ggtctctgag atccgatgac accgctgtgt actactgcgc cagagactac     300
gacccttatt tcgccctgga ttattggggc caaggcacca ccgtgacagt cctcctccgcc    360 tctaccaagg gcccttccgt gttccccctg cccctagca gcaagtccac atcaggaggc      420
accgctgctc tgggctgcct ggtcaaggac tacttccctg aacctgtgac cgtgtcctgg     480
aactccggcg ccctgacaag tggagtgcat accttccccg ccgtgctgca gtcctctggc     540
ctgtactctc tgtctagcgt ggtcactgtg ccttcctcta gcctcggcac acagacatac     600
atctgcaacg tgaaccacaa gccttccaac accaaagtgg acaagaaggt ggaacccaag     660
tcttgcgaca aaacccacac atgtccacct tgtcctgccc ccgagctgct gggcggcccc     720
tccgtgtttc tgtttcctcc taagccgaag gatacactga tgatctcccg gacccctgag     780
gtgacctgtg tggtggtgga cgtgtctcac gaggaccccg aagtgaagtt caactggtac     840
gtggatggcg tggaagtgca caatgctaag accaagccta gagagagca gtacgcctcc      900 acctaccggg tggtctctgt gctgaccgtc ctgcatcagg actggctgaa cggcaaagag     960
tacaagtgca aggtgtctaa caaggctctg cctgctccta tcgagaaaac catctctaag    1020
```

```
gccaagggac agcctcggga accacaagtg tacaccctgc ctccttctag agaggagatg      1080
accaagaacc aggtgagcct gacctgcctc gtgaaaggct tctacccctc tgacatcgcc      1140
gtggagtggg agtccaatgg ccagcctgag aacaactaca agaccacacc tccagttctg      1200
gactccgacg gttccttctt cctgtactcc aagctgaccg ttgataagtc cagatggcag      1260
cagggcaacg tgttctcctg ttccgtgatg cacgaggccc tgcacaacca ctacacccag      1320
aagtccctga gcttgtctcc tggcaaggaa tcgaagtacg gacctccatc tccacctagt      1380
ccagaggtgc agctggtgga gtccggagga ggactggtgc agccaggagg ctccctgagg      1440
ctgagctgcg ccgcttctgg ctacaccgtg tccagctatt gtatgggctg gttcaggcag      1500
gctcctggca agggaaggga gggcgtgtcc gctatcgaca gcgatggcag cgtgtcttac      1560
gccgacagcg tgaagggcag attcaccatc tctaaggata actccaagaa tacactgtac      1620
ctgcagatga actctctgcg cgccgaggac accgccgtgt acttttgcgc tgctgacctg      1680
tgctgggtgg accaggatca gggcgagtat aatacatggg ccagggcac cctggtgaca      1740 gtgtcttcc                                                             1749
```

```
<210> SEQ ID NO 55
<211> LENGTH: 583
<212> TYPE: PRT
<213> ORGANISM: Artificial Sequence
<220> FEATURE:
<223> OTHER INFORMATION: H12

<400> SEQUENCE: 55

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Met
        35                  40                  45

Gly Glu Ile Phe Pro Arg Arg Val Gln Thr Tyr Tyr Ser Glu Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220
```

-continued

```
Thr His Thr Cys Pro Pro Cys Pro Ala Pro Glu Leu Leu Gly Gly Pro
225             230             235                 240

Ser Val Phe Leu Phe Pro Pro Lys Pro Lys Asp Thr Leu Met Ile Ser
                245             250                 255

Arg Thr Pro Glu Val Thr Cys Val Val Val Asp Val Ser His Glu Asp
            260             265             270

Pro Glu Val Lys Phe Asn Trp Tyr Val Asp Gly Val Glu Val His Asn
        275             280             285

Ala Lys Thr Lys Pro Arg Glu Glu Gln Tyr Ala Ser Thr Tyr Arg Val
    290             295                 300

Val Ser Val Leu Thr Val Leu His Gln Asp Trp Leu Asn Gly Lys Glu
305             310             315                 320

Tyr Lys Cys Lys Val Ser Asn Lys Ala Leu Pro Ala Pro Ile Glu Lys
                325             330             335

Thr Ile Ser Lys Ala Lys Gly Gln Pro Arg Glu Pro Gln Val Tyr Thr
                340             345             350

Leu Pro Pro Ser Arg Glu Glu Met Thr Lys Asn Gln Val Ser Leu Thr
            355             360             365

Cys Leu Val Lys Gly Phe Tyr Pro Ser Asp Ile Ala Val Glu Trp Glu
    370             375             380

Ser Asn Gly Gln Pro Glu Asn Asn Tyr Lys Thr Thr Pro Pro Val Leu
385             390             395                 400

Asp Ser Asp Gly Ser Phe Phe Leu Tyr Ser Lys Leu Thr Val Asp Lys
                405             410             415

Ser Arg Trp Gln Gln Gly Asn Val Phe Ser Cys Ser Val Met His Glu
            420             425             430

Ala Leu His Asn His Tyr Thr Gln Lys Ser Leu Ser Leu Ser Pro Gly
            435             440             445

Lys Glu Ser Lys Tyr Gly Pro Pro Ser Pro Pro Ser Pro Glu Val Gln
    450             455             460

Leu Val Glu Ser Gly Gly Gly Leu Val Gln Pro Gly Gly Ser Leu Arg
465             470             475                 480

Leu Ser Cys Ala Ala Ser Gly Tyr Thr Val Ser Ser Tyr Cys Met Gly
            485             490             495

Trp Phe Arg Gln Ala Pro Gly Lys Gly Arg Glu Gly Val Ser Ala Ile
            500             505             510

Asp Ser Asp Gly Ser Val Ser Tyr Ala Asp Ser Val Lys Gly Arg Phe
        515             520             525

Thr Ile Ser Lys Asp Asn Ser Lys Asn Thr Leu Tyr Leu Gln Met Asn
    530             535             540

Ser Leu Arg Ala Glu Asp Thr Ala Val Tyr Phe Cys Ala Ala Asp Leu
545             550             555                 560

Cys Trp Val Asp Gln Asp Gln Gly Glu Tyr Asn Thr Trp Gly Gln Gly
            565             570             575

Thr Leu Val Thr Val Ser Ser
            580
```